(12) United States Patent
Weiss

(10) Patent No.: US 10,832,245 B2
(45) Date of Patent: *Nov. 10, 2020

(54) UNIVERSAL SECURE REGISTRY

(71) Applicant: UNIVERSAL SECURE REGISTRY, LLC, Newton, MA (US)

(72) Inventor: Kenneth P. Weiss, Newton, MA (US)

(73) Assignee: UNIVSERSAL SECURE REGISTRY, LLC, Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/833,006

(22) Filed: Mar. 27, 2020

(65) Prior Publication Data

US 2020/0226611 A1    Jul. 16, 2020

Related U.S. Application Data

(63) Continuation of application No. 16/590,872, filed on Oct. 2, 2019, now Pat. No. 10,733,607, which is a
(Continued)

(51) Int. Cl.
*G06Q 20/40* (2012.01)
*G06Q 10/06* (2012.01)
(Continued)

(52) U.S. Cl.
CPC ....... *G06Q 20/40145* (2013.01); *G06F 21/32* (2013.01); *G06F 21/35* (2013.01);
(Continued)

(58) Field of Classification Search
CPC ........... G06Q 20/40145; G06Q 20/206; G06Q 20/3672; G06Q 20/4012; G06Q 20/3676; G06Q 20/40; G06Q 30/06
See application file for complete search history.

(56) References Cited

U.S. PATENT DOCUMENTS

| 4,720,860 A | 1/1988 | Weiss |
| 4,856,062 A | 8/1989 | Weiss |

(Continued)

FOREIGN PATENT DOCUMENTS

| EP | 0986209 A2 | 3/2000 |
| EP | 1028401 A2 | 8/2000 |

(Continued)

OTHER PUBLICATIONS

"Biometrics: Who's Watching You?" Electronic Frontier Foundation (EFF), Sep. 2003, all pages, http://www.eff.org/wp/biometrics-whos-watching-you.

(Continued)

*Primary Examiner* — Johann Y Choo
(74) *Attorney, Agent, or Firm* — Lando & Anastasi, LLP

(57) ABSTRACT

According to some aspects of the disclosure, an electronic ID device is configured to allow a user to select an account associated with the user to employ in a transaction. The electronic ID device comprises a biometric sensor configured to receive a biometric input provided by the user, a user interface configured to receive a user input, a communication interface configured to communicate with a secure registry, and a processor coupled to the biometric sensor to receive information concerning the biometric input.

17 Claims, 29 Drawing Sheets

Related U.S. Application Data continuation of application No. 14/071,126, filed on Nov. 4, 2013, which is a continuation of application No. 13/237,184, filed on Sep. 20, 2011, now Pat. No. 8,577,813, which is a continuation-in-part of application No. 13/168,556, filed on Jun. 24, 2011, now Pat. No. 8,271,397, which is a continuation of application No. 11/677,490, filed on Feb. 21, 2007, now Pat. No. 8,001,055, which is a continuation of application No. 12/393,586, filed on Feb. 26, 2009, now Pat. No. 8,234,220, which is a continuation-in-part of application No. 11/760,732, filed on Jun. 8, 2007, now Pat. No. 7,809,651, which is a continuation of application No. 11/677,490, filed on Feb. 21, 2007, now Pat. No. 8,001,055, which is a continuation of application No. 12/393,586, filed on Feb. 26, 2009, now Pat. No. 8,234,220, which is a continuation-in-part of application No. 11/760,732, filed on Jun. 8, 2007, now Pat. No. 7,809,651, which is a continuation of application No. 11/677,490, filed on Feb. 21, 2007, now Pat. No. 8,001,055, which is a continuation of application No. 11/760,729, filed on Jun. 8, 2007, now Pat. No. 7,805,372.

(60) Provisional application No. 60/859,235, filed on Nov. 15, 2006, provisional application No. 60/812,279, filed on Jun. 9, 2006, provisional application No. 60/775,046, filed on Feb. 21, 2006, provisional application No. 61/031,529, filed on Feb. 26, 2008.

(51) Int. Cl.

| | |
|---|---|
| *G06Q 20/36* | (2012.01) |
| *G06Q 20/38* | (2012.01) |
| *G06Q 30/06* | (2012.01) |
| *G06Q 40/02* | (2012.01) |
| *G06Q 50/22* | (2018.01) |
| *G06F 21/32* | (2013.01) |
| *G06F 21/35* | (2013.01) |
| *G06F 21/62* | (2013.01) |
| *H04L 9/30* | (2006.01) |
| *H04L 9/32* | (2006.01) |
| *H04L 29/06* | (2006.01) |
| *G07C 9/27* | (2020.01) |
| *G07C 9/25* | (2020.01) |
| *G06Q 20/20* | (2012.01) |
| *G07C 9/26* | (2020.01) |

(52) U.S. Cl.
CPC ......... *G06F 21/6245* (2013.01); *G06Q 10/06* (2013.01); *G06Q 20/20* (2013.01); *G06Q 20/206* (2013.01); *G06Q 20/3672* (2013.01); *G06Q 20/3674* (2013.01); *G06Q 20/3676* (2013.01); *G06Q 20/382* (2013.01); *G06Q 20/385* (2013.01); *G06Q 20/3821* (2013.01); *G06Q 20/40* (2013.01); *G06Q 20/4012* (2013.01); *G06Q 30/06* (2013.01); *G06Q 40/02* (2013.01); *G06Q 50/22* (2013.01); *G07C 9/257* (2020.01); *G07C 9/27* (2020.01); *H04L 9/30* (2013.01); *H04L 9/32* (2013.01); *H04L 9/3231* (2013.01); *H04L 9/3271* (2013.01); *H04L 63/0853* (2013.01); *H04L 63/0861* (2013.01); *H04L 63/102* (2013.01); *G06F 2221/2115* (2013.01); *G07C 9/26* (2020.01); *H04L 2209/56* (2013.01); *H04L 2209/805* (2013.01)

(56) References Cited

U.S. PATENT DOCUMENTS

| | | |
|---|---|---|
| 4,885,778 A | 12/1989 | Weiss |
| 4,998,279 A | 3/1991 | Weiss |
| 5,023,908 A | 6/1991 | Weiss |
| 5,058,161 A | 10/1991 | Weiss |
| 5,097,505 A | 3/1992 | Weiss |
| 5,168,520 A | 12/1992 | Weiss |
| 5,237,614 A | 8/1993 | Weiss |
| 5,280,527 A | 1/1994 | Gullman et al. |
| 5,361,062 A | 11/1994 | Weiss et al. |
| 5,367,572 A | 11/1994 | Weiss |
| 5,398,285 A | 3/1995 | Borgelt et al. |
| 5,457,747 A | 10/1995 | Drexler et al. |
| 5,479,512 A | 12/1995 | Weiss |
| 5,485,519 A | 1/1996 | Weiss |
| 5,615,277 A | 3/1997 | Hoffman |
| 5,657,388 A | 8/1997 | Weiss |
| 5,664,109 A | 9/1997 | Johnson et al. |
| 5,813,006 A | 9/1998 | Polnerow et al. |
| 5,870,723 A | 2/1999 | Pare, Jr. et al. |
| 5,915,023 A | 6/1999 | Bernstein |
| 5,930,767 A | 7/1999 | Reber et al. |
| 5,971,272 A | 10/1999 | Hsiao |
| 6,000,832 A | 12/1999 | Franklin et al. |
| 6,016,476 A | 1/2000 | Maes et al. |
| 6,073,106 A | 6/2000 | Rozen et al. |
| 6,088,450 A | 7/2000 | Davis et al. |
| 6,098,053 A | 8/2000 | Slater |
| 6,130,621 A | 10/2000 | Weiss |
| 6,163,771 A | 12/2000 | Walker et al. |
| 6,202,055 B1 | 3/2001 | Houvener et al. |
| 6,253,202 B1 | 6/2001 | Gilmour |
| 6,253,203 B1 | 6/2001 | O'Flaherty et al. |
| 6,260,039 B1 | 7/2001 | Schneck et al. |
| 6,308,203 B1 | 10/2001 | Itabashi et al. |
| 6,309,342 B1 | 10/2001 | Blazey et al. |
| 6,393,421 B1 | 5/2002 | Paglin |
| 6,453,301 B1 | 9/2002 | Niwa |
| 6,498,861 B1 | 12/2002 | Hamid et al. |
| 6,516,315 B1 | 2/2003 | Gupta |
| 6,546,005 B1 | 4/2003 | Berkley et al. |
| 6,581,059 B1 | 6/2003 | Barrett et al. |
| 6,640,211 B1 | 10/2003 | Holden |
| 6,658,400 B2 | 12/2003 | Perell et al. |
| 6,678,821 B1 | 1/2004 | Waugh et al. |
| 6,819,219 B1 | 11/2004 | Bolle et al. |
| 6,820,204 B1 | 11/2004 | Desai et al. |
| 6,845,448 B1 | 1/2005 | Chaganti et al. |
| 6,941,271 B1 | 9/2005 | Soong |
| 6,950,521 B1 | 9/2005 | Marcovici et al. |
| 6,950,939 B2 | 9/2005 | Tobin |
| 7,007,298 B1 | 2/2006 | Shinzaki et al. |
| 7,237,117 B2 | 6/2007 | Weiss |
| 7,249,112 B2 | 7/2007 | Berardi et al. |
| 7,278,026 B2 | 10/2007 | McGowan |
| 7,412,604 B1 | 8/2008 | Doyle |
| 7,489,781 B2 | 2/2009 | Klassen et al. |
| 7,502,459 B1 | 3/2009 | Moseley |
| 7,548,981 B1 | 6/2009 | Taylor et al. |
| 7,552,333 B2 | 6/2009 | Wheeler et al. |
| 7,552,467 B2 | 6/2009 | Lindsay |
| 7,567,934 B2 | 7/2009 | Flitcroft et al. |
| 7,571,139 B1 | 8/2009 | Giordano et al. |
| 7,597,250 B2 | 10/2009 | Finn |
| 7,657,639 B2 | 2/2010 | Hinton |
| 7,705,732 B2 | 4/2010 | Bishop et al. |
| 7,742,967 B1 | 6/2010 | Keresman, III et al. |
| 7,766,223 B1 | 8/2010 | Mello et al. |
| 7,805,372 B2 | 9/2010 | Weiss |
| 7,809,651 B2 | 10/2010 | Weiss |
| 7,865,448 B2 | 1/2011 | Pizarro |
| 8,001,055 B2 | 8/2011 | Weiss |
| 8,079,079 B2 | 12/2011 | Zhang et al. |
| 8,219,495 B2 | 7/2012 | Niwa |
| 8,234,220 B2 | 7/2012 | Weiss |
| 8,271,397 B2 | 9/2012 | Weiss |

(56) References Cited

U.S. PATENT DOCUMENTS

| | | |
|---|---|---|
| 8,380,637 B2 | 2/2013 | Levovitz |
| 8,423,466 B2 | 4/2013 | Lanc |
| 8,433,919 B2 | 4/2013 | Giobbi et al. |
| 8,538,881 B2 | 9/2013 | Weiss |
| 8,577,813 B2 | 11/2013 | Weiss |
| 8,594,632 B1 | 11/2013 | Azizi et al. |
| 8,613,052 B2 | 12/2013 | Weiss |
| 8,751,801 B2 | 6/2014 | Harris et al. |
| 8,814,046 B1* | 8/2014 | Wallner .............. G06K 7/08 235/449 |
| 8,838,502 B2 | 9/2014 | Niwa |
| 8,856,539 B2 | 10/2014 | Weiss |
| 9,100,826 B2 | 8/2015 | Weiss |
| 9,530,137 B2 | 12/2016 | Weiss |
| 9,531,696 B2 | 12/2016 | Weiss |
| 9,928,495 B2 | 3/2018 | Weiss |
| 9,947,000 B2 | 4/2018 | Weiss |
| 10,163,103 B2 | 12/2018 | Weiss |
| 2001/0029485 A1 | 10/2001 | Brody et al. |
| 2001/0032100 A1 | 10/2001 | Mahmud et al. |
| 2001/0044900 A1 | 11/2001 | Uchida |
| 2002/0046061 A1 | 4/2002 | Wright et al. |
| 2002/0090930 A1 | 7/2002 | Fujiwara et al. |
| 2002/0176610 A1 | 11/2002 | Okazaki et al. |
| 2002/0178364 A1 | 11/2002 | Weiss |
| 2002/0184500 A1 | 12/2002 | Maritzen et al. |
| 2002/0184538 A1 | 12/2002 | Sugimura et al. |
| 2002/0188574 A1 | 12/2002 | Niwa |
| 2002/0194499 A1 | 12/2002 | Audebert et al. |
| 2003/0014372 A1 | 1/2003 | Wheeler et al. |
| 2003/0028481 A1 | 2/2003 | Fliteroft et al. |
| 2003/0037233 A1 | 2/2003 | Pearson |
| 2003/0046540 A1 | 3/2003 | Nakamura et al. |
| 2003/0061171 A1 | 3/2003 | Gilbert et al. |
| 2003/0074568 A1 | 4/2003 | Kinsella et al. |
| 2003/0084332 A1 | 5/2003 | Krasinski et al. |
| 2003/0085808 A1 | 5/2003 | Goldberg |
| 2003/0115378 A1* | 6/2003 | Zondervan ............ G06F 8/34 719/328 |
| 2003/0115490 A1 | 6/2003 | Russo |
| 2003/0123713 A1 | 7/2003 | Geng |
| 2003/0129965 A1 | 7/2003 | Siegel |
| 2003/0139984 A1 | 7/2003 | Seigel |
| 2003/0163710 A1 | 8/2003 | Ortiz et al. |
| 2003/0219121 A1 | 11/2003 | van Someren |
| 2003/0226017 A1 | 12/2003 | Palekar et al. |
| 2003/0226041 A1 | 12/2003 | Palmer et al. |
| 2003/0229637 A1 | 12/2003 | Baxter et al. |
| 2004/0014423 A1 | 1/2004 | Croome et al. |
| 2004/0017934 A1 | 1/2004 | Kocher |
| 2004/0019564 A1 | 1/2004 | Goldthwaite et al. |
| 2004/0034771 A1 | 2/2004 | Edgett et al. |
| 2004/0044627 A1 | 3/2004 | Russell et al. |
| 2004/0059923 A1 | 3/2004 | ShamRao |
| 2004/0083170 A1 | 4/2004 | Barn et al. |
| 2004/0088369 A1 | 5/2004 | Yeager et al. |
| 2004/0107170 A1 | 6/2004 | Labrou et al. |
| 2004/0111625 A1 | 6/2004 | Duffy et al. |
| 2004/0117215 A1 | 6/2004 | Marchosky |
| 2004/0117302 A1 | 6/2004 | Weichert et al. |
| 2004/0131185 A1* | 7/2004 | Kakumer ............ H04W 12/06 380/247 |
| 2004/0133787 A1 | 7/2004 | Doughty et al. |
| 2004/0151351 A1 | 8/2004 | Ito |
| 2004/0181695 A1 | 9/2004 | Walker |
| 2004/0188519 A1 | 9/2004 | Cassone |
| 2004/0230536 A1 | 11/2004 | Fung et al. |
| 2004/0236632 A1 | 11/2004 | Maritzen et al. |
| 2004/0236699 A1 | 11/2004 | Beenau et al. |
| 2005/0001711 A1 | 1/2005 | Doughty et al. |
| 2005/0035847 A1 | 2/2005 | Bonalle et al. |
| 2005/0039027 A1 | 2/2005 | Shapiro |
| 2005/0071231 A1* | 3/2005 | Beenau .............. G06Q 20/04 705/16 |
| 2005/0097362 A1 | 5/2005 | Winget et al. |
| 2005/0113070 A1 | 5/2005 | Okabe |
| 2005/0130659 A1 | 6/2005 | Grech et al. |
| 2005/0187843 A1 | 8/2005 | Lapsley et al. |
| 2005/0187873 A1 | 8/2005 | Labrou et al. |
| 2005/0210270 A1 | 9/2005 | Rohatgi et al. |
| 2005/0235148 A1 | 10/2005 | Scheidt et al. |
| 2005/0238147 A1 | 10/2005 | Carro |
| 2005/0238208 A1 | 10/2005 | Sim |
| 2005/0268107 A1 | 12/2005 | Harris et al. |
| 2006/0000900 A1 | 1/2006 | Fernandes et al. |
| 2006/0016884 A1 | 1/2006 | Block et al. |
| 2006/0087999 A1 | 4/2006 | Gustave et al. |
| 2006/0104486 A1 | 5/2006 | Le Saint et al. |
| 2006/0117175 A1* | 6/2006 | Miura ............... G06F 21/445 713/155 |
| 2006/0122939 A1 | 6/2006 | Cohen et al. |
| 2006/0135127 A1 | 6/2006 | Aamio et al. |
| 2006/0165060 A1 | 7/2006 | Dua |
| 2006/0180660 A1 | 8/2006 | Gray |
| 2006/0191995 A1 | 8/2006 | Stewart et al. |
| 2006/0205388 A1 | 9/2006 | Semple et al. |
| 2006/0206724 A1 | 9/2006 | Schaufele et al. |
| 2006/0256961 A1 | 11/2006 | Brainard et al. |
| 2006/0276226 A1 | 12/2006 | Jiang |
| 2007/0005988 A1 | 1/2007 | Zhang |
| 2007/0016088 A1* | 1/2007 | Grant ................. A61B 5/117 600/509 |
| 2007/0040017 A1 | 2/2007 | Kozlay |
| 2007/0079136 A1 | 4/2007 | Vishik et al. |
| 2007/0118758 A1 | 5/2007 | Takahashi et al. |
| 2007/0124597 A1 | 5/2007 | Bedingfield |
| 2007/0124697 A1 | 5/2007 | Dongelmans |
| 2007/0131759 A1 | 6/2007 | Cox et al. |
| 2007/0136796 A1 | 6/2007 | Sanchez et al. |
| 2007/0140145 A1 | 6/2007 | Kumar et al. |
| 2007/0156436 A1* | 7/2007 | Fisher ................. G06Q 20/401 455/552.1 |
| 2007/0186105 A1 | 8/2007 | Bailey et al. |
| 2007/0186115 A1 | 8/2007 | Gao et al. |
| 2007/0197261 A1 | 8/2007 | Humbel |
| 2007/0198436 A1 | 8/2007 | Weiss |
| 2007/0245152 A1 | 10/2007 | Pizano et al. |
| 2007/0256120 A1 | 11/2007 | Shatzkamer et al. |
| 2007/0265984 A1 | 11/2007 | Santhana |
| 2007/0274242 A1 | 11/2007 | Lamacraft et al. |
| 2007/0288758 A1 | 12/2007 | Weiss |
| 2007/0289000 A1 | 12/2007 | Weiss |
| 2008/0005576 A1 | 1/2008 | Weiss |
| 2008/0021997 A1 | 1/2008 | Hinton |
| 2008/0040274 A1 | 2/2008 | Uzo |
| 2008/0127311 A1 | 5/2008 | Yasaki et al. |
| 2008/0212848 A1 | 9/2008 | Doyle |
| 2008/0275819 A1 | 11/2008 | Rifai |
| 2008/0289030 A1 | 11/2008 | Poplett |
| 2009/0083544 A1 | 3/2009 | Scholnick et al. |
| 2009/0097661 A1 | 4/2009 | Orsini et al. |
| 2009/0144814 A1 | 6/2009 | Sacco |
| 2009/0175507 A1 | 7/2009 | Schaffner |
| 2009/0179743 A1 | 7/2009 | Amtmann |
| 2009/0203355 A1 | 8/2009 | Clark |
| 2009/0247186 A1 | 10/2009 | Ji et al. |
| 2009/0287921 A1 | 11/2009 | Zhu et al. |
| 2009/0292641 A1 | 11/2009 | Weiss |
| 2009/0298514 A1 | 12/2009 | Ullah |
| 2010/0000455 A1 | 1/2010 | Harper |
| 2010/0046443 A1 | 2/2010 | Jia et al. |
| 2010/0095364 A1 | 4/2010 | Norgaard et al. |
| 2010/0241570 A1 | 9/2010 | Keresman, III et al. |
| 2011/0258120 A1 | 10/2011 | Weiss |
| 2011/0283337 A1 | 11/2011 | Schatzmayr |
| 2012/0004015 A1 | 1/2012 | Le Thierry D'Ennequin |
| 2012/0037479 A1 | 2/2012 | Lucchi et al. |
| 2012/0056681 A1 | 3/2012 | Lee |
| 2012/0130904 A1 | 5/2012 | Weiss |
| 2012/0150750 A1 | 6/2012 | Law et al. |
| 2012/0197808 A1 | 8/2012 | Niwa |
| 2012/0230555 A1 | 9/2012 | Miura et al. |
| 2012/0240195 A1 | 9/2012 | Weiss |
| 2013/0024374 A1 | 1/2013 | Weiss |

(56) References Cited

U.S. PATENT DOCUMENTS

| | | |
|---|---|---|
| 2013/0307670 A1 | 11/2013 | Ramaci |
| 2013/0318581 A1 | 11/2013 | Counterman |
| 2014/0096216 A1 | 4/2014 | Weiss |
| 2014/0101049 A1 | 4/2014 | Fernandes et al. |
| 2014/0149295 A1 | 5/2014 | Weiss |
| 2014/0196118 A1 | 7/2014 | Weiss |
| 2015/0046340 A1 | 2/2015 | Dimmick |
| 2016/0155121 A1 | 6/2016 | Weiss |

FOREIGN PATENT DOCUMENTS

| | | |
|---|---|---|
| EP | 1081632 A1 | 3/2001 |
| GB | 2382006 A | 5/2003 |
| WO | 1992007436 A1 | 4/1992 |
| WO | 1996036934 A1 | 11/1996 |
| WO | 0014648 A1 | 3/2000 |
| WO | 200106699 A2 | 1/2001 |
| WO | 0113275 A1 | 2/2001 |
| WO | 2001024123 A1 | 4/2001 |
| WO | 200163537 A1 | 8/2001 |
| WO | 2002014985 A2 | 2/2002 |
| WO | 2004051585 A2 | 6/2004 |
| WO | 2005/001751 A1 | 1/2005 |
| WO | 2010000455 A1 | 1/2010 |
| WO | 2012037479 A1 | 3/2012 |

OTHER PUBLICATIONS

"Bluetooth Technology FAQ", Mobileinfo.com, Jan. 21, 2001, all pages, http://www.web.archive.org/web/200101211551/http://www.mobileinfo.com/Bluetooth/FAQ.htm.
"FIPS PUB 46-3", National Institute of Science and Technology (NIST), Oct. 25, 1999, all pages.
"Information Security: Challenges in using biometrics", Sep. 9, 2003, all pages, <http://www.gao.gov/news.items/d031137t.pdf>.
"PGP: An introduction to cryptography", 2000, all pages.
"Single Sign On Authentication", Authentication World, Mar. 13, 2007, all pages, retrieved Jul. 9, 2010 via Wayback Machine, <http://web.archive.org/web/20070313200434/http://www.authenticationworld.com/Single-Sign-On-Authentication/>.
American Bankers Association, Financial Institution Key Management (Wholesale), ANSI X9.17 (1995).
Bruce Schneier, Applied Cryptography, 2d Ed (1996).
Complaint, *Universal Secure Registry LLC v. Apple Inc., Visa Inc., and Visa U.S.A., Inc.*, No. 17-585-VAC-MPT (D. Del.).
Curriculum Vitae of Dr. Douglas Justin Tygar.
Curriculum Vitae of Dr. Eric Cole.
Declaration of Dr. Eric Cole in Case IPR2018-00067.
Declaration of Dr. Justin Douglas Tygar in Case IPR2019-00727.
Declaration of Dr. Victor Shoup in Case CBM2018-00022.
Declaration of Dr. Victor Shoup in Case CBM2018-00023.
Declaration of Dr. Victor Shoup in Case CBM2018-00024.
Declaration of Dr. Victor Shoup in Case CBM2018-00025.
Declaration of Dr. Victor Shoup in Case CBM2018-00026.
Declaration of Dr. Victor Shoup in Case IPR2018-00808.
Declaration of Dr. Victor Shoup in Case IPR2018-00809.
Declaration of Dr. Victor Shoup in Case IPR2018-00810.
Declaration of Dr. Victor Shoup in Case IPR2018-00811.
Declaration of Dr. Victor Shoup in Case IPR2018-00812.
Declaration of Dr. Victor Shoup in Case IPR2018-00813.
Dynamic, Academic Press Dictionary of Science and Technology, 1992.
Dynamic, Random House Webster's Unabridged Dictionary, Second Edition, 2001.
Dynamic, The American Heritage Dictionary of the English Language, Third Edition, 1996.
File History for U.S. Pat. No. 8,577,813.
File History for U.S. Pat. No. 8,856,539.
Hungtington, "101 Things to know about single sign on", Authentication World, 2006, all pages, <http://www.authenticationworld.com/Single-Sign-On-Authentication/101ThingsToKnowAboutSingleSignOn.pdf>.
Intel Corp, Baca Jim S, Li Hong, Kohlenberg Tobias M, Stanasolovich David and Price Mark H File WIPO Patent Application for Method for Authentication Using Biometric Data for Mobile Device E-Commerce Transactions Jul. 2, 2013.
International Search Report and Written Opinion for International Application No. PCT/US2011/051966, 49 pages.
International Search Report from PCT Application No. PCT/US2007/004646 dated Nov. 27, 2007.
International Search Report from PCT Application No. PCT/US2007/070701 dated Mar. 11, 2008.
International Search Report from PCT Application No. PCT/US2009/035282 dated Jul. 10, 2009.
International Search Report from PCT/US2007/070701 datd Mar. 11, 2008.
Jin et al., Biohashing: two factor authentication featuring fingerprint data and tokenized random number, Pattern Recognition 37 (11), pp. 2245-2255 (2004).
Kessler, "An overview of cryptography", Aug. 22, 2002, all pages, retrieved via Wayback Machine on Jan. 19, 2010, http://www.garykessler.net/library/crypto.html.
Microsoft Computer Dictionary Fourth Edition Copyright 1999.
NIWA, "Method of Using Personal Device with Internal Biometric in Conducting Transactions Over a Network." U.S. Appl. No. 09/510,811 (Annotated).
Pabrai, "Biometrics for PC-user authentication: a primer", Access Controls & Security Systems, Feb. 1, 2001, all pages, <http://www.securitysolutions.com/mag/securit_biometrics_pcuser_authentication/index.html>.
Petition for Covered Business Method Review in U.S. Pat. No. 8,577,813 (CBM2019-00025) dated Dec. 20, 2018.
Petition for Covered Business Method Review in U.S. Pat. No. 8,577,813 (CBM2019-00026) dated Dec. 20, 2018.
Petition for Covered Business Method Review of U.S. Pat. No. 8,577,813 (CBM2018-00026) dated May 3, 2018.
Petition for Covered Business Method Review of U.S. Pat. No. 9,530,137 (CBM2018-00022) dated Apr. 3, 2018.
Petition for Covered Business Method Review of U.S. Pat. No. 8,577,813 (CBM2018-00024) dated May 3, 2018.
Petition for Covered Business Method Review of U.S. Pat. No. 8,577,813 (CBM2018-00025) dated May 3, 2018.
Petition for Covered Business Method Review of U.S. Pat. No. 8,856,539 (CBM2018-00023) dated Apr. 12, 2018.
Petition for Inter Partes Review in U.S. Pat. No. 9,100,826 (IPR2019-00175) dated Nov. 2, 2018.
Petition for Inter Partes Review in U.S. Pat. No. 9,100,826 (IPR2019-00176) dated Nov. 2, 2018.
Petition for Inter Partes Review of U.S. Pat. No. 8,577,813 (IPR2018-00067) dated Oct. 16, 2017.
Petition for Inter Partes Review of U.S. Pat. No. 9,100,826 (IPR2018-00810) dated Apr. 3, 2018.
Petition for Inter Partes Review of U.S. Pat. No. 9,100,826 (IPR2018-00813) dated Apr. 3, 2018.
Petition for Inter Partes Review of U.S. Pat. No. 9,530,137 (IPR2018-00808) dated Apr. 4, 2018.
Petition for Inter Partes Review of U.S. Pat. No. 9,530,137 (IPR2018-00809) dated Apr. 3, 2018.
Petition for Inter Partes Review of U.S. Pat. No. 9,530,137 (IPR2019-00174) dated Nov. 2, 2018.
Petition for Inter Partes Review of U.S. Pat. No. 8,856,539 (IPR2018-00811) dated Apr. 12, 2018.
Petition for Inter Partes Review of U.S. Pat. No. 8,856,539 (IPR2018-00812) dated Apr. 12, 2018.
Petition for Inter Partes Review of U.S. Pat. No. 8,856,539 (IPR2019-00727) dated Mar. 11, 2019.
Plantiff's Answering Brief in Opposition to Defendants' Motion to Dismiss Plaintiffs Complaint in C.A. No. 17-585, filed Sep. 29, 2017.
Treasury Board of Canada Secretariat, PKI for Beginners Glossary, http://www.tbs-sct.gc.ca/pki-icp/beginners/glossary-eng.asp.
U.S. Appl. No. 60/186,166.

(56) References Cited

OTHER PUBLICATIONS

Webster's New World Dictionary of Computer Terms Eighth Edition, Copyright 2000 (Date Stamped by Library of Congress Mar. 28, 2000).
Declaration of Dr. Patrick McDaniel in Support of Petition for Inter Partes Review of Claims 12-19 and 23-24 of U.S. Pat. No. 10,163,103 (IPR2020-01225) filed Aug. 7, 2020.
Petition for Inter Partes Review of Claims 12-19 and 23-24 of U.S. Pat. No. 10,163,103 (IPRP2020-01225) filed Aug. 7, 2020.
Declaration of Dr. Patrick McDaniel in Support of Petition for Inter Partes Review of Claims 1-4, 6-11 and 20-22 of U.S. Pat. No. 10,163,103 (IPR2020-01224) filed Aug. 7, 2020.
Petition for Inter Partes Review of Claims 1-4, 6-11 and 20-22 of U.S. Pat. No. 10,163,103 (IPR2020-01224) filed Aug. 7, 2020.
Complaint for Declaratory Judgment of Noninfringement—Case 1:20-cv-00907-CFC, filed Jul. 2, 2020, exhibit in Case IPR2020-01224 and Case IPR2020-01225 filed Aug. 7, 2020.
Memorandum Opinion—Case 1:17-cv-00585-CFC-SRF, filed Jun. 30, 2020, exhibit in Case IPR2020-01224 and Case IPR2020-01225 filed Aug. 7, 2020.
Order Granting Motion to Dismiss—Case 1:17-cv-00585-CFC-SRF, filed Jun. 30, 2020, exhibit in Case IPR2020-01224 and Case IPR2020-01225 filed Aug. 7, 2020.
U.S. Pat. No. 10,163,103 File History, exhibit in Case IPR2020-01224 and Case IPR2020-01225 filed Aug. 7, 2020.
Jain, A., et al., "Biometrics Personal Indentification in Networked Soceity," Kluwer Academic Publishers, (1999), exhibit in Case IPR2020-01224 and Case IPR2020-01225 filed Aug. 7, 2020.
Liu, S. et al., "A Practical Guide to Biometric Security Technology," IT Pro, IEEE (2001), exhibit in Case IPR2020-01224 and Case IPR2020-01225 filed Aug. 7, 2020.
Rifia, Z, et al., "Biometric Authentication Systems," Faculty of Informatics Masaryk University Report Series (2000), exhibit in Case IPR2020-01224 and Case IPR2020-01225 filed Aug. 7, 2020.
Complaint for Patent Infringement—Case 1:17-cv-00585-VAC-MPT, filed May 21, 2017, exhibit in Case IPR2020-01220, Case IPR2020-01221, Case IPR2020-01222, and Case IPR2020-01223 filed Jul. 20, 2020.
U.S. Pat. No. 9,947,000 File History, exhibit in Case IPR2020-01220 and Case IPR2020-01221 filed Jul. 20, 2020.
U.S. Pat. No. 9,928,495 File History, exhibit in Case IPR2020-01222 and Case IPR2020-01223 filed Jul. 20, 2020.
Petition for Inter Partes Review of Claims 1-21 of U.S. Pat. No. 9,947,000 (IPR2020-01220) filed Jul. 20, 2020.
Declaration of Dr. Patrick McDaniel in Support of Petition for Inter Partes Review of Claims 1-21 of U.S. Pat. No. 3,947,000 (IPR2020-01220) filed Jul. 20, 2020.
Petition for Inter Partes Review of Claims 22-28 of U.S. Pat. No. 9,947,000 (IPR2020-01221) filed Jul. 20, 2020.
Declaration of Dr. Patrick McDaniel in Support of Petition for Inter Partes Review of Claims 22-28 of U.S. Pat. No. 3,947,000 (IPR2020-01221) filed Jul. 20, 2020.
Declaration of Dr. Patrick McDaniel in Support of Petition for Inter Partes Review of Claims 1-21 of U.S. Pat. No. 3,928,495 (IPR2020-01222) filed Jul. 20, 2020.
Petition for Inter Partes Review of Claims 1-21 U.S. Pat. No. 9,928,495 (IPR2020-01222) filed Jul. 20, 2020.
Petition for Inter Partes Review of Claims 22-28 of U.S. Pat. No. 9,928,495 (IPR2020-01223) filed Jul. 20, 2020.
Declaration of Dr. Patrick McDaniel in Support of Petition for Inter Partes Review of Claims 22-28 of U.S. Pat. No. 9,928,495 (IPR2020-01223) filed Jul. 20, 2020.

\* cited by examiner

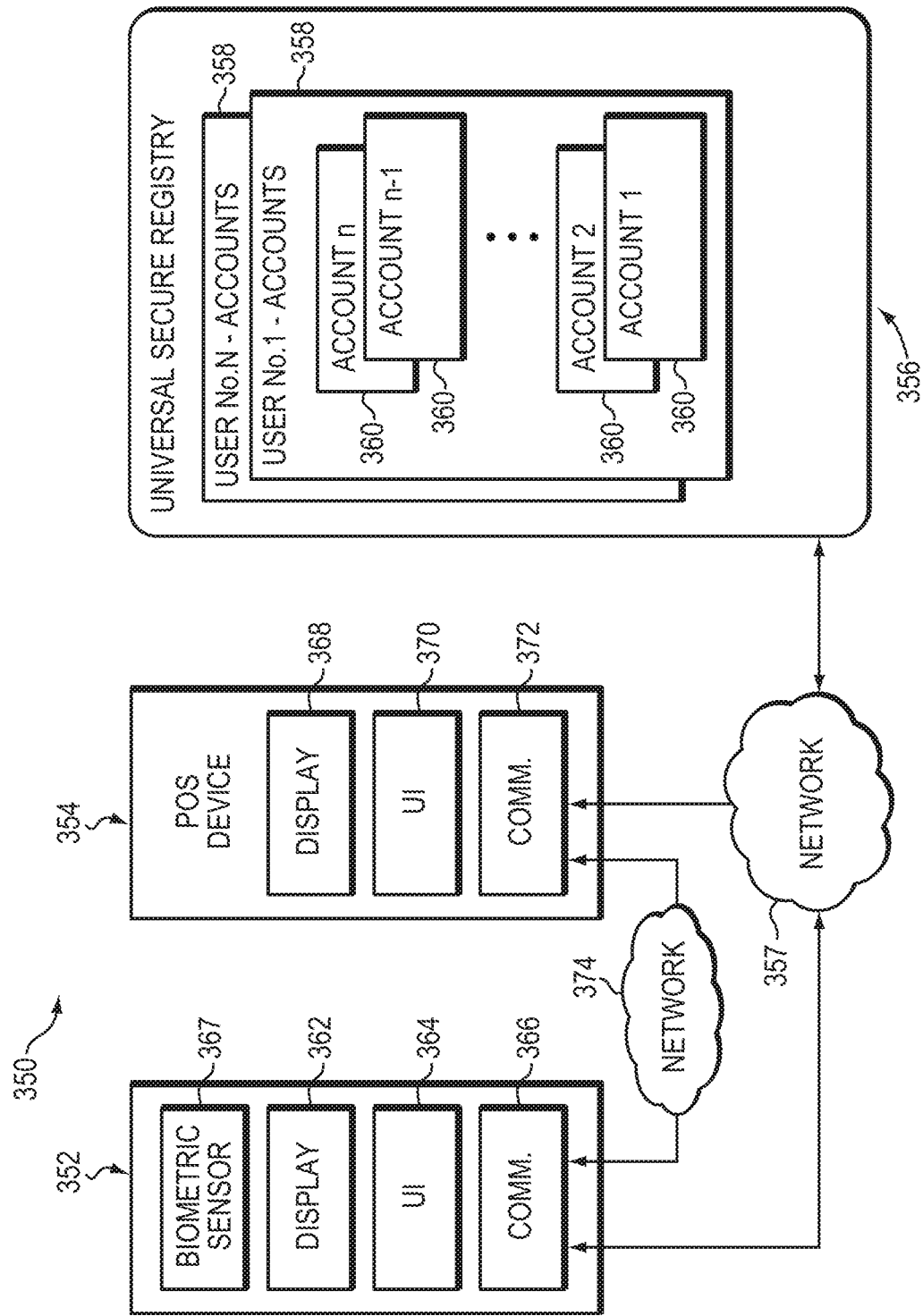

UNIVERSAL SECURE REGISTRY

CROSS-REFERENCE TO RELATED APPLICATIONS

This application is a continuation of and also claims priority under 35 U.S.C. § 120 to co-pending U.S. patent application Ser. No. 16/590,872 filed Oct. 2, 2019, entitled "UNIVERSAL SECURE REGISTRY." U.S. patent application Ser. No. 16/590,872 is a continuation of and also claims priority under 35 U.S.C. § 120 to U.S. patent application Ser. No. 14/071,126 filed Nov. 4, 2013, entitled "UNIVERSAL SECURE REGISTRY." U.S. patent application Ser. No. 14/071,126 is a continuation of and also claims priority under 35 U.S.C. § 120 to U.S. patent application Ser. No. 13/237,184 filed Sep. 20, 2011, now U.S. Pat. No. 8,577,813, entitled "UNIVERSAL SECURE REGISTRY."

U.S. patent application Ser. No. 13/237,184 is a continuation-in-part of, and also claims priority under 35 U.S.C. § 120 to, U.S. patent application Ser. No. 13/168,556, filed on Jun. 24, 2011, now U.S. Pat. No. 8,271,397. U.S. patent application Ser. No. 13/237,184 is also a continuation of, and also claims priority under 35 U.S.C. § 120 to, U.S. patent application Ser. No. 12/393,586 filed Feb. 26, 2009, now U.S. Pat. No. 8,234,220 entitled "UNIVERSAL SECURE REGISTRY."

U.S. patent application Ser. No. 12/393,586 is a continuation-in-part of each of U.S. patent application Ser. No. 11/760,732 filed Jun. 8, 2007, now U.S. Pat. No. 7,809,651, entitled "UNIVERSAL SECURE REGISTRY"; U.S. patent application Ser. No. 11/760,729 filed Jun. 8, 2007, now U.S. Pat. No. 7,805,372, entitled "UNIVERSAL SECURE REGISTRY"; and U.S. patent application Ser. No. 11/677,490 filed Feb. 21, 2007, now U.S. Pat. No. 8,001,055 entitled "METHOD, SYSTEM AND APPARATUS FOR SECURE ACCESS PAYMENT AND IDENTIFICATION."

U.S. patent application Ser. No. 13/168,556 filed on Jun. 24, 2011, is a continuation of U.S. patent application Ser. No. 11/677,490 filed Feb. 21, 2007, now U.S. Pat. No. 8,001,055.

U.S. application Ser. No. 11/760,732 is a continuation of U.S. application Ser. No. 11/677,490, now U.S. Pat. No. 8,001,055, and U.S. patent application Ser. No. 11/760,729 is a continuation of U.S. application Ser. No. 11/677,490, now U.S. Pat. No. 8,001,055.

Each of U.S. application Ser. Nos. 11/760,732, 11/760,729, and 11/677,490 claims priority under 35 U.S.C. § 119(e) to U.S. Provisional Application Nos. 60/812,279 filed on Jun. 9, 2006 entitled "UNIVERSAL SECURE REGISTRY," and 60/859,235 filed on Nov. 15, 2006 entitled "UNIVERSAL SECURE REGISTRY."

U.S. application Ser. No. 11/677,490 filed Feb. 21, 2007, also claims priority under 35 U.S.C. § 119(e) to U.S. Provisional Application No. 60/775,046 filed on Feb. 21, 2006 entitled "METHOD AND APPARATUS FOR EMULATING A MAGNETIC STRIPE READABLE CARD."

U.S. patent application Ser. No. 12/393,586 filed Feb. 26, 2009, entitled "UNIVERSAL SECURE REGISTRY," claims priority under 35 U.S.C. § 119(e) to U.S. Provisional Application Ser. No. 61/031,529, entitled "UNIVERSAL SECURE REGISTRY," filed on Feb. 26, 2008.

Each of the above-identified applications is hereby incorporated herein by reference in its entirety.

BACKGROUND OF INVENTION

1. Field of Invention

Embodiments of the invention generally relate to systems, methods, and apparatus for authenticating identity or verifying the identity of individuals and other entities seeking access to certain privileges and for selectively granting privileges and providing other services in response to such identifications/verifications. In addition, embodiments of the invention relate generally to systems and methods for obtaining information from and/or transmitting information to a user device and, in particular, to systems, methods, and apparatus that provide for contactless information transmission.

2. Discussion of Related Art

Control of access to secure systems presents a problem related to the identification of a person. An individual may be provided access to the secure system after their identity is authorized. Generally, access control to secure computer networks is presently provided by an authentication scheme implemented, at least partly, in software located on a device being employed to access the secure computer network and on a server within the secure computer network. For example, if a corporation chooses to provide access control for their computer network, they may purchase authentication software that includes server-side software installed on a server in their computer system and corresponding client-side software that is installed on the devices that are used by employees to access the system. The devices may include desktop computers, laptop computers, and handheld computers (e.g., PDAs and the like).

In practice, the preceding approach has a number of disadvantages including both the difficulty and cost of maintaining the authentication system and the difficulty and cost of maintaining the security of the authentication system. More specifically, the software resides in the corporation's computers where it may be subject to tampering/unauthorized use by company employees. That is, the information technology team that manages the authentication system has access to the private keys associated with each of the authorized users. As a result, these individuals have an opportunity to compromise the security of the system. Further, any modification and/or upgrade to the authentication system software is likely to require an update to at least the server-side software and may also require an update of the software located on each user/client device. In addition, where the company's computer systems are geographically distributed, software upgrades/updates may be required on a plurality of geographically distributed servers.

There is also a need, especially in this post September 11 environment, for secure and valid identification of an individual before allowing the individual access to highly secure areas. For example, an FBI agent or an air marshal may need to identify themselves to airport security or a gate agent, without compromising security. Typically such identification may comprise the air marshal or FBI agent showing identification indicia to appropriate personnel. However, there are inherent flaws in this process that allow for security to be compromised, including falsification of identification information and failure of the airport security or other personnel to recognize the situation. Of course this process could be automated, for example, by equipping airport personnel or security with access to a database and requiring the FBI agent or air marshal to appropriately identify themselves to the database, for example, by again providing identification which airport personnel can then enter into the database to verify the identity of the person seeking access to a secure area. However, this process also has the inherent flaws in it as described above. In addition, there may be times when airport security or personnel may not be able to communicate with the database to check the identity of the person seeking access, for example, when they are not near a computer terminal with access to a database or are carrying a hand-held device that does not have an appropriate wireless signal to access the database. In addition, there is a need to ensure that if such a hand-held device ends up the wrong hands, that security is not compromised.

Further, both commercial (e.g., banking networks) and non-commercial (e.g., security systems) information systems often rely on magnetic card readers to collect information specific to a user (e.g., a security code, a credit card number, etc.) from a user device (e.g., a transaction card). Credit card purchases made in person provide an example of the most common transaction-type that relies on a user device, the credit or debit card, which is read by a magnetic card reader. User devices that rely on magnetic-stripe based technology magnetically store information (e.g., binary information) in the magnetic stripe. The magnetic stripe reader provides an interface to a larger computerized network that receives the user's information to determine, for example, whether to authorize a transaction, to allow the user access to a secure area, etc.

Recently, such devices have seen technological advances that increase their capabilities and improve their security. For example, such devices may now include embedded processors, integral biometric sensors that sense one or more biometric feature (e.g., a fingerprint) of the user, and magnetic stripe emulators. As one result, such devices may provide greater security by dynamically generating the necessary information, for example, generating the credit card number at the time of a transaction. Improved security can also be provided by such devices because more sophisticated authentication schemes can be implemented with the devices.

In addition, user devices such as transaction cards may now also provide for one or more modes of information transmission other than transmission via a magnetic stripe/card reader combination. For example, user devices that may transmit information optically or via radio frequency ("RF") signal transmission to a compatible system interface are now available. Further, the architecture of a user device that includes a processor is generally compatible with both the improved security features described above and the contactless transmission modes such as optical and RF signal transmission. As a result of the improved security and greater functionality of some current user devices, there is a desire to replace magnetic-stripe based user devices with devices that include forms of information transmission other than the reading of a magnetic-stripe.

There is, however, a substantial installed base of interfaces (for example, at points of sale, at automatic teller machines ("ATM"), and the like) that include magnetic card readers which are not equipped to receive information from a user device in any other format other than from a magnetic stripe. As a result of the cost to replace or retrofit the installed base, efforts to more-widely introduce user devices that do not employ magnetic stripe devices have not been developed. Because of the potential to substantially reduce fraud, however, the further implementation of such devices is of great interest to financial institutions among others. RF devices that transmit information wirelessly are expected to become much more prevalent and at some point, the predominant form of information transmission for user authentication based on a hand-held device, for example, credit card, debit card, drivers license, passport, social security card, personal identification, etc. Thus, new and improved methods for transitioning from a purely magnetic based form of communication to a wireless form of communication are desired.

One current approach that is intended to "transform" a smart card for use with a magnetic stripe card reader employs a "bridge" device. The bridge device requires that the smart card be inserted within it. The bridge device includes a slot for receiving the smart card, a key pad whereby the user may enter information (e.g., a PIN number), and a credit card sized extension member. Operation of the bridge device requires that the smart card be inserted within it and that an electrical contact surface of the smart card engage a similar surface within the bridge device before the bridge device (i.e., the extension member) can be used with a magnetic card reader. Thus, the contactless nature of more advanced information transmission systems is lost with the bridge device because it does not support wireless signal transmission.

Accordingly, there is a desire for one or more devices, systems and methods for accomplishing any of the herein mentioned objectives.

SUMMARY OF INVENTION

There is thus a need for an identification system that will enable a person to be accurately identified ("identification" sometimes being used hereinafter to mean either identified or verified) and/or authenticated without compromising security, to gain access to secure systems and/or areas. Likewise, there is a need for an identification system that will enable a person to be identified universally without requiring the person to carry multiple forms of identification.

Accordingly, this invention relates, in one embodiment, to an information system that may be used as a universal identification system and/or used to selectively provide information about a person to authorized users. Transactions to and from a secure database may take place using a public key/private key security system to enable users of the system and the system itself to encrypt transaction information during the transactions. Additionally, the private key/public key security system may be used to allow users to validate their identity. For example, in one embodiment, a smart card such as the SecurID™ card from RSA Security, Inc. may be provided with the user's private key and the USR system's public key to enable the card to encrypt messages being sent to the USR system and to decrypt messages from the USR system 10.

The system or database of the invention may be used to identify the person in many situations, and thus may take the place of multiple conventional forms of identification. Additionally, the system may enable the user's identity to be confirmed or verified without providing any identifying information about the person to the entity requiring identification. This can be advantageous where the person suspects that providing identifying information may subject the identifying information to usurpation.

Access to the system may be by smart card, such as a SecurID™ card, or any other secure access device. The technology enabling the user to present their identity information may be physically embodied as a separate identification device such as a smart ID card, or may be incorporated into another electronic device, such as a cell phone, pager, wrist watch, computer, personal digital assistant such as a Palm Pilot™, key fob, or other commonly available electronic device. The identity of the user possessing the identifying device may be verified at the point of use via any combination of a memorized PIN number or code, biometric identification such as a fingerprint, voice print, signature, iris or facial scan, or DNA analysis, or any other method of identifying the person possessing the device. If desired, the identifying device may also be provided with a picture of the person authorized to use the device to enhance security.

According to one embodiment of the invention, a method of controlling access to a plurality of secure computer networks using a secure registry system located remotely from the secure computer networks is disclosed. The secure registry system includes a database containing selected data of a plurality of users each authorized to access at least one of the plurality of secure computer networks. The method comprises acts of receiving authentication information from an entity at a secure computer network, communicating the authentication information to the secure registry system, and validating the authentication information at the secure registry system. The method also includes receiving from the secure registry system an indication of whether the entity is authorized to access the secure computer network, granting the entity access to the secure computer network when the authentication information of the entity corresponds to one of the plurality of users, and denying the entity access to the secure computer network when the authentication information of the user does not correspond to one of the plurality of users.

Another embodiment of the invention comprises a method of controlling access to a secure computer network using a secure registry system. The secure registry system includes a database containing selected data of a plurality of users authorized to access the secure computer network and selected data identifying the secure computer network. The method comprises receiving an access request including authentication information and a computer network ID from an entity, determining whether the authentication information is valid for any of the plurality of users, accessing data when the authentication information of the entity is valid for one of the plurality of users to determine whether the entity is authorized to access the computer network identified by the computer network ID, and allowing the entity to access the secure computer network when the authentication information of the entity is valid for one of the plurality of users authorized to access the computer network identified by the computer network ID.

Another embodiment of the invention comprises a method of authenticating an identity of a first entity. The method comprises the acts of wirelessly transmitting from a first device, first encrypted authentication information of the first entity, receiving with a second device the wirelessly transmitted first encrypted authentication information, decrypting with the second device, the first wirelessly encrypted authentication information to provide the first authentication information of the first entity to the second device; and authenticating the identity of the first entity based upon the first authentication information; and acting based on the assessed identity of the first entity.

Another embodiment of the invention comprises a system for authenticating an identity of a first entity, comprising a first wireless device comprising a first wireless transmitter and receiver configured to transmit a first wireless signal including first encrypted authentication information, a first processor configured to compare stored biometric data with detected biometric data of the first entity and configured to enable or disable use of the first device based on a result of the comparison, and configured to encrypt first authentication information with a first private key of the first entity into the first encrypted authentication information, a first biometric detector for detecting biometric data of the first entity, and a first memory for storing biometric data of the first entity, a private key of the first entity authorized to use the first device, and the first authentication information.

According to some embodiments, the system further comprises a second wireless device comprising a second wireless transmitter and receiver configured to receive the first wireless signal and to process the first wireless signal, a second processor configured to compare detected biometric data of a second entity with stored biometric data and configured to enable or disable use of the second device based upon a result of the comparison, and configured to decrypt the first authentication information received in the first wireless signal, a biometric detector for detecting biometric data of a second entity, and a second memory storing biometric data of the second entity and a plurality of public keys of a plurality of first entities.

Another embodiment of the invention provides a first wireless device comprising a processor configured to enable operation of the first wireless device if it receives an enablement signal validating first biometric information of a first entity and configured to generate a non-predictable signal from the biometric information, a first wireless transmitter and receiver configured to transmit a first wireless signal including first encrypted biometric information of the first entity and to receive the enablement signal, and a first biometric detector for detecting the first biometric information of the first entity.

In one aspect of the invention, a device converts a wireless transaction device to a magnetic-stripe emulator device. In one embodiment, the device includes a wireless signal receiver that is configured to receive a wireless signal and provide information from the wireless signal. In addition, the device may include a magnetic-stripe emulator which is communicatively coupled to the wireless signal receiver and adapted to provide a time-varying signal which emulates data provided by a magnetic-stripe card to a magnetic card reader in response to receiving the information from the wireless signal. In one embodiment, the device includes a processor communicatively coupled to the wireless signal receiver and to the magnetic-stripe emulator. The device may also include an LED. In a version of this embodiment, the processor is configured to control the LED to indicate that the device is properly aligned with the magnetic card reader. In another embodiment, the device includes an output device that can provide information to a network or to a network device. In a version of this embodiment, the output device is a wireless transmitter device.

Further embodiments of the invention may include additional features, for example, in one embodiment the output device is a data port to which the device can provide data to a network or to a network device. In a version of this embodiment, the data port is also configured to receive data from the network or the network's device. In a further embodiment, the device is configured to communicate with the magnetic card reader via the data port.

In a further embodiment, the wireless receiver and/or processors configure, decrypt and encrypt the wireless signal. In a further embodiment, the processor is configured to determine whether a user is authorized to provide the information contained within the wireless signal from data within the wireless signal. In a version of this embodiment, the data contained within the wireless signal includes user ID information. In yet another embodiment, the data contained within the wireless signal includes biometric information of the user.

According to another aspect, the invention provides a system for validating an identity of a user to enable or prevent an occurrence of an event. In one embodiment, the system includes a first device including a wireless transmitter which is configured to transmit validation information, a second device including a wireless receiver, where the second device is configured to receive the validation information and further transmit the validation information; and a secure system in communication with the second device. According to one embodiment, the secure system includes a database. In a further embodiment, the secure system is configured to receive the validation information transmitted from the second device, and to transmit additional information to the second device following a receipt of the validation information to assist the second device in either enabling or preventing the occurrence of the event. In various embodiments, the event that is enabled or prevented may be a transaction (e.g., a financial transaction), access control (e.g., physical or electronic access) or other action that is either enabled or prevented.

According to a further aspect, the invention provides a method employing a system to validate an identity of a user to enable or prevent an occurrence of an event. In one embodiment, the system includes a first device, a second device and a secure system including a database. According to one embodiment, the method includes acts of receiving at the second device validation information wirelessly transmitted from the first device, communicating the validation information from the second device to the secure system, and receiving at the second device additional information from the secure system. In a further embodiment, the additional information assists the second device in either enabling or preventing the occurrence of the event. In various embodiments, the event that is enabled or prevented may be a transaction (e.g., a financial transaction), access control (e.g., physical or electronic access) or other action that is either enabled or prevented.

In still another aspect, a user device is configured to allow a user to select any one of a plurality of accounts associated with the user to employ in a financial transaction. In one embodiment, the user device includes a biometric sensor configured to receive a biometric input provided by the user, a user interface configured to receive a user input including secret information known to the user and identifying information concerning an account selected by the user from the plurality of accounts. In a further embodiment, the user device includes a communication link configured to communicate with a secure registry, and a processor coupled to the biometric sensor to receive information concerning the biometric input, the user interface, and the communication link. According to one embodiment, the processor is configured to generate a non-predictable value and to generate encrypted authentication information from the non-predictable value, the identifying information, and at least one of the information concerning the biometric input and the secret information, and to communicate the encrypted authentication information via the communication link to the secure registry.

In accordance with another aspect, a method of generating authentication information includes acts of authenticating an identity of a user to a device based on at least one of biometric data received by the device from the user and secret information known to the user and provided to the device. The method can also include the generation of a non-predictable value with the device. The method can further include acts of receiving identifying information from the user concerning a selected one of a plurality of user accounts and generating encrypted authentication information from the non-predictable value, the identifying information, and at least one of the biometric data and the secret information. In a further embodiment, the device can generate encrypted authentication information from each of the non-predictable value, the biometric data, the secret information, and the identifying information.

According to a still further aspect, a method of controlling access to a plurality of accounts is provided where the method includes acts of generating, with a device, encrypted authentication information from a non-predictable value generated by the device, identifying information concerning an account selected by a user of the device from among a plurality of accounts associated with the user, and at least one of a biometric of the user received by the device and secret information provided to the device by the user, communicating the encrypted authentication information from the device to a secure registry via a point-of-sale (POS) device to authenticate or not authenticate the device with the secure registry, authorizing the POS device to initiate a financial transaction involving a transfer of funds to or from the account selected by the user when the encrypted authentication information is successfully authenticated, and denying the POS device from initiation of the financial transaction involving a transfer of funds to or from the account selected by the user when the encrypted authentication information is not successfully authenticated.

According to an aspect of the disclosure, an electronic ID device is configured to allow a user to select an account associated with the user to employ in a transaction, the electronic ID device comprising a biometric sensor configured to receive a biometric input provided by the user, a user interface configured to receive a user input, the user input including secret information known to the user, and selection information concerning an account selected by the user from one or more accounts associated with the user, a communication interface configured to communicate with a secure registry, wherein the communication interface includes a near field communication (NFC) transceiver, and a processor coupled to the biometric sensor to receive information concerning the biometric input, wherein the processor is programmed to activate the electronic ID device in response to a successful authentication of the user's identity, wherein authentication of the user's identity is based on at least one of the biometric input and the secret information, generate a one-time non-predictable value, obtain a public identifier that corresponds to private account information of the selected user account, wherein the public identifier does not contain any private account information of the selected user account, generate authentication information using the one-time non-predictable value and the public identifier, encrypt the authentication information, and wirelessly communicate the encrypted authentication information to a requesting or receiving device via an authentication signal generated by the communication interface, the authentication signal comprising an NFC signal, such that the secure registry receives a transaction request and at least a portion of the encrypted authentication information from the requesting or receiving device, wherein the transaction request involves the selected user account, verifies the encrypted authentication information, uses the public identifier from the encrypted authentication information to acquire the private account information of the selected user account, and generates an enablement signal to enable the transaction request without transmitting the private account information.

In various examples, the communication interface is configured to communicate with the secure registry either directly or via an intermediate device. In some examples, the public identifier does not contain any compromisable account information. In at least one example, the processor is further programmed to wirelessly communicate the encrypted authentication information to the requesting or receiving device via an induced signal generated by the communication interface. In various examples, the NFC signal is generated by NFC transceiver of the communication interface. In some examples, the communication interface further includes a magnetic stripe emulator.

In at least one example, the processor is further programmed to wirelessly communicate encrypted authentication information to the requesting or receiving device via a time-varying signal which emulates data provided by a magnetic-stripe card to a magnetic card reader, the time varying signal generated by the magnetic stripe emulator of the communication interface. In various examples, in activating the electronic ID device, the processor is further programmed to render stored data legible. In at least one example, the encrypted authentication information is one-time encrypted authentication information. In some examples, the communication interface is configured to communicate the encrypted authentication information to the secure registry, where the secure registry comprises a secure token database storing one or more tokens associated with the authentication information.

According to an aspect of the disclosure, an electronic ID device is configured to allow a user to select an account associated with the user to employ in a transaction, the electronic ID device comprising a biometric sensor configured to receive a biometric input provided by the user, a user interface configured to receive a user input, the user input including secret information known to the user, and selection information concerning an account selected by the user from one or more accounts associated with the user, a communication interface configured to communicate with a secure registry, wherein the communication interface includes a magnetic stripe emulator, and a processor coupled to the biometric sensor to receive information concerning the biometric input, wherein the processor is programmed to activate the electronic ID device in response to a successful authentication of the user's identity, wherein authentication of the user's identity is based on at least one of the biometric input and the secret information, generate a one-time non-predictable value, obtain a public identifier that corresponds to private account information of the selected user account, wherein the public identifier does not contain any private account information of the selected user account, generate authentication information using the one-time non-predictable value and the public identifier, encrypt the authentication information, and wirelessly communicate the encrypted authentication information to a requesting or receiving device via an authentication signal generated by the communication interface, the authentication signal comprising a time-varying signal which emulates data provided by a magnetic-stripe card to a magnetic card reader, such that the secure registry receives a transaction request and at least a portion of the encrypted authentication information from the requesting or receiving device, wherein the transaction request involves the selected user account, verifies the encrypted authentication information, uses the public identifier from the encrypted authentication information to acquire the private account information of the selected user account, and generates an enablement signal to enable the transaction request without transmitting the private account information.

In various examples, the communication interface is configured to communicate with the secure registry either directly or via an intermediate device. In at least one example, the public identifier does not contain any compromisable account information. In some examples, the processor is further programmed to wirelessly communicate the encrypted authentication information to the requesting or receiving device via an induced signal generated by the communication interface. In various examples, the time varying signal is generated by the magnetic stripe emulator of the communication interface. In some examples, the processor is further programmed to wirelessly communicate encrypted authentication information to the requesting or receiving device via a near field signal generated by the communication interface.

In at least one example, the processor is further programmed to wirelessly communicate encrypted authentication information to the requesting or receiving device via a Bluetooth™ wireless technology standard signal. In various examples, in activating the electronic ID device, the processor is further programmed to render stored data legible. In some examples, the encrypted authentication information is one-time encrypted authentication information. In at least one example, the communication interface is configured to communicate the encrypted authentication information to the secure registry, where the secure registry comprises a secure token database storing one or more tokens associated with the authentication information.

According to an aspect of the disclosure, an electronic ID device is configured to allow a user to select an account associated with the user to employ in a transaction, the electronic ID device comprising a biometric sensor configured to receive a biometric input provided by the user, a user interface configured to receive a user input, the user input including secret information known to the user, and selection information concerning an account selected by the user from one or more accounts associated with the user, a communication interface configured to communicate with a secure registry, wherein the communication interface includes a Bluetooth™ or Bluetooth™ Low Energy transceiver, and a processor coupled to the biometric sensor to receive information concerning the biometric input, wherein the processor is programmed to activate the electronic ID device in response to a successful authentication of the user's identity, wherein authentication of the user's identity is based on at least one of the biometric input and the secret information, generate a one-time non-predictable value, obtain a public identifier that corresponds to private account information of the selected user account, wherein the public identifier does not contain any private account information of the selected user account, generate authentication information using the one-time non-predictable value and the public identifier, encrypt the authentication information, and wirelessly communicate the encrypted authentication information to a requesting or receiving device via an authentication signal generated by the communication interface, the authentication signal comprising a Bluetooth™ or Bluetooth™ Low Energy signal, such that the secure registry receives a transaction request and at least a portion of the encrypted authentication information from the requesting or receiving device, wherein the transaction request involves the selected user account, verifies the encrypted authentication information, uses the public identifier from the encrypted authentication information to acquire the private account information of the selected user account, and generates an enablement signal to enable the transaction request without transmitting the private account information.

In various examples, the communication interface is configured to communicate with the secure registry either directly or via an intermediate device. In at least one example, the public identifier does not contain any compromisable account information. In some examples, the processor is further programmed to wirelessly communicate the encrypted authentication information to the requesting or receiving device via an induced signal generated by the communication interface. In various examples, the Bluetooth™ or Bluetooth™ Low Energy signal is generated, respectively, by the Bluetooth™ or Bluetooth™ Low Energy transceiver of the communication interface.

In at least one example, the communication interface further includes one or more of a magnetic stripe emulator, and a near field communication (NFC) transceiver. In some examples, the processor is further programmed to wirelessly communicate encrypted authentication information to the requesting or receiving device via one or more of a time-varying signal which emulates data provided by a magnetic-stripe card to a magnetic card reader, the time varying signal generated by the magnetic stripe emulator of the communication interface, and an NFC signal generated by the NFC transceiver of the communication interface.

In various examples, in activating the electronic ID device, the processor is further programmed to render stored data legible. In some examples, the encrypted authentication information is one-time encrypted authentication information. In at least one example, the communication interface is configured to communicate the encrypted authentication information to the secure registry, where the secure registry comprises a secure token database storing one or more tokens associated with the authentication information.

According to one aspect, an electronic ID device configured to allow a user to select an account associated with the user to employ in a transaction is provided, the electronic ID device comprising a biometric sensor configured to receive a biometric input provided by the user, a user interface configured to receive a user input, the user input including secret information known to the user, and selection information concerning an account selected by the user from one or more accounts associated with the user, a communication interface configured to communicate with a secure registry, and a processor coupled to the biometric sensor to receive information concerning the biometric input, wherein the processor is programmed to activate transaction software of the electronic ID device in response to a successful authentication of a user's identity, wherein authentication of the user's identity is based on at least one of the biometric input and the secret information, generate a one-time non-predictable value, obtain a public identifier that corresponds to private account information of the selected user account, wherein the public identifier does not contain any private account information of the selected user account, generate authentication information from the one-time non-predictable value and the public identifier, encrypt the authentication information, and wirelessly communicate the encrypted authentication information to a requesting or receiving device via an authentication signal generated by the communication interface, such that the secure registry receives a transaction request and at least a portion of the encrypted authentication information from the requesting or receiving device, wherein the transaction request involves the selected user account, decrypts the encrypted authentication information, verifies the decrypted authentication information without using the private account information, uses the public identifier from the encrypted authentication information to acquire the private account information of the selected user account, and generates an enablement signal to enable the transaction request without transmitting the private account information.

In some examples, the communication interface is configured to communicate with the secure registry either directly or via an intermediate device. In various examples, the processor is further programmed to wirelessly communicate the encrypted authentication information to the requesting or receiving device via an induced signal generated by the communication interface. In at least one example, the communication interface includes a magnetic stripe emulator. In some examples, the processor is further programmed to wirelessly communicate the encrypted authentication information to the requesting or receiving device via a time-varying signal which emulates data provided by a magnetic-stripe card to a magnetic card reader, and the time-varying signal is generated by the magnetic stripe emulator of the communication interface.

In various examples, the processor is further programmed to wirelessly communicate the encrypted authentication information to the requesting or receiving device via a near field signal generated by the communication interface. In at least one example, the communication interface includes a near field communication (NFC) transceiver, and the authentication signal generated by the communication interface is an NFC signal. In some examples, the NFC signal is generated by the NFC transceiver of the communication interface, and the processor is further programmed to wirelessly communicate the encrypted authentication information to the requesting or receiving device via the NFC signal, the requesting or receiving device located within the same local area as the NFC transceiver such that the NFC signal is transmitted directly between the NFC transceiver and the requesting or receiving device.

In various examples, the processor is further programmed to wirelessly communicate the encrypted authentication information to the requesting or receiving device via a Wi-Fi™ radio technology signal generated by the communication interface. In some examples, the processor is further programmed to wirelessly communicate the encrypted authentication information to the requesting or receiving device via a Bluetooth™ wireless technology standard signal. In at least one example, the processor is further programmed to wirelessly communicate the encrypted authentication information to the requesting or receiving device via a Bluetooth™ Low Energy wireless technology standard signal. In various examples, in activating the transaction software of electronic ID device, the processor is further programmed to render stored data legible.

In some examples, the encrypted authentication information is one-time encrypted authentication information. In at least one example, the communication interface is configured to communicate the encrypted authentication information to the secure registry, where the secure registry comprises a secure token database storing one or more tokens associated with the authentication information. In various examples, the processor is further programmed to deactivate features of the electronic ID device without generating the authentication information where authentication based on at least one of the biometric input and the secret information is unsuccessful. In some examples, deactivating the features of the electronic ID device initiates a lock-out period. In at least one example, deactivating the features of the electronic ID device includes deleting information present in the electronic ID device that is used to generate the authentication information.

BRIEF DESCRIPTION OF DRAWINGS

This invention is pointed out with particularity in the appended claims. The above and further advantages of this invention may be better understood by referring to the following description when taken in conjunction with the accompanying drawings. The accompanying drawings are not intended to be drawn to scale. In the drawings, each identical or nearly identical component that is illustrated in various figures is represented by a like numeral. For purposes of clarity, not every component may be labeled in every thawing. In the drawings:

FIG. 31 illustrates a further embodiment of a system that employs the USR system.

DETAILED DESCRIPTION

Figure 1:
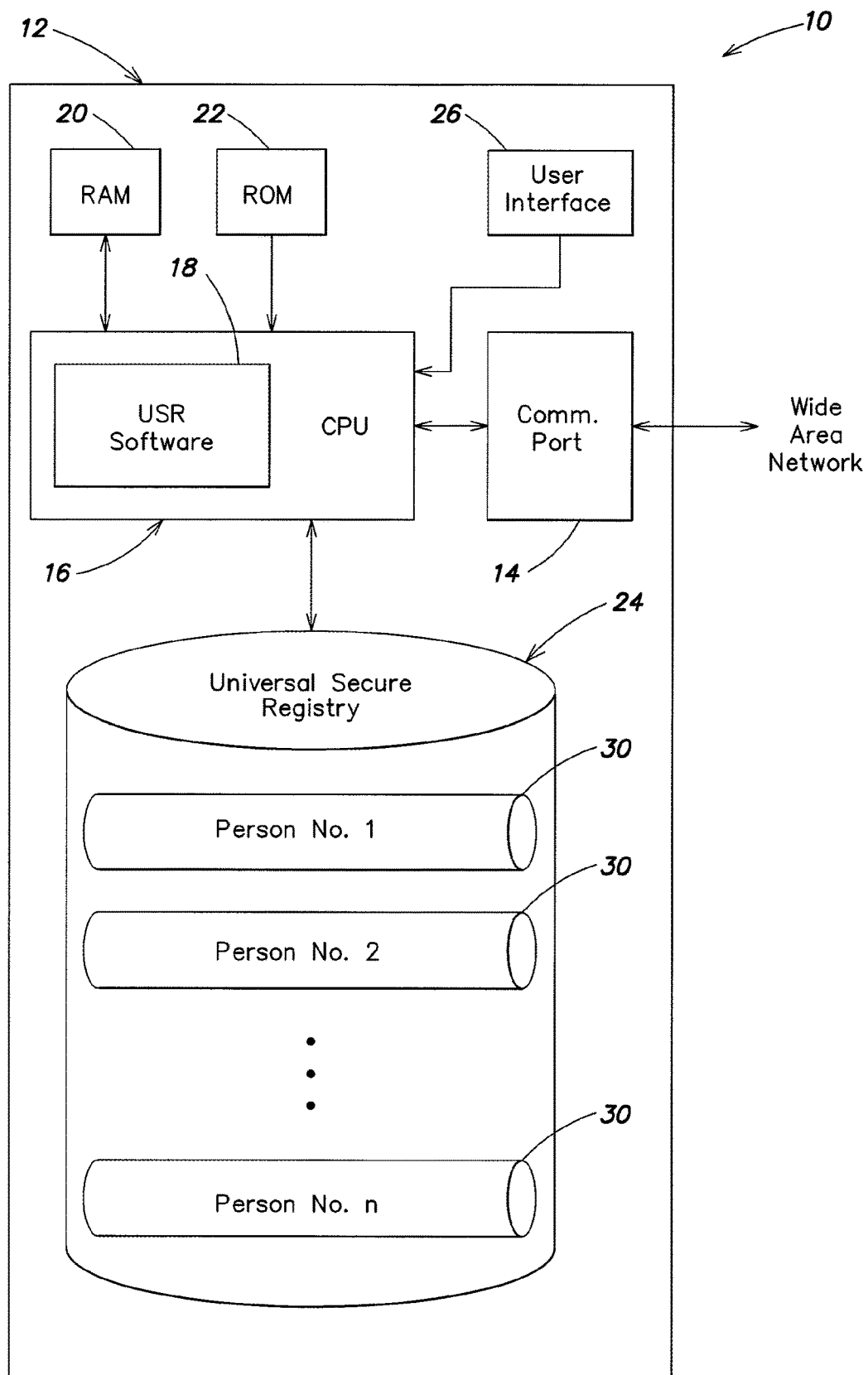
FIG. 1 is a functional block diagram of a computer system configured to implement the universal secure registry ("USR"), including a USR database, according to one embodiment of the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

In one embodiment, an information system is formed as a computer program running on a computer or group of computers configured to provide a universal secure registry (USR) system. The computer, in this instance, may be configured to run autonomously (without the intervention of a human operator), or may require intervention or approval for all, a selected subset, or particular classes of transactions. The invention is not limited to the disclosed embodiments, and may take on many different forms depending on the particular requirements of the information system, the type of information being exchanged, and the type of computer equipment employed. An information system according to this invention, may optionally, but need not necessarily, perform functions additional to those described herein, and the invention is not limited to a computer system performing solely the described functions.

In the embodiment shown in FIG. 1, a computer system 10 for implementing a USR system according to the invention includes at least one main unit 12 connected to a wide area network, such as the Internet, via a communications port 14. The main unit 12 may include one or more processors (CPU 16) running USR software 18 configured to implement the USR system functionality discussed in greater detail below. The CPU 16 may be connected to a memory system including one or more memory devices, such as a random access memory system RAM 20, a read only memory system ROM 22, and one or more databases 24. In the illustrated embodiment, the database 24 contains a universal secure registry database. The invention is not limited to this particular manner of storing the USR database. Rather, the USR database may be included in any aspect of the memory system, such as in RAM 20, ROM 22 or disc, and may also be separately stored on one or more dedicated data servers.

The computer system may be a general purpose computer system which is programmable using a computer programming language, such as C, C++, Java, or other language, such as a scripting language or even assembly language. The computer system may also be specially programmed, special purpose hardware, an application specific integrated circuit (ASIC) or a hybrid system including both special purpose components and programmed general purpose components.

In a general purpose computer system, the processor is typically a commercially available microprocessor, such as Pentium series processor available from Intel, or other similar commercially available device. Such a microprocessor executes a program called an operating system, such as UNIX, Linux, Windows NT, Windows 95, 98, or 2000, or any other commercially available operating system, which controls the execution of other computer programs and provides scheduling, debugging, input/output control, accounting, compilation, storage assignment, data management, memory management, communication control and related services, and many other functions. The processor and operating system defines a computer platform for which application programs in high-level programming languages are written.

The database 24 may be any kind of database, including a relational database, object-oriented database, unstructured database, or other database. Example relational databases include Oracle 81 from Oracle Corporation of Redwood City, Calif.; Informix Dynamic Server from Informix Software, Inc. of Menlo Park, Calif.; DB2 from International Business Machines of Armonk, N.Y.; and Access from Microsoft Corporation of Redmond, Wash. An example object-oriented database is ObjectStore from Object Design of Burlington, Mass. An example of an unstructured database is Notes from the Lotus Corporation, of Cambridge, Mass. A database also may be constructed using a flat file system, for example by using files with character-delimited fields, such as in early versions of dBASE, now known as Visual dBASE from Inprise Corp. of Scotts Valley, Calif., formerly Borland International Corp.

The main unit 12 may optionally include or be connected to an user interface 26 containing, for example, one or more input and output devices to enable an operator to interface with the USR system 10. Illustrative input devices include a keyboard, keypad, track ball, mouse, pen and tablet, communication device, and data input devices such as voice and other audio and video capture devices. Illustrative output devices include cathode ray tube (CRT) displays, liquid crystal displays (LCD) and other video output devices, printers, communication devices such as modems, storage devices such as a disk or tape, and audio or video output devices. Optionally, the user interface 26 may be omitted, in which case the operator may communicate with the USR system 10 in a networked fashion via the communication port 14. It should be understood that the invention is not limited to any particular manner of interfacing an operator with the USR system.

It also should be understood that the invention is not limited to a particular computer platform, particular processor, or particular high-level programming language. Additionally, the computer system may be a multiprocessor computer system or may include multiple computers connected over a computer network. It further should be understood that each module or step shown in the accompanying figures and the substeps or subparts shown in the remaining figures may correspond to separate modules of a computer program, or may be separate computer programs. Such modules may be operable on separate computers. The data produced by these components may be stored in a memory system or transmitted between computer systems.

Such a system may be implemented in software, hardware, or firmware, or any combination thereof. The various elements of the information system disclosed herein, either individually or in combination, may be implemented as a computer program product, such as USR software 18, tangibly embodied in a machine-readable storage device for execution by the computer processor 16. Various steps of the process may be performed by the computer processor 16 executing the program 18 tangibly embodied on a computer-readable medium to perform functions by operating on input and generating output. Computer programming languages suitable for implementing such a system include procedural programming languages, object-oriented programming languages, and combinations of the two.

Figure 2:
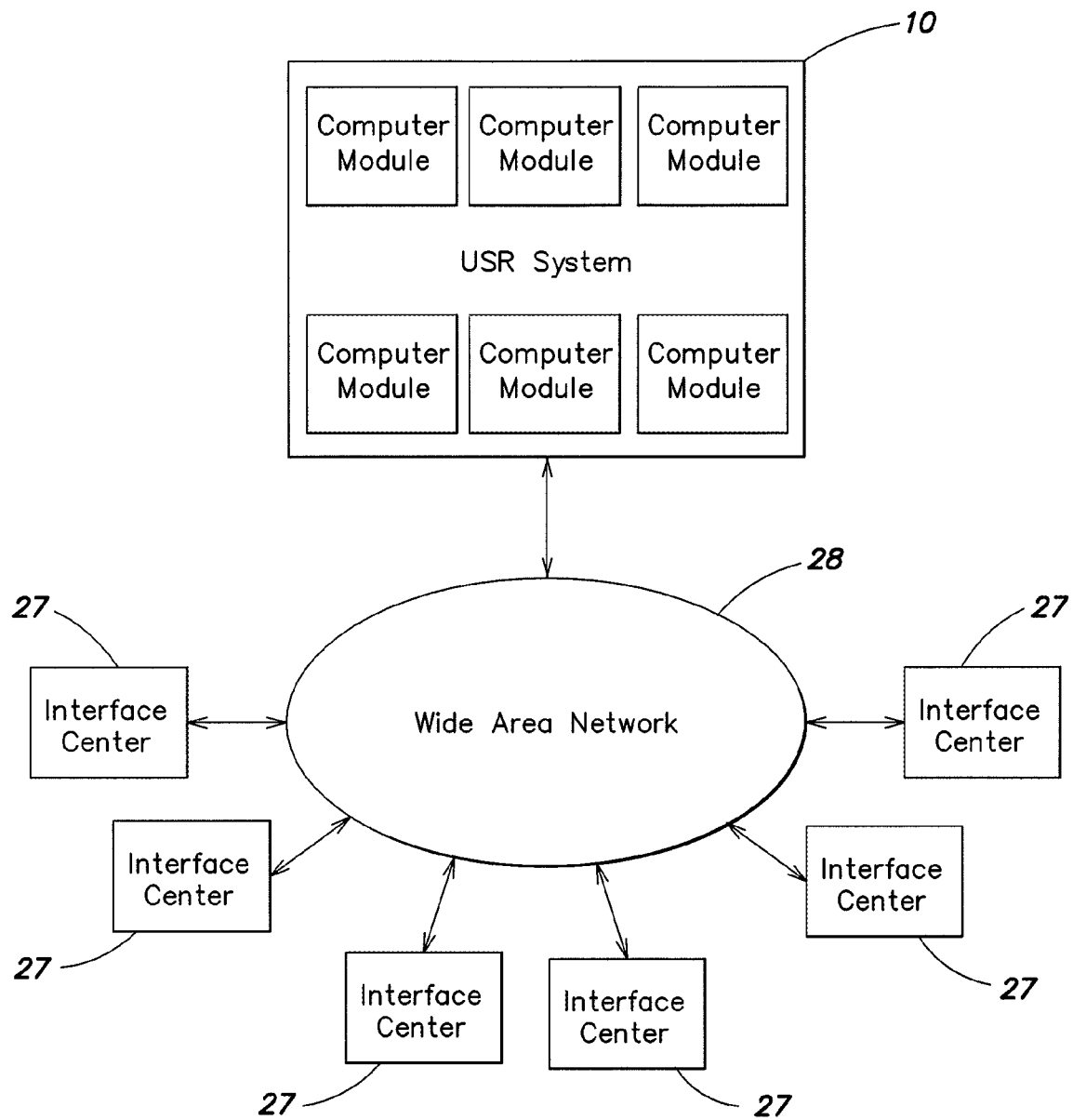
FIG. 2 is a functional block diagram of a first embodiment of a networked environment including the computer system of FIG. 1.

As shown in FIG. 2, the computer system 10 may be connected to a plurality of interface centers 27 over a wide area network 28. The wide area network 28 may be formed from a plurality of dedicated connections between the interface centers 27 and the computer system 10, or may take place, in whole or in part, over a public network such as the Internet. Communication between the interface centers 27 and the computer system 10 may take place according to any protocol, such as TCP/IP, ftp, OFX, or XML, and may include any desired level of interaction between the interface centers 27 and the computer system 10. To enhance security, especially where communication takes place over a publicly accessible network such as the Internet, communications facilitating or relating to transmission of data from/to the USR database 24 or the computer system 10 may be encrypted using an encryption algorithm, such as PGP, DES, or other conventional symmetric or asymmetric encryption algorithm.

In one embodiment, the USR system 10 or USR database 24 may be able to authenticate its identity to a user or other entity accessing the system by providing an appropriate code which may be displayed on the user's smart card, for example a SecurID™ card or its equivalent, or other code generator, for example a single use code generator, being employed by the user. A comparison by the user or the code generator between the provided number and an expected number can validate, to the user (or other entity) or the code generator, that communication is with the database and not an imposter. In another embodiment, a challenge-response protocol is employed to authenticate the identity of the USR system and/or the user to the other.

Figure 4:
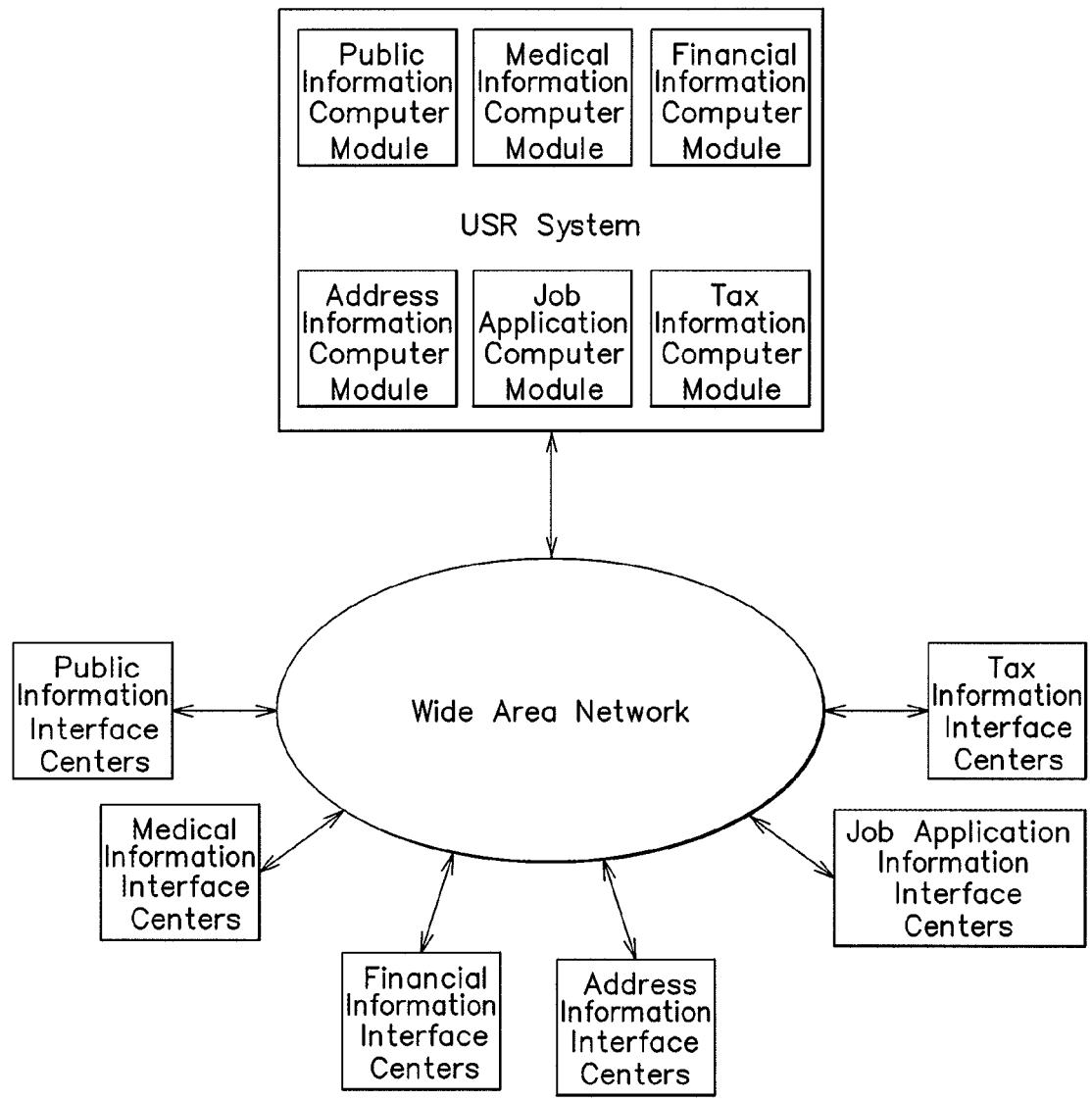
FIG. 4 is a functional block diagram of a second embodiment of a networked environment including the computer system of FIG. 1.

The database 24 shown in FIG. 1 has a USR database containing entries related to persons 1-$n$. The data in the USR database may also be segregated, as shown in FIG. 4, according to data type to enable individual computer modules to handle discrete applications on discrete data types. Segregating the data, as illustrated in FIG. 4, may make access to the database more robust by enabling portions of the data in the USR database 24 to be accessible even when it is necessary to perform maintenance on a portion of the database. However, storing the data in the USR database 24 according to the scheme illustrated in FIG. 1 may make it easier for a user of the database to make changes to multiple types of data simultaneously or in a single session. There are advantages and disadvantages to each data structure, and the invention is not limited to a particular manner of organizing the data within the database 24, data structures other than the two shown also being possible.

Figure 3:
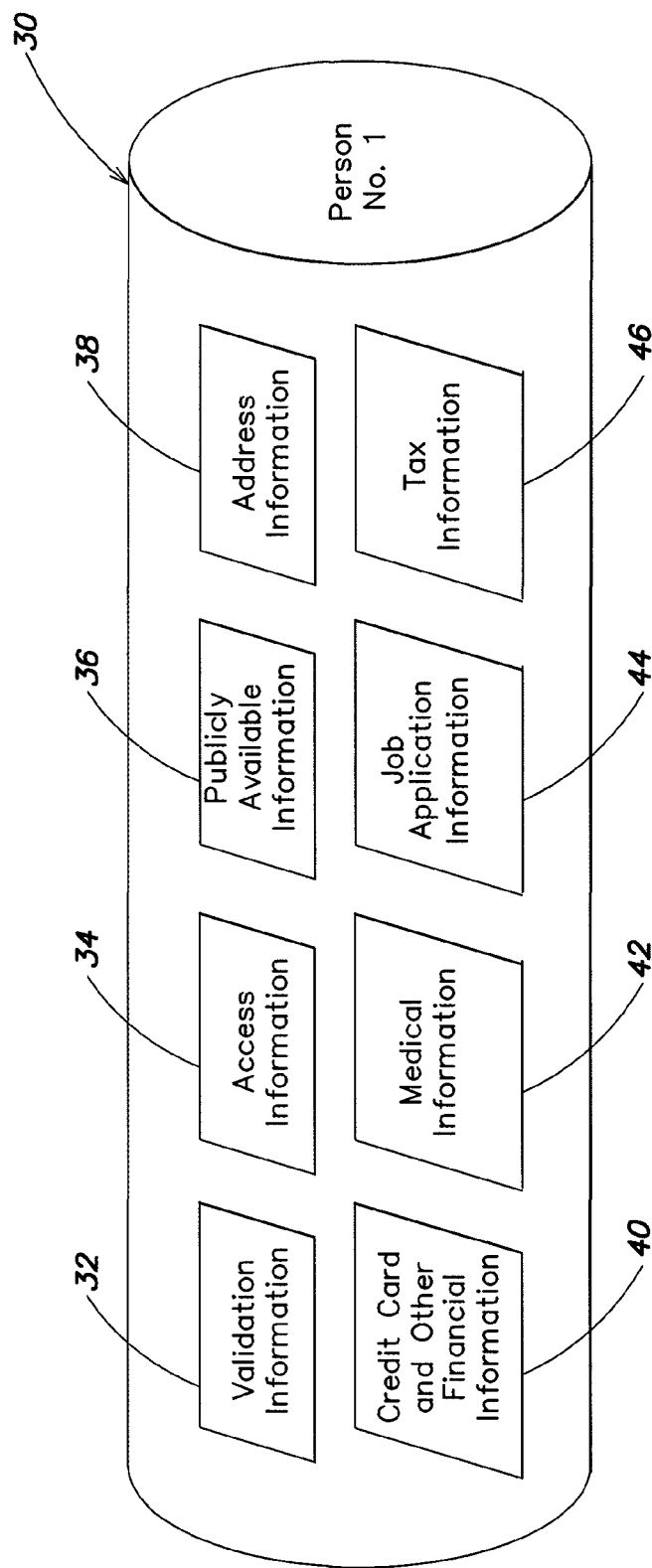
FIG. 3 is a functional block diagram of an entry of a database forming the USR database of FIG. 1.

As shown in FIG. 3, each entry 30 in the database 24 may contain multiple types of information. For example, in the embodiment shown in FIG. 3, the entry contains validation information 32, access information 34, publicly available information 36, address information 38, credit card and other financial information 40, medical information 42, job application information 44, and tax information 46. The invention is not limited to a USR containing entries with all of this information or only this particular information, as any information on a person or other entity such as a company, institution, etc. may be stored in USR database 24.

If the database information is split between multiple databases, each database will typically include at least the validation and access information to enable the USR software to correlate a validation attempt with a verified validation, and to enable the USR software to determine access privileges to the requested data. Alternatively, databases may be linked to permit information not in a main USR database to be retrieved, with validation/identification for all databases accessed being done at the USR system.

In FIG. 3, the validation information is information about the user of the database to whom the data pertains and is to be used by the USR software 18 to validate that the person attempting to access the information is the person to whom the data pertains or is otherwise authorized to receive it. The validation information may be any type of information that will reliably authenticate the identity of the individual. For example, in some embodiments, the information may include any of a secret known by the user (e.g., a pin, a phrase, a password, etc.), a token possessed by the user that is difficult to counterfeit (e.g., a secure discrete microchip), and/or a measurement such as a biometric (e.g., a voiceprint, a fingerprint, DNA, a retinal image, a photograph, etc.).

The user's identifying information may be manually entered or scanned at the interface center. However, a variety of types of communication may be employed to communicate the user's identifying information from the identification card or token to the computer system. For example, near field signal may be employed to communicate information between the identification card or token and the computer system 10. According to one embodiment, the user's identifying information is included in (or entered via) the user's cell phone where it is then communicated to the computer system 10. In one embodiment, the cell phone is also configured to receive information from the computer system 10 at the interface center 27.

In one embodiment, the user of the database will carry a SecurID™ card available from RSA Security, formerly Security Dynamics Technologies, Inc., of Cambridge, Mass. Use of this card enables secure access to the USR database without requiring the user to transmit any personal information. Specifically, to access the USR database, the card retrieves a secret user code and/or time varying value from memory and obtains from the user a secret personal identification code. The card mathematically combines these three numbers using a predetermined algorithm to generate a one-time nonpredictable code which is transmitted to the computer system 10. The computer system, specifically USR software 18, utilizes the received one-time nonpredictable code to determine if the user is authorized access to the USR database and grants access to the USR database if the user is determined to be authorized. The verification information 32 in the database entry in the embodiment of the invention illustrated in FIG. 3 contains information to enable the USR software 18 to validate the user using such a card in this manner.

Alternative types of identification cards or tokens may likewise be used. For example, other smart cards may be used which generate non-predictable single use codes, which may or may not be time varying, or other access code generators may be used. An algorithm generating such non-predictable codes may also be programmed onto a processor on a smart card or other computing device, such as a cell phone, pager, ID badge, wrist watch, computer, personal digital assistant, key fob, or other commonly available electronic device. For convenience, the term "electronic ID device" will be used generically to refer to any type of electronic device that may be used to obtain access to the USR database.

Likewise, various types of biometric information may be stored in the verification area of the database entry to enable the identity of the user possessing the identifying device to be verified at the point of use. Examples of the type of biometric information that may be used in this situation includes a personal identification number (PIN), fingerprint, voice print, signature, iris or facial scan, or DNA analysis. If desired, the verifying section of the database may contain a picture to be transmitted back to the person seeking to validate the device to ensure the person using the device is the correct person. Optionally, the identifying device itself may also be provided with a picture of the person authorized to use the card to provide a facial confirmation of the person's right to use the card.

Further, a challenge-response protocol may be employed in combination with or as an alternative to the preceding to validate the person attempting to access the information. Various embodiments may employ a challenge-response protocol with or without an identification card.

In FIG. 3, the Access information 34 is provided to enable different levels of security to attach to different types of information stored in the entry 30 in the USR database 14. For example, the person may desire that their address information be made available only to certain classes of people, for example colleagues, friends, family, Federal Express, U.P.S., and the U.S. mail service. The names or universal identifiers for those selected individuals, companies, organizations and/or agencies may be entered into appropriate fields in the Access information to specify to the USR software 18 those individuals to whom the address information may be released. Likewise, access fields may be specified for the other types of information. For example, the individual may specify that only particular individuals and/ or companies have access to the credit card and other financial information 40, medical information 42, job application information 44 and tax information 46. Additionally, the individual may specify that no one have access to that information unless the individual participates in the transaction (see FIG. 6).

As shown in FIG. 1, the USR software 18 contains algorithms for execution by the CPU 16 that enables the CPU 16 to perform the methods and functions of the USR software described below in connection with FIGS. 5-16. The USR software 18, in this embodiment, performs all functions associated with validating an electronic ID card. If desired, a separate validation software module may be provided to validate electronic ID devices outside of a firewall segregating the validation information from other user information.

This algorithm comprising the USR software 18 may be used to implement, in one exemplary embodiment, a USR system configured to enable selected information to be disseminated to selected individuals in a secure and dynamic fashion. This information may be used for numerous purposes, several of which are set forth below and discussed in greater detail in connection with FIGS. 5-16.

For example, the USR system may be used to identify the person, enable the person to be contacted by telephone or mail anonymously, enable the person to be contacted by telephone or by mail without revealing the person's telephone number or present location, enable the person to purchase items over the Internet or in a store without revealing to the merchant any personal identification information or credit card information, enable the person to complete a job application without completing a job application form, enable the police to discern the person's identity and any outstanding warrants on the individual, and numerous other uses. The invention is not limited to these several enumerated uses, but rather extends to any use of the USR database. The methods of using the USR database 24 will now be discussed in connection with FIGS. 5-16.

Figure 5:
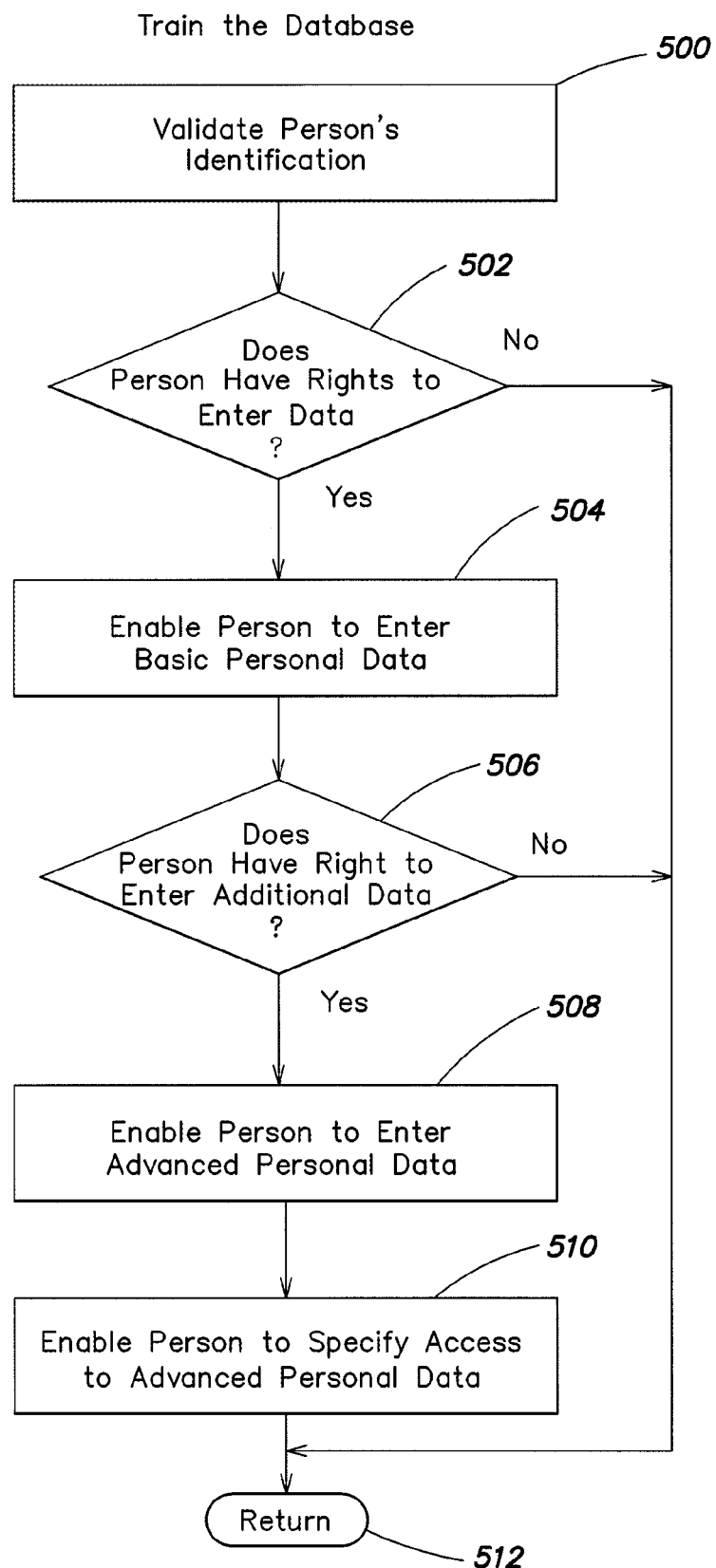
FIG. 5 is a flow chart illustrating steps in a process of inputting data into the USR database.

FIG. 5 illustrates a method of training the USR database 24. As shown in FIG. 5, the USR software 18 first validates the person's identification (500). The initial validation of the person's identification (500) may take place at the point of sale of an electronic ID device (for example, a smart card). This may be done in any conventional manner, such as by requiring the person to show a government issued identification card, passport, birth certificate, etc. Once the person's electronic ID device has been issued and initially validated, the validation process proceeds as discussed above.

After the validation process (500), the USR software 18 determines if the person has rights to enter data into the system (502). This step enables the system to charge persons for maintaining information in the USR database 24. For example, the USR software 18 may poll a database of current accounts or a database of accounts that are currently in default to determine if the person has paid the access fee to enter data into the database. A similar account status inquiry process may be performed by the USR software 18 in connection with each of the other methods set forth in FIGS. 6-16. If the person is not authorized to enter data into the USR database 24, the person is notified of the status of their account and the process returns (512) to wait for further input from another person. Alternatively, a person may be permitted to enter some classes of data into the system and update such classes of data at no charge, with a fee possibly being required for other classes of data, for example medical records. This would facilitate a more robust database.

If the person is authorized, the USR software 18 then enables the person to enter basic personal data into the USR database 24 (504). Optionally, personal data may be one class of data the USR software 18 allows the person to enter into the USR database 18 regardless of account status, i.e., for free.

The USR software 18 will then check to see if the person has additional rights to enter additional data (506), such as data to be entered into one of the other categories of data in FIG. 3. Optionally, this step of checking the person's rights to enter data (506) may be combined with the initial check (502). If the person does not have rights to enter any further data, the USR software 18 notifies the user and returns (512).

If the USR software 18 determines that the person has the right to enter additional data into the USR database 24, the person is prompted through the use of appropriate prompts, provided with forms, and otherwise enabled to enter advanced personal data into the USR database 24 (508). For each type of data entered, the person is asked to specify the type of access restrictions and/or whom should be allowed to access the advanced personal data (510). When the person has completed entering data into the database, the process returns (512) and commits the data to the database.

In the situation where only one person has access to enter and/or modify data for a given person in the database, there should be no conflict with committing data to the database. If, however, multiple people have access to a given account to modify data, the database may perform an integrity check to ensure the absence of conflict in the data before committing the new data to the database.

Figure 6:
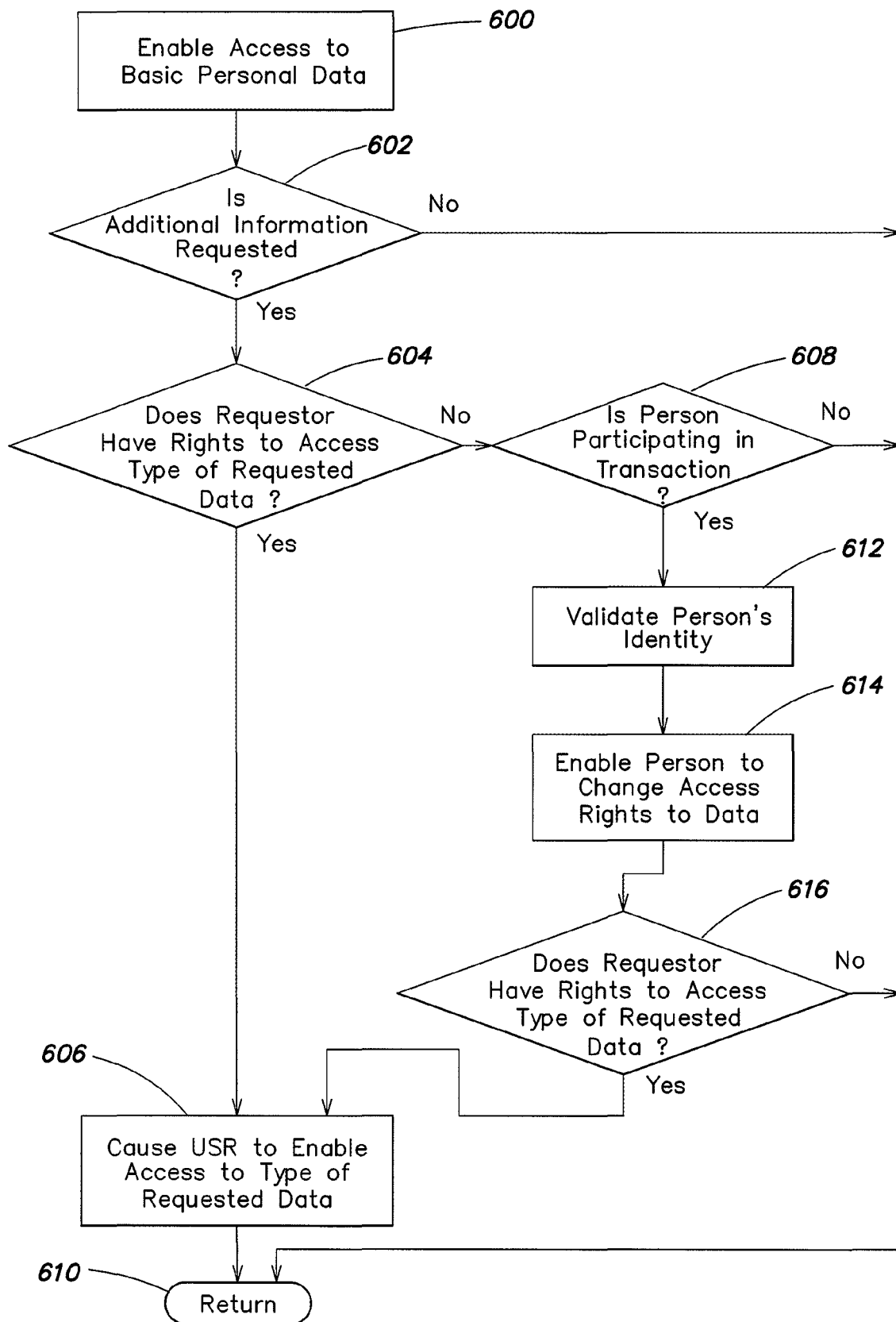
FIG. 6 is a flow chart illustrating steps in a process of retrieving data from the USR database.

Enabling access to the information in the database will be explained in greater detail in connection with FIG. 6. As shown in FIG. 6, the database will generally allow anyone to access basic personal data on anyone without performing any authorization check (600).

If information beyond that specified in the basic personal information area is requested, the USR software 18 queries whether the requestor has the right to access the type of requested data (602). The process of determining the requestor's rights (602) typically involves validating the requestor's identity and correlating the identity, the requested information and the access information 34 provided by the person to the USR database during the training process described above with respect to FIG. 5.

If the USR software 18 determines that the requestor has rights to access the type of requested data (604), the USR software 18 instructs the USR database 24 to enable access to the type of requested data (606). The actual step of enabling access to the type of requested data may involve multiple steps of formulating a database query, querying the USR database 24, retrieving the results, assembling the results into a user friendly or user readable format, and transmitting the information to the user.

If the USR software 18 determines that the requestor does not have the appropriate rights to access the type of requested data (604), the USR software 18 checks to see if the person is participating in the transaction (608). Checking to see if the person is participating in the transaction enables the user to authorize access to the requested data in real time. For example, a person may wish to participate in a transaction to give a potential employer one-time access to job application information 44 (see FIG. 3). If the person is not participating in the transaction, the USR software 18 determines that the requestor is not authorized to have access to the requested data, notifies the requestor of this determination, and ends (610).

If the person is participating in the transaction (608), however, the USR software 18 validates the person's identity (612) and enables the person to change access rights to the data (614). If the USR software 18 is not able to validate the person's identity, the USR software 18 refuses to allow the person to update the database, notifies the person and/or requestor of this determination, and returns (610).

It is also possible that a person may be required to grant access to certain data, for example financial data such as account numbers, under duress. The system may provide the person with the ability to safely signal this when accessing the system by using a selected access code or by making a known modification to the access code provided by the electronic ID device. On receiving such code, the system would take appropriate steps to protect the person, including for example alerting the police, tracking the person's location to the extent possible, providing traceable data, and the like.

Once the person has had the opportunity to change access rights to the data (614), the USR software 18 again checks to see if the requestor has rights to access the type of requested data (616). Although step 616 may seem redundant, given the fact that the person is participating in the transaction and has just previously changed access rights to the database to enable the requestor to have access to the data, step 616 is actually useful at preventing a different type of fraud. Specifically, the requestor may not be forthright with the person regarding the type of information they are requesting. If step 616 were omitted, the USR software 18 may inadvertently allow access to an unauthorized type of information in the situation where the requestor has surreptitiously requested multiple types of data.

If the USR software 18 determines that the requestor has rights to the type of data requested (616), it causes the USR database to enable access to the type of requested data (606). Otherwise, it notifies the requestor of the decision to deny access to the requested data and returns (610).

Various applications of the USR database 24 and USR software 18 will now be discussed in connection with FIGS. 7-16. These applications are merely exemplary of the types of applications enabled by the USR software 18 and USR database 24, and the invention is not limited to these particular applications.

Figure 7:
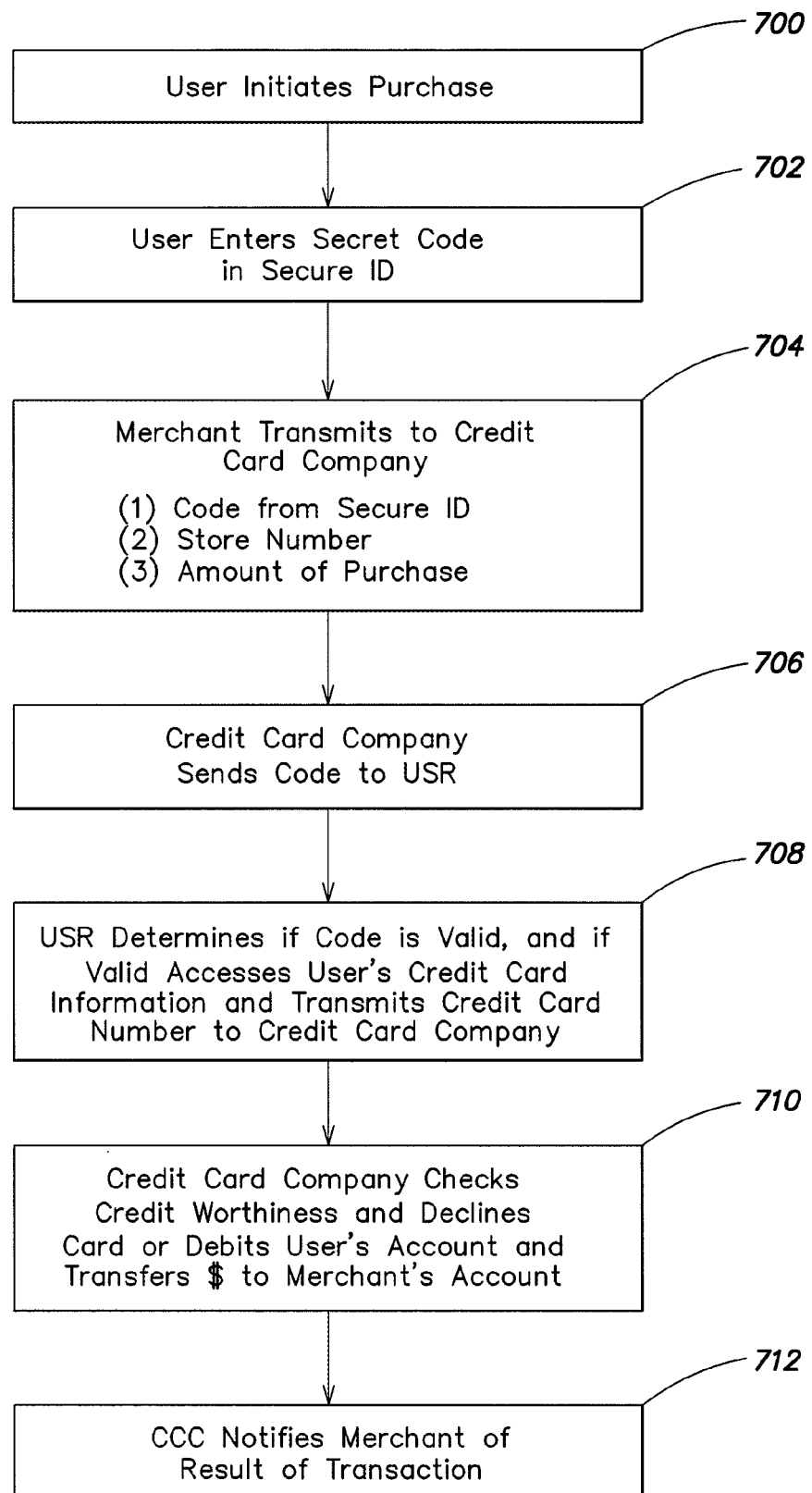
FIG. 7 is a flow chart illustrating a first protocol for purchasing goods from a merchant via the USR database without transmitting credit card information to the merchant.

FIG. 7 illustrates one embodiment of a method of using the USR software 18 and USR database 24 to purchase goods or services from a merchant without revealing to the merchant account information relating to the person's bank or credit card.

As shown in FIG. 7, when a user initiates a purchase (700), the user enters a secret code in the user's electronic ID device (702) to cause the ID device to generate a onetime code or other appropriate code, and presents the electronic ID device with the code to the merchant or otherwise presents the code to the merchant. The merchant transmits to the credit card company (1) the code from the electronic ID device, (2) the store number, (3) the amount of the purchase (704), and the time of receipt of the code. The credit card company takes this information and passes the code from the electronic ID device to the USR software 18 (706). The USR software 18 determines if the code is valid, or was valid at the time offered, and if valid accesses the user's credit card information and transmits the appropriate credit card number to the credit card company (708). While the link between the USR system and the credit card system is a secure link, there is always a danger that the link may be penetrated and credit card numbers obtained. This may be avoided by instead transmitting, on approval, a multidigit public ID code for the credit card holder which the credit card company can map to the correct credit card number. Even if the link is violated, the public ID code is of no value and the secure link prevents this code from being improperly sent to the credit card company. The credit card company checks the credit worthiness of the user and declines the card or debits the user's account in accordance with its standard transaction processing system (710). The credit card company then notifies the merchant of the result of the transaction (712). In this embodiment, the user has been able to purchase goods or services from a merchant without ever providing to the merchant the credit card number. Since the electronic ID device generates a time variant code or otherwise generates a code that can for example only be used for a single transaction, the merchant retains no information from the transaction that may be fraudulently used in subsequent transactions.

Figure 8:
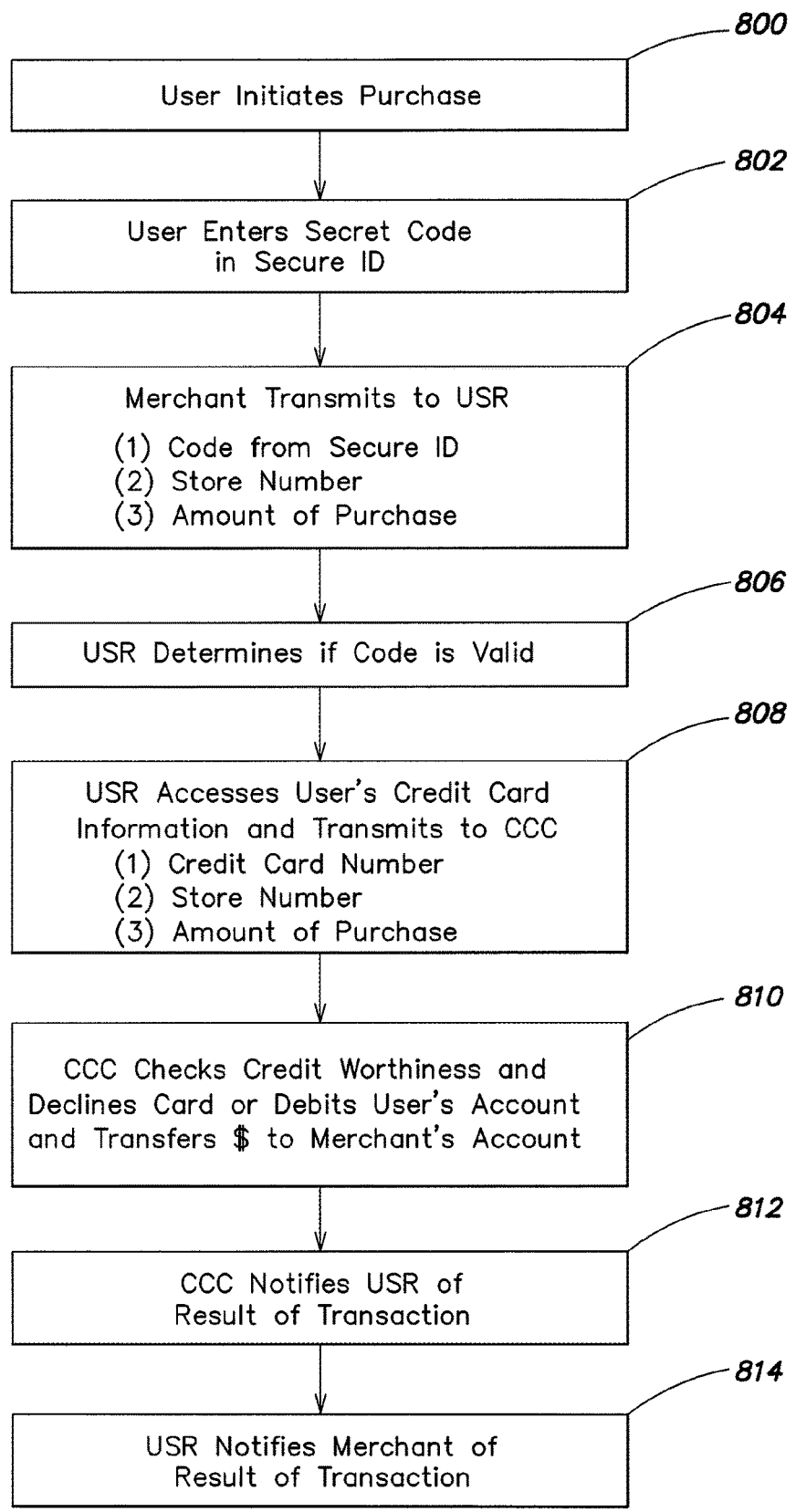
FIG. 8 is a flow chart illustrating a second protocol for purchasing goods from a merchant via the USR database without transmitting credit card information to the merchant.

Another embodiment of a system for facilitating purchase of goods or services without providing financial information to the merchant is set forth in FIG. 8. In FIG. 8, like FIG. 7, the user initiates a purchase (800), enters a secret code in the electronic ID device (802) and presents the resultant code to the merchant. The merchant, in this embodiment, transmits to the USR software 18, (1) the code from the electronic ID, (2) the store number, and (3) the amount of the purchase (804). The USR software 18 determines if the code is valid (806) and, if valid, accesses from the USR database 24 the user's credit card information (808). The USR software then transmits to the credit card company (1) the credit card number, (2) the store number, and (3) the amount of purchase (808). The information in this embodiment transmitted to the credit card company is intended to be in a format recognizable to the credit card company. Accordingly, the invention is not limited to transferring from the USR system 10 to the credit card company the enumerated information, but rather encompasses any transfer of information that will enable the use of the USR system 10 to appear transparent to the credit card company.

The credit card company then processes the transaction in a standard fashion, such as by checking the credit worthiness of the person, declining the card or debiting the user's account and transferring money to the merchant's account (810). The credit card company then notifies the USR system 10 the result of the transaction (812) and the USR software 18 in turn notifies the merchant of the result of the transaction (814).

In this embodiment, like the embodiment of FIG. 7, the user can use the USR system 10 to purchase goods or services from a merchant without providing the merchant with the user's credit card number. In the embodiment of FIG. 8, the interposition of the USR system 10 between the merchant and the credit card company is transparent to the credit card company and thus requires no or minimal cooperation from the credit card company to implement.

Figure 9:
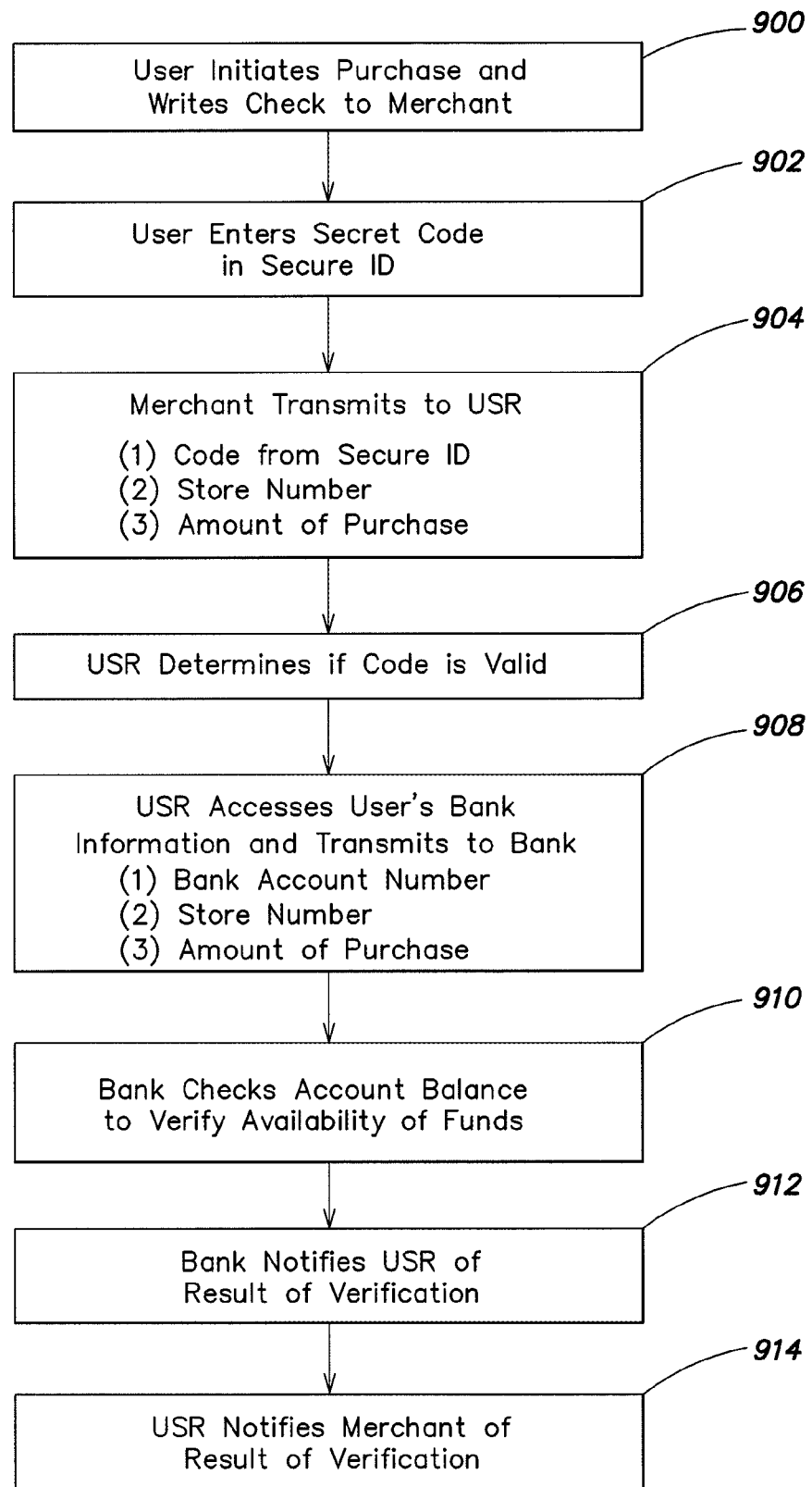
FIG. 9 is a flow chart illustrating a protocol for purchasing goods from a merchant via the USR database by validating the user's check.

FIG. 9 illustrates one embodiment of a method of using the USR system 10 to verify funds when using a check to purchase goods or services from a merchant. In the embodiment of FIG. 9, the user initiates a purchase and writes a check to the merchant (900). The check may be a conventional check containing identifying information, or may be a check bearing a unique serial number and no identifying information to enable the check to be used anonymously.

In either situation, the user enters a secret code into the electronic ID card and presents the resulting code to the merchant along with the check (902). The merchant transmits to the USR software 18 (1) the code from the electronic ID card, (2) the store number, and (3) the amount of the purchase (904). Where the check is an anonymous check, the merchant also transmits to the USR software 18 the check number.

The USR software 18 then determines if the code from the electronic ID is valid (906), and if valid accesses the user's bank information and transmits to the bank: (1) the user's bank account number, (2) the store number, and (3) the amount of the purchase (908). Optionally, the USR software 18 may additionally inform the bank of the check number.

The bank polls its own database to determine if there are sufficient funds in the user's account (910) and notifies the USR software 18 of the result (912). The USR software 18 then, in turn, notifies the merchant of the result of the verification (914).

This check verification system may take place over an unsecured connection between the merchant and the USR system 10 since the user's bank account information is not sent over the connection between the merchant and the USR system 10. Moreover, where an anonymous check is used, the merchant is not even provided with the person's name or account information in written form. This provides additional security against unauthorized persons writing subsequent checks.

The check verification system may be conducted over a telephone network, such as by having the merchant call a toll free number or over a network connection such as over the Internet.

Figure 10:
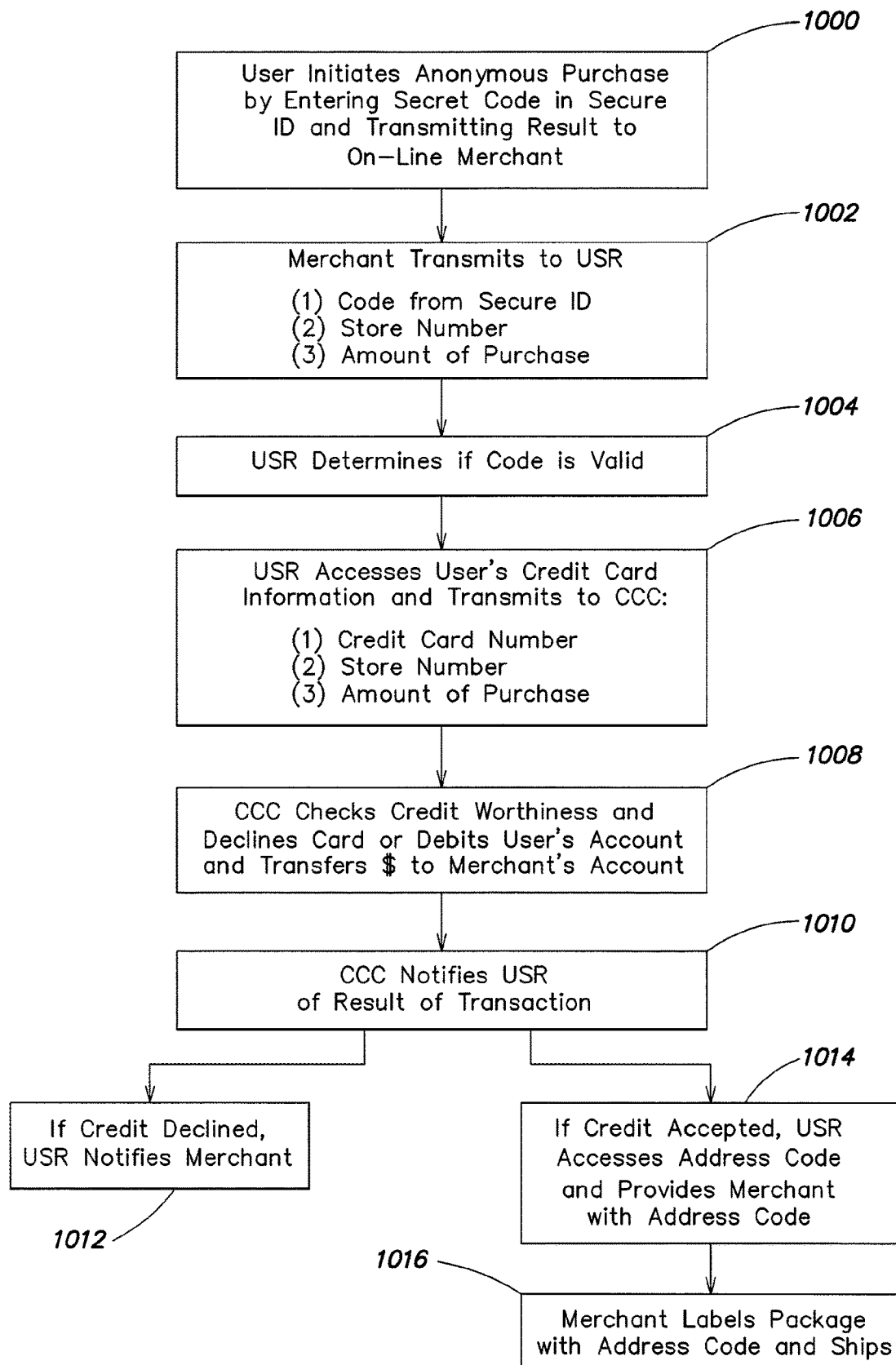
FIG. 10 is a flow chart illustrating a protocol for purchasing goods from an on-line merchant via the USR database without transmitting credit card information to the on-line merchant, and enabling the on-line merchant to ship the goods to a virtual address.

FIG. 10 illustrates a method of conducting a transaction with a merchant without requiring the user to provide to the merchant the user's name, address, or other identifying information, while enabling the merchant to ship the goods to the user. This may be beneficially employed, for example, in connection with transactions that take place between remote parties in a networked environment, such as the Internet.

As shown in FIG. 10, the user initiates an anonymous purchase by entering a secret code into the electronic ID device and transmitting the result to the on-line merchant (1000). The merchant transmits this information to the USR software 18, along with the store number and the amount of the purchase (1002). Optionally, the merchant may provide the store number and purchase price to the user and the user may send this information directly to the USR software 18 along with the code from the electronic ID. Where the number from the electronic ID device is a time varying number, the merchant may also need to input the time the number was received. Alternatively, the electronic ID device may encode or encrypt the time with the number, the USR software being able to extract time when receiving the number from the merchant. This may not be required where the time varying number varies slowly, for example changing every hour rather than every minute as with some devices.

In either event, the USR software 18 determines if the code is valid (1004) and, if valid, accesses the user's credit card information from the USR database 24 (1006). The USR software 18 then contacts the user's credit card company, as described above in connection with FIG. 8 (1008) and notifies the USR software 18 of the result (1010).

If the user's credit is declined, the USR software 18 notifies the on-line merchant and the transaction is terminated (1012). If the user's credit is honored, the USR software 18 polls the USR database 24 for the user's address and/or address code (1014). Address codes are discussed below in greater detail with reference to FIG. 11. The merchant then packages the goods into a parcel, labels the parcel with the appropriate address and/or address code and ships the parcel to the user (1016). Having the USR system 10 provide the address and/or address code to the on-line merchant enables the user to purchase items in a networked environment without requiring the user to input address information in connection with every sale.

Figure 11:
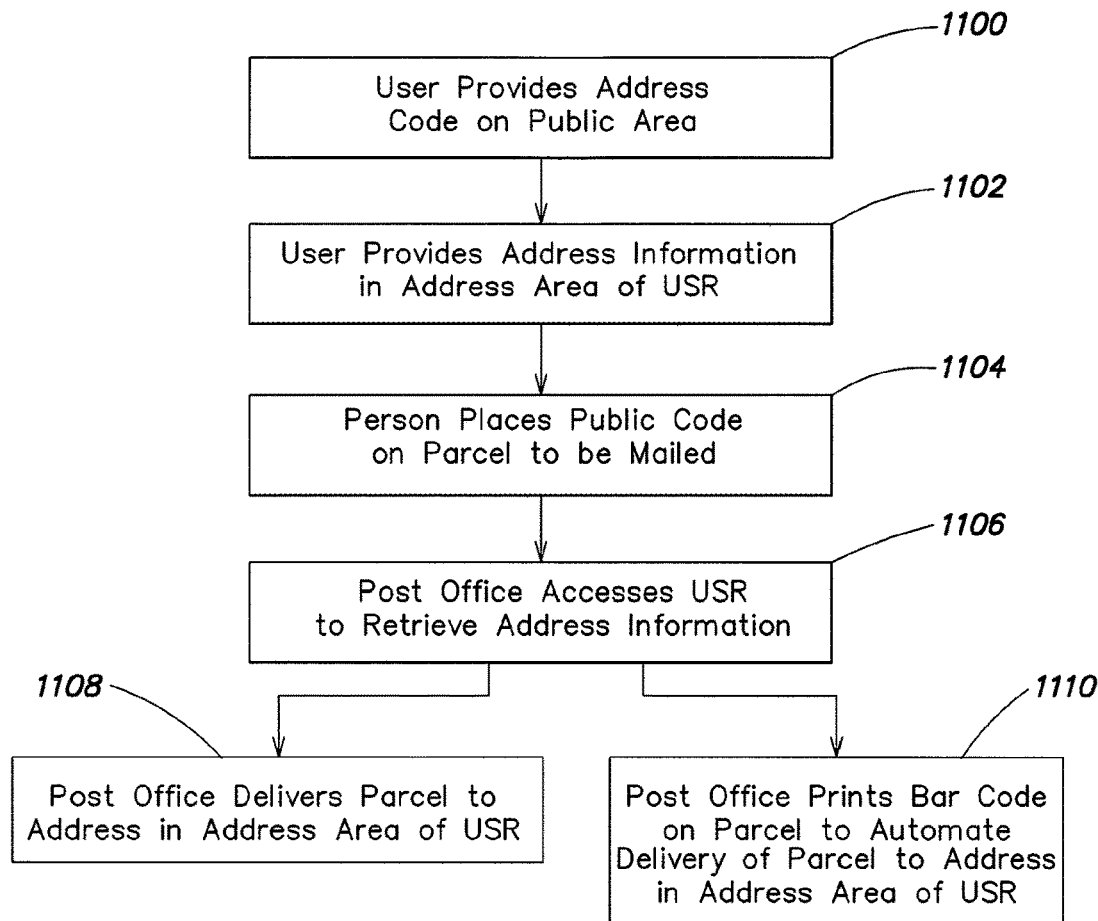
FIG. 11 is a flow chart illustrating a protocol for shipping goods to a virtual address via the USR database.

FIG. 11 illustrates a use of the USR database 24 to deliver mail to a user without requiring the user to provide address information to the sender. This may be useful in many contexts. For example, the user may wish that the address information be known only by the post office. In this instance, using the USR database 24 according to the method of the invention described below will enable the user to receive parcels without requiring the user to provide the merchant with the address information. Additionally, the user's address may change, temporarily, permanently, or frequently. Enabling the sender to send mail by entering a code instead of an address enables the post office to effectively deliver the coded mail to the corresponding address regardless of the frequency with which the address changes or the duration in which the address will remain valid.

In FIG. 11, the user provides an address code on a public area of the USR database 24 that is available to all persons to see (1100). This code may for example be six alpha characters, which should be adequate for currently anticipated system populations. Optionally, the user may provide this code directly to a merchant or other person desirous of sending the person one or more parcels.

The user also provides address information to the address information area 38 of the user's entry in the USR database 24 (1102). Access to the address information 38 is restricted by a rule or other appropriate entry in the access information 34 of the user's entry to only permit mail, parcel or other material delivery services, such as the US mail, UPS and Fed Ex to access the address information.

When someone wishes to have a parcel or other items delivered to the user, the sender retrieves the user's address code from the USR database 24 or otherwise receives the address code from the user, and prints the address code on the parcel (1104).

The delivery service accesses the USR software 18, validates its identity, and queries the USR database 24 for address information corresponding to the address code (1106). The USR database 24 retrieves the appropriate address data and provides the address information to the delivery service. The delivery service then either prints out an address label, prints a machine readable bar code to be attached to the package, or correlates an entry in a delivery database between the address code and the user address (1110). The delivery service then uses this retrieved information to deliver the package to the user while never supplying the merchant with the user's permanent or temporary address. A user may also assure that mail, parcels, etc. are delivered to a current location by providing only a single notice to the USR system, regardless of how frequently the person moves. The person can also automatically provide for address changes where the person moves according to a known schedule. Thus, deliveries to be made on a weekday could be directed to one address and deliveries on a weekend to another address; or deliveries during winter months to one address and during summer months to a different address.

Figure 12:
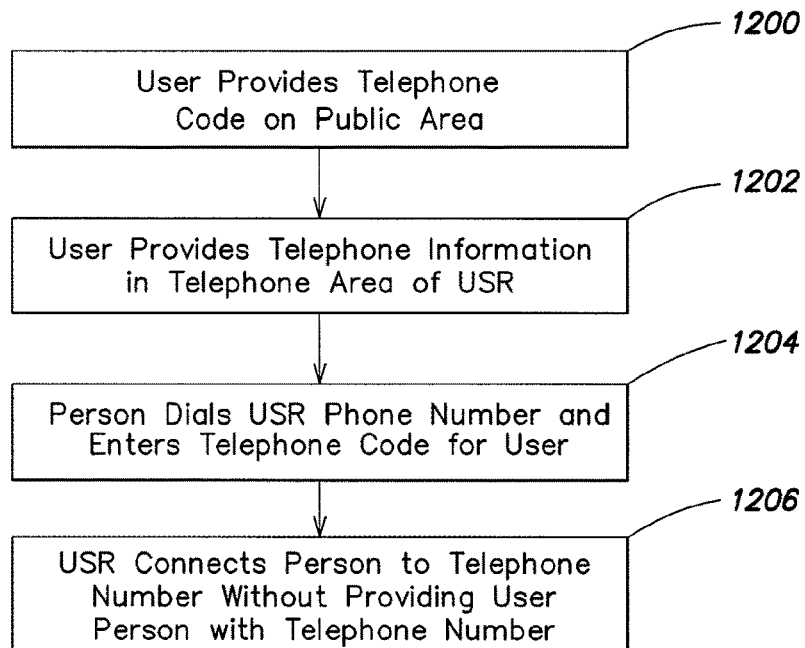
FIG. 12 is a flow chart illustrating a protocol for telephoning a virtual phone number via the USR database.

FIG. 12 illustrates a method of enabling a person to telephone a user of the USR system 10 without providing the user's telephone number to the person. In the embodiment illustrated in FIG. 12, the user provides a telephone code on the publicly available area of his entry on the USR database 24 (1200). This code may be assigned by the USR software 18 or made up by the user. The user also provides the USR database 24 with actual telephone information to enable the USR system 10 to connect callers with the user (1202).

The person wishing to telephone the user of the USR system 10 calls a telephone number and enters the telephone code of the user (1204). The USR software 18, optionally, may require the person to identify themselves to see if they are authorized to call the user. Assuming that the person is authorized to call the person, or if no authorization check is performed, the USR connects the person to the telephone number in the USR database 24 without providing the person with the telephone number.

Enabling the user to specify the telephone number may be advantageous for many reasons. First, the user may frequently be switching between telephone coverage areas and may wish to be reachable at all times. Simply by instructing the USR database 24 to connect incoming telephone calls to one of a myriad of numbers will facilitate connecting the incoming calls to, for example, the user's cell phone, work phone, pager, car phone or home phone, without necessitating the user to provide all these numbers to the caller. A similar system may be implemented for facsimile transmissions, e-mails or other communications.

The user also may have predefined rules to enable telephone calls to follow a set pattern. For example, the user may desire to receive telephone calls only from family members during the night time at home, may wish to have all incoming calls routed to a car phone during commuting hours, and may wish to have all incoming calls routed to a cell phone during lunch. These time dependent rules may and/or caller specific rules may be entered into the USR database to specify accessibility and connectivity of incoming telephone calls.

The publicly available address code and telephone code and any other codes may be the same, or may be different, there being some advantages to having a single code usable for all such applications for each person on the system. The codes could be accessible through a variety of media including telephone and the Internet. Where two or more people on the system have the same name, which will frequently be the case, additional publicly available biographical data may be provided with the name to assure that the right code is selected. The system may similarly be used to provide public keys for use in a public key/private key encryption system, to provide other public codes for an individual or to provide other public information. Access to such information would typically be unrestricted.

Where the system is used to provide public keys, the public code used to obtain the key, or possibly the public key itself, may be used as above to obtain the e-mail address, telephone number or the like for the person to whom the message is being sent, and the USR system may also be used to perform the encryption. When the recipient receives the message, he deencrypts it using the recipient's private key in standard fashion, including deencrypting the name of the sender. However, this does not necessarily verify the sender and such verification may be desirable for important messages, particularly ones involving large financial transactions. The USR system may accomplish such verification by also storing private keys for people in the system. The sender first authenticates himself to the system, and the system then adds a second signature to the message which is encrypted with the sender's private key. The receiving party deencrypts this signature with the sender's public key. Since the system only sends such signatures for authenticated users, the message is thus verified.

Figure 13:
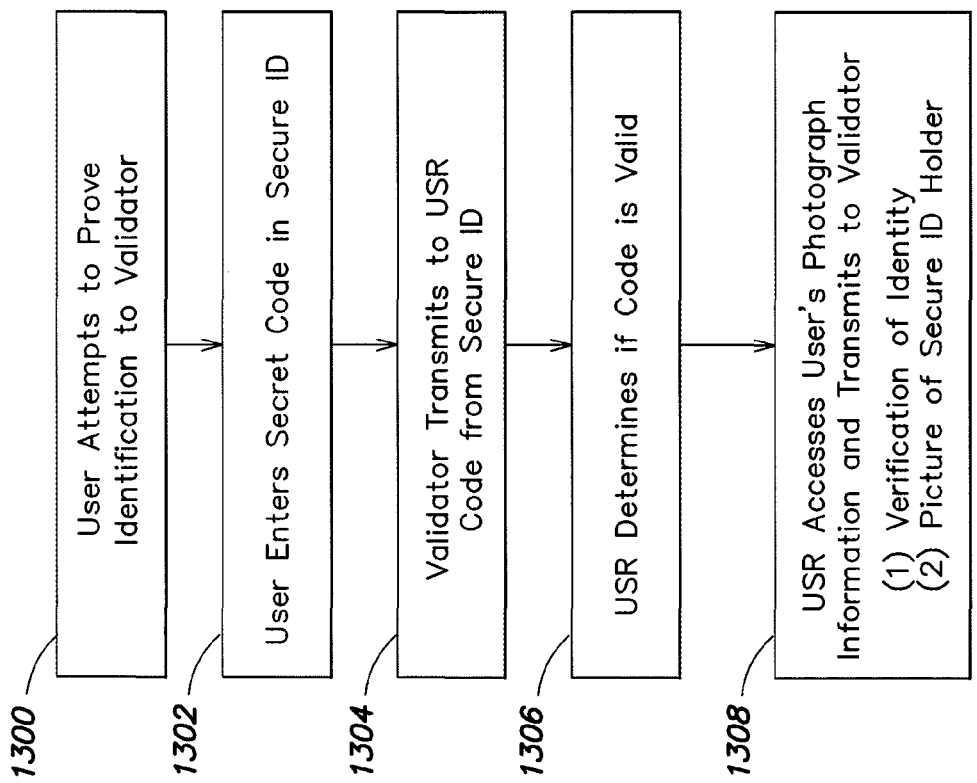
FIG. 13 is a flow chart illustrating a protocol for identifying a person via the USR database.

FIG. 13 illustrates a general method of using the USR database 24 to authenticate a user's identification. This may be used in connection with any of the other methods disclosed herein to ensure that the electronic ID device has not been stolen and/or hacked by an unauthorized holder.

Specifically, in the embodiment illustrated in FIG. 13, the user attempts to prove identification to a validator, such as to prove that the possessor of the electronic ID device is of sufficient age to purchase alcohol (1300). In connection with this attempt, the user enters a secret code into the electronic ID (1302). The validator transmits to the USR software 18 the code from the electronic ID (1304). If the USR software 18 determines that the code is valid (1306), it accesses the user's photograph, age information, or any other desired information, and transmits that information to the validator (1308). By transmitting back to the validator a picture of the person to whom the electronic ID card was issued, the validator can ensure that the person using the electronic ID card is the proper person. Likewise, the validator can ensure, based on the information provided by the USR system 10, that the person is as old as the person claims to be.

Figure 14:
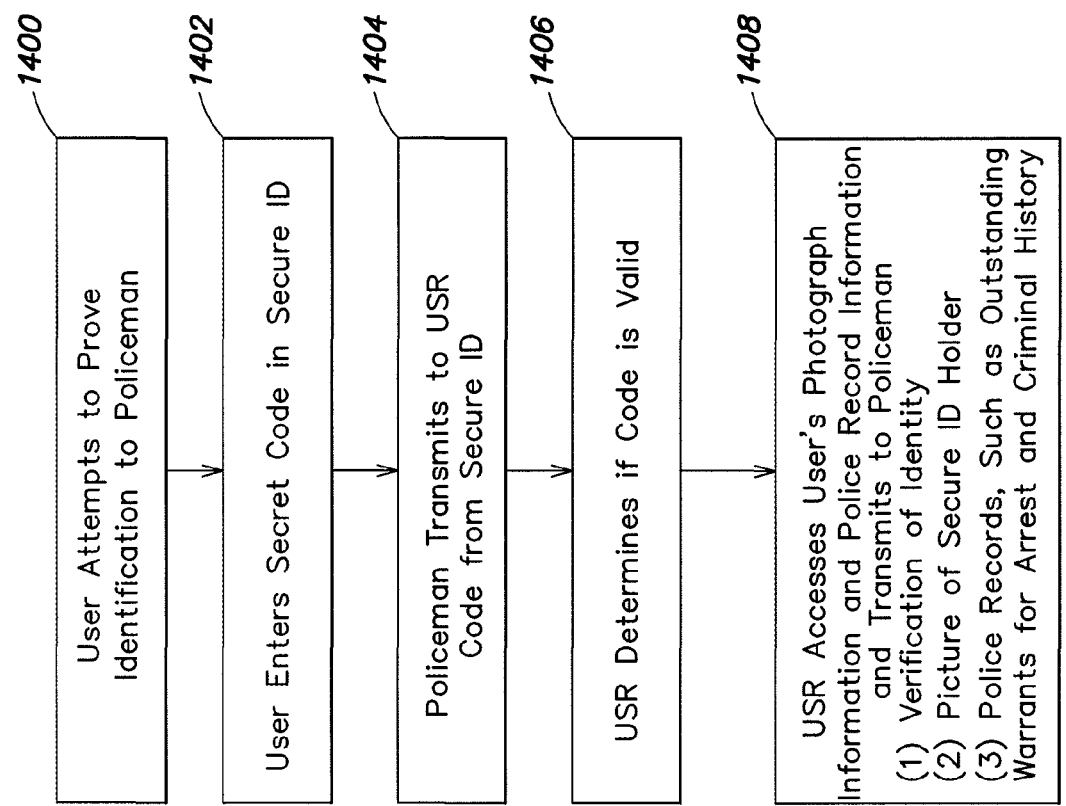
FIG. 14 is a flow chart illustrating a protocol for identifying a person to a policeman via the USR database.

A specific embodiment of this identification validation procedure is illustrated in FIG. 14. In FIG. 14, a policeman takes the place of the validator. In this scenario, however, instead of simply transmitting to the policeman a validation of the user's identity, such as their picture, the policeman may also receive additional information, such as the user's police records, records of any arrests, outstanding warrants, and other similar information that may be of use to the policeman when determining how to handle a particular individual.

Figure 15:
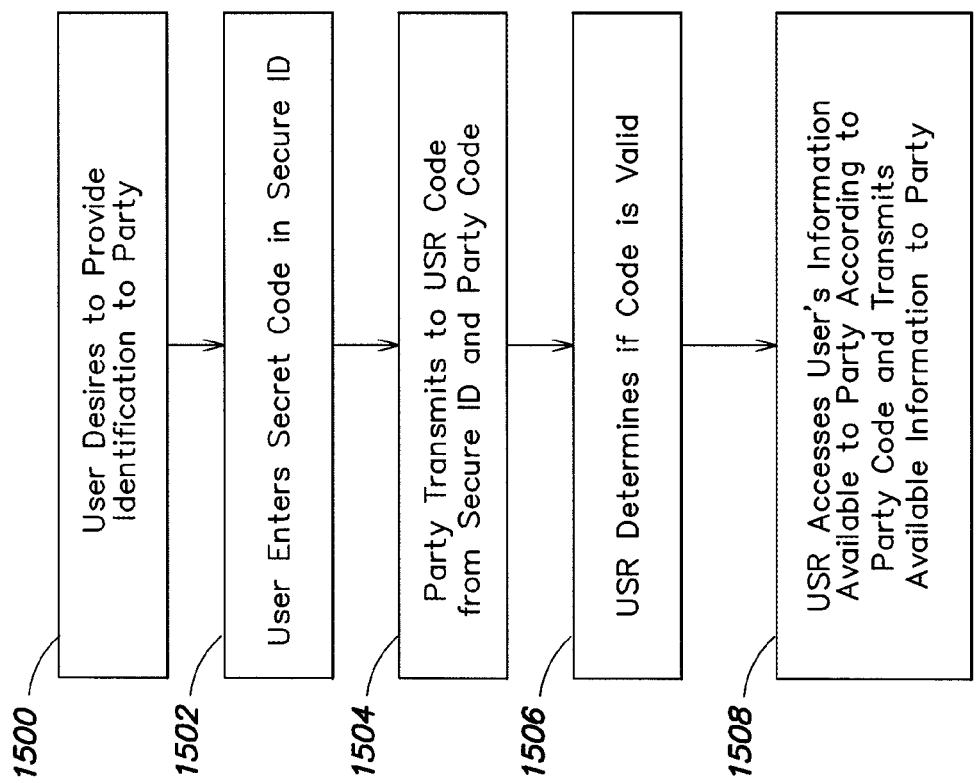
FIG. 15 is a flow chart illustrating a protocol for providing information to an authorized recipient of the information via the USR database.

FIG. 15 illustrates a process for enabling the user to provide specific information to a party, such as medical staff in an emergency room. As shown in FIG. 15, if the user desires to provide information to a party (1500), the user enters a secret code in the electronic ID device and provides the electronic ID code to the party (1502). The party transmits to the USR software 18 the ID code and the party code (1504). The party code may be a code from for example an electronic device which identifies the party, may be a status code which identifies the class of users to which the party belongs, for example policeman, emergency room personnel, doctor, etc. or may be a combination of both, the status code for example being encrypted into the ID code. The USR software 18 determines if the code is valid (1506), accesses the user's information in the USR database 24 and transmits available information to the party (1508). In this scenario, the user may be provided with a plurality of different codes to enter into the electronic ID device depending on the type of information to be released to the party. For example, the user's basic code may be 1234. The fifth digit of the electronic code may specify the type of information to be provided, i.e., 1=address information, 2=medical information; 3=telephone information, 4=job application information, etc. Using multiple codes eliminates any ambiguity about the authority provided by the user to the party, but requires the user to remember additional information.

The above assumes the user is able to provide an ID code when the information is required. However, in for example an emergency room situation, the user may not be in a position to provide the ID code, but would still want medical records provided. The release authorization for certain portions of the user's database could therefore specify that the information be released to certain class or classes of individuals and the USR system would release such information to individuals or organizations based only on status code. Thus, the status code of an emergency room could alone trigger release of medical data.

Figure 16:
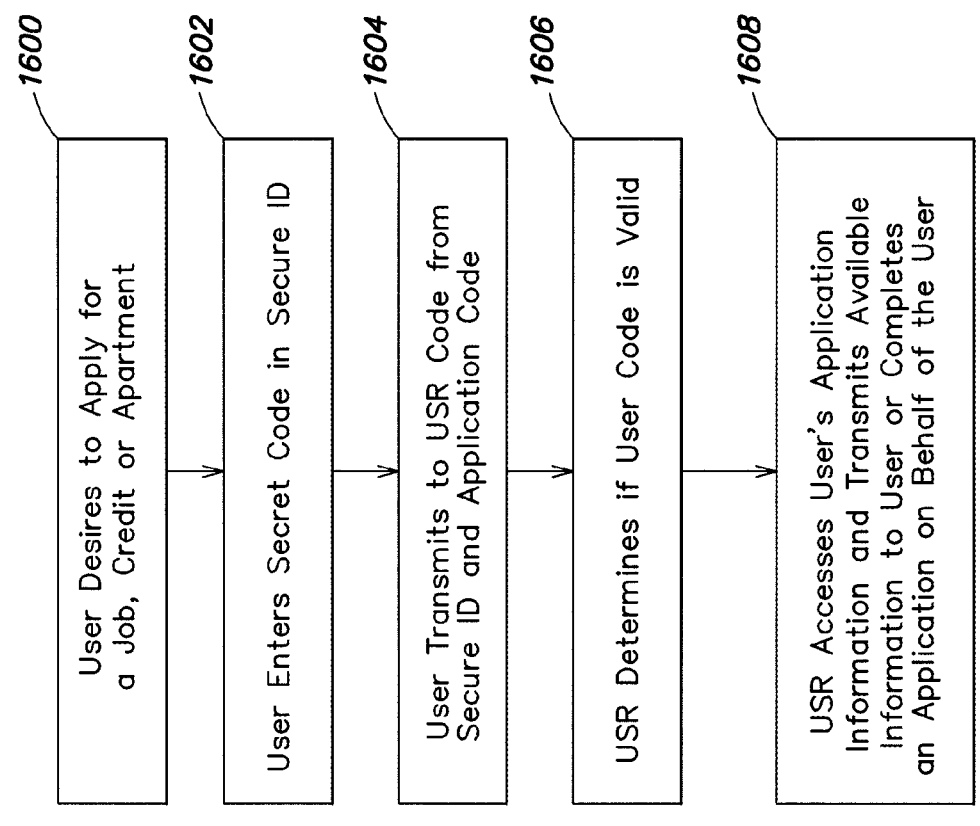
FIG. 16 is a flow chart illustrating a protocol for providing application information to an authorized recipient of the information via the USR database.

FIG. 16 illustrates one embodiment of a method of using the USR database 24 to complete a standard application, such as a job application or an application to rent an apartment. This embodiment is a specific example of the more generic method of enabling a party to retrieve information discussed above with respect to FIG. 15. In FIG. 16, however, the party may be provided with the opportunity to provide a form to the USR software 18, the fields of which may be automatically completed with information from the job application information section of the USR database 24.

As can be seen from the above, many of the users of the USR system are organizations or agencies such as carriers (post office, UPS, FedEx), communication companies, law enforcement organizations, hospitals and other medical facilities and the like. Each of these organizations can be provided with specialized software either on a disc or other suitable media or electronically, for example over the Internet, which performs a number of functions, for example automatically generating status codes for data access requests, controlling information received, and formatting data received in response to a request in a desired way. This can result in an access request from such organization for a given user causing all data on the user required to complete the form being retrieved and presented to the organization in the format of their form. A user may also authorize an organization for which a form has been completed using the USR system to receive updates, either in response to a request from the organization or at selected intervals, for example once a year, so as to maintain information in the forms current. Since the user will be providing information to the system on a regular basis, this is a relatively easy and painless way for the user to maintain current information with many organizations the user deals with. Another potential use of the system is to permit a person to be located where only limited biographical information on the person is known. Users of the USR system wishing to participate in this feature could be cued to provide non-confidential biographical data when they come on the system or at any time thereafter when they decide to participate. They can also indicate whether they wish their name given out in response to such an inquiry or to merely be alerted to an inquiry which might involve them and information on the requester. A person seeking to find another person or group of people can input appropriate biographical data, for example members of a 1975 Harvard University hockey team, or information of a person's last known address plus school information, etc. The system will then provide a list of persons who meet the listed criteria from which the person making the inquiry can hopefully find the person they are looking for.

In the above application and others, when a person is located, the person may request that only the person's address code or general access code (i.e. a single code which is used to get current address, telephone, e-mail, etc. information) be provided when the person is located. This can further protect the individual from undesired contacts.

Further, although each of FIGS. 13-16 refer to the entry of a secret code for validation by the USR system, the processes illustrated for each of FIGS. 13-16 may include a challenge-response protocol by which the user's identity is authenticated.

Figure 17:
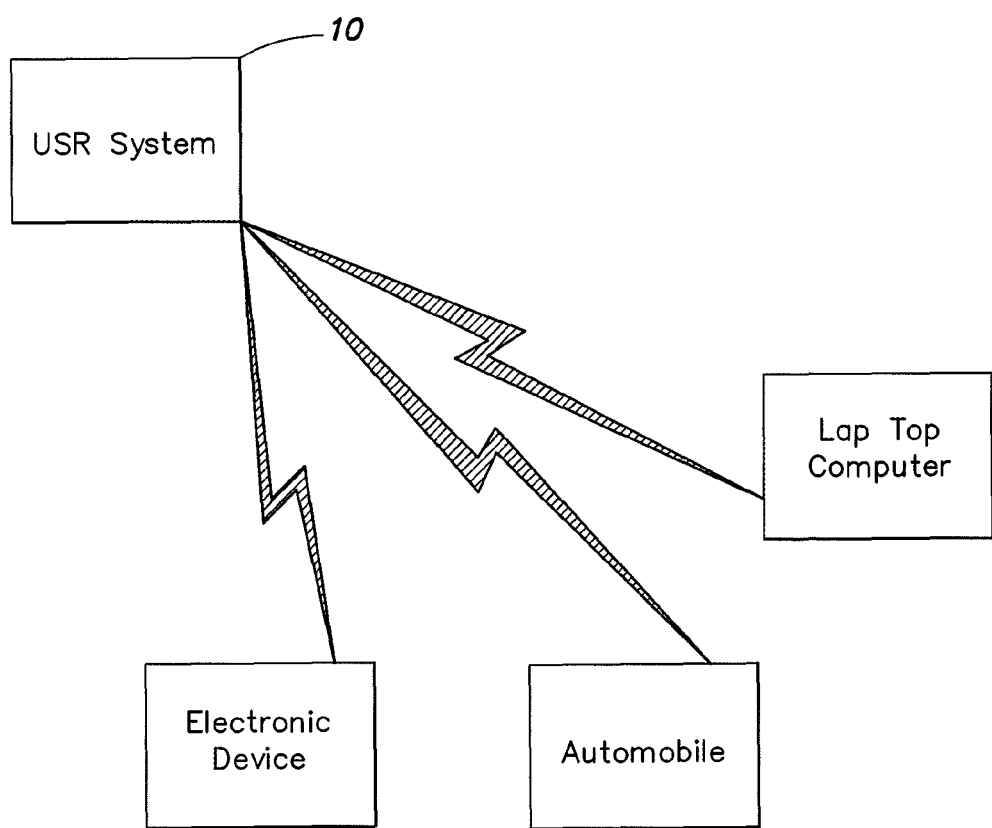
FIG. 17 is a functional block diagram of an embodiment configured to use information in the USR system to activate or keep active property secured through the USR system.

FIG. 17 illustrates another embodiment of the invention. As shown in FIG. 17, the USR system 10 may be used to secure expensive personal equipment, such as stereos, televisions, laptop computers, cellular telephones, cars, boats, and other items of value to a person. In this embodiment, each item to be secured using the USR system is provided with a USR timer chip imbedded in the electronics. If the USR timer chip is not provided with a code within a predefined period of time, for example every 30 days, the equipment is deactivated. Thus, for example, a television, mobile phone, laptop computer, automobile, heavy equipment, weapon or facility may be provided with a security chip having an internal timer that must be reset before expiration by provision of a particular code. When reset does not occur, the timer will disable the electronic device or other device using any one of a number of known disablement methods. Exemplary codes may be transmitted in the same manner as beeper signals are conventionally transmitted or may be transmitted to wired devices over the Internet or other public network.

The USR system 10 may be advantageously employed to automatically provide the secured property with the necessary codes at appropriate intervals, unless instructed by the user of the USR system 10 to cease doing so. Alternatively, the USR system 10 may require participation by the user prior to sending out the activation codes.

In this embodiment, the user may provide to the USR system 10, information indicative of the codes to be transmitted, timing information, and automation information whether the codes should be sent automatically or should require user intervention. Optionally, where the user opts to require user intervention, the USR system 10 may notify the user of the upcoming deadline via e-mail or another method.

This system may be useful to secure sensitive equipment other than personal equipment as well, such as military equipment, public equipment, school equipment and any other equipment that is subject to theft.

Figure 18A:
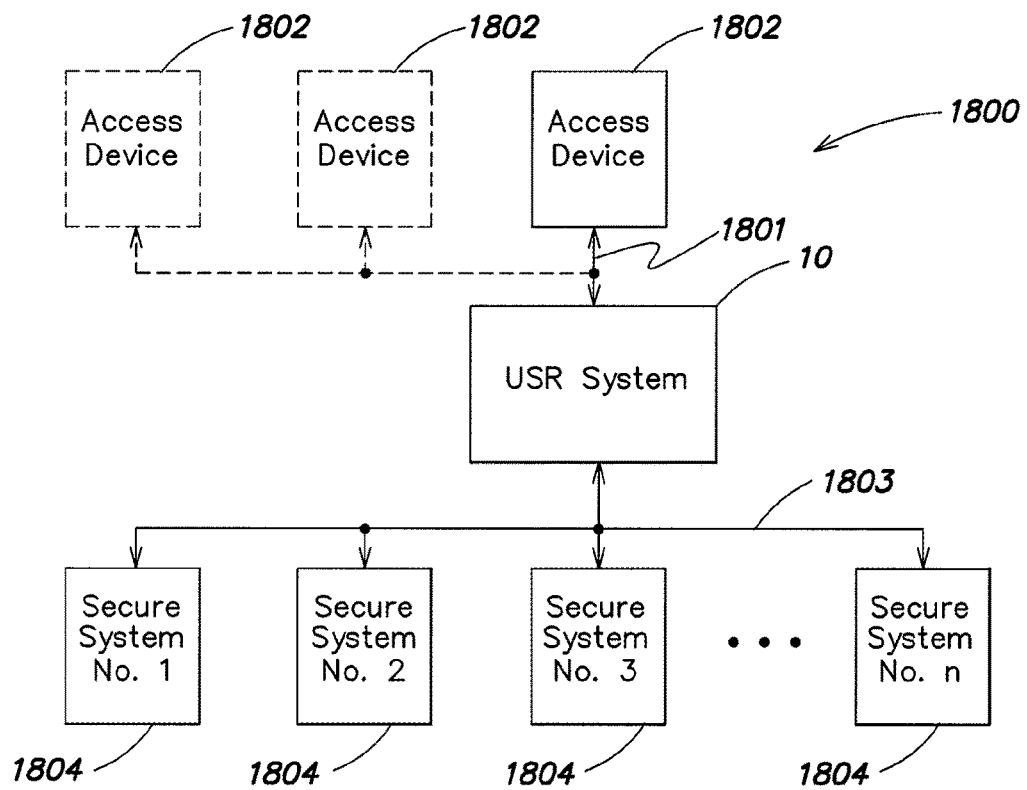
FIG. 18A is a functional block diagram of an embodiment configured to use the USR system to control access to a secure computer network.

FIG. 18A illustrates another embodiment of the invention that can provide a centralized system to control access to a plurality of secure networks. As shown in FIG. 18A, for example, a system 1800 may employ the USR 10 to control access to a plurality of secure systems 1804 (e.g., a plurality of secure computer networks). The system 1800 may include one or more access devices 1802 that can be employed by a user to access a secure computer network included in the plurality of secure systems. In addition, the system 1800 may be employed to protect other secure systems such as secure communication networks and/or other resources that are accessed electronically. According to one embodiment, the system 1800 includes a first communication link 1801 that provides a communication path between the access device 1802 and the USR 10, and a second communication link 1803 that provides a communication path between the USR 10 and the plurality of secure system 1804. In one embodiment, each of the first communication link 1801 and the second communication link 1803 are wide area networks, for example, the Internet.

Each of the secure systems 1804 can be associated with an organization. An organization is any entity that employs a secure (e.g., restricted access) host system to provide resources to a plurality of users. For example, an organization may be a corporation (including a non-profit corporation), partnership, other business entity, an affiliation or individual that employs a secure host system to provide resources to a plurality of authorized users. As should be apparent to those of ordinary skill in the art, an organization is not restricted to any particular size, for example, as measured by the number of members or employees.

More specifically, each of the secure systems No. 1, No. 2, No. 3, etc. may be associated with a different organization and the USR 10 may control access to each of the secure systems. That is, the USR 10 can provide access control for a plurality of secure computer networks each associated with a different and unrelated organization. Further, each of the secure computer networks may have a different plurality of users who are authorized to access the network.

The access device may include any of a desktop computer, a laptop computer, and a handheld computer (e.g., a PDA, call phone and the like). Further, as shown in phantom, a plurality of access devices may communicate with the USR 10. Where a web-based system is employed, for example, each of a plurality of computers connected to the Internet may be individually employed as a separate access device to communicate (e.g., independently communicate) with the USR 10 to gain access to one or more of the secure systems 1804.

For example, the access device 1802 may be a computer employed with a client-server network. In this example, to access resources provided by one of the secure system 1804, the user initiates an access request for a secure system 1804 selected by the user. That is, the user may supply authentication information and a computer network ID to the USR. As is described in further detail below, the authentication information and the computer network ID are processed by the USR to authenticate the user and determine whether the user is authorized to access the secure system 1804 that is identified by the computer network ID. The USR then routes communications between the user and the secure system provided that the user authentication is successfully completed.

According to one embodiment, the USR 10 connects the access device 1802 to one of the secure systems 1804 via a communication path that does not include the USR 10. In an alternate embodiment, the USR 10 connects the access device 1802 to one of the secure system 1804 via a communication path that does include the USR.

Figure 18B:
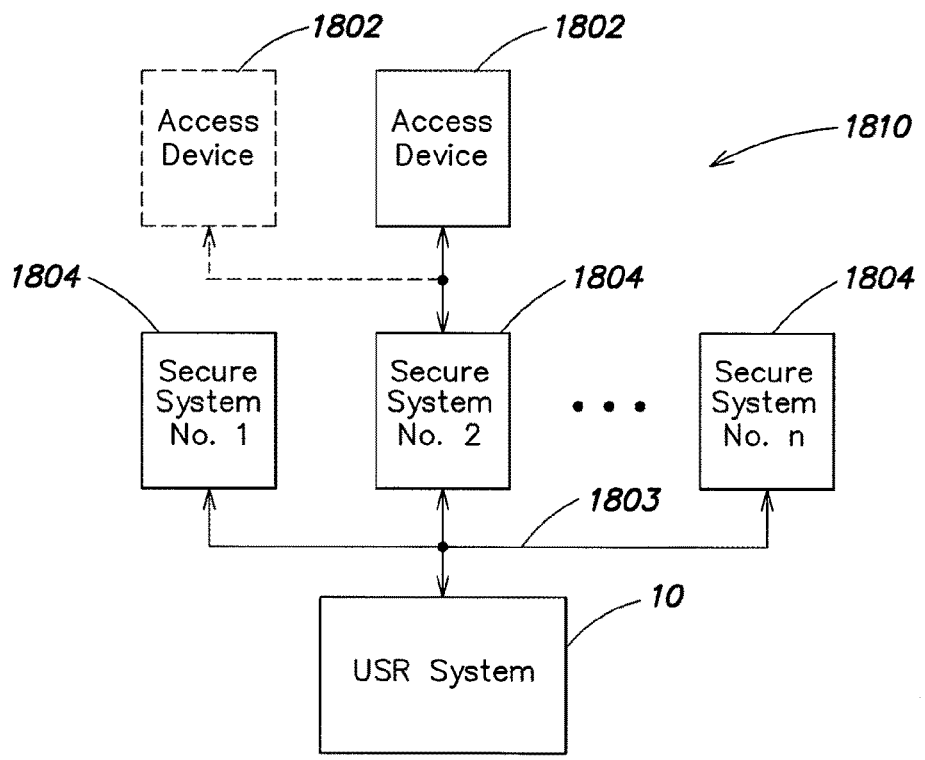
FIG. 18B is a functional block diagram of another embodiment configured to use the USR system to control access to a secure computer network.

Referring now to FIG. 18B, a system 1810 employs a USR 10 to control access to a secure system (e.g., a secure computer network) according to another embodiment. In one embodiment, the system 1810 includes the USR 10, an access device 1802, and a plurality of secure system 1804. According to this embodiment, the user selects from the plurality of secure systems 1804 a secure system that the user would like to access. With the access device 1802, the user communicates authentication information directly to the selected secure system 1804, e.g., without gaining access to the system. The secure system then communicates the authentication information and/or information corresponding to the authentication information to the USR 10. The USR 10 processes the information received from the secure system and then communicates an indication of whether the authentication information corresponds to one of the plurality of users authorized to access the secure system. The secure system grants or denies access to the secure system (and the associated resources) based on the indication received from the USR 10.

As illustrated in FIGS. 18A and 18B, the USR 10 can provide a centralized access control system (e.g., an authentication system) for a plurality of secure systems 1804 that are associated with independent organizations that may have no affiliation with one another. Referring to FIGS. 18A and 18B, a first organization may be associated with (have resources located on and/or accessed by) the secure system no. 1, a second organization may be associated with the secure system no. 2, and so on. In addition, a single organization may also be associated with a plurality of the secure systems 1804. Thus, in one embodiment, the USR 10 provides access control to a plurality of secure systems for a single organization.

The systems 1800 and 1810 allow an organization to operate a secure system without hosting the authentication system software or at least without the need to host a substantial part of authentication system software. Thus, in one embodiment, software upgrades/maintenance can be implemented at the USR 10 (e.g., centrally) for the plurality of secure systems 1804 and specialized authentication software is not required at the access device. In a further embodiment, specialized authentication software is also not required at the secure system. In versions of these embodiments, the USR 10 provides a web-based system in which the user employs a web-browser when communicating with the USR 10 and the secure system.

The USR 10 can also provide centralized administration and management for the plurality of secure systems 1804. The centralized administration can include routine tasks such as adding or removing authorized users for each of the plurality of secure systems 1804, for example, based on the hiring or resignation, respectively, of an employee. Additional administrative functions such as maintaining a secure database of private keys associated with each user, generating time varying codes, maintaining encryption software, maintaining audit trails and other functions may also be accomplished in a centralized fashion with the USR 10 for a plurality of organizations.

In one embodiment, following the connection of the access device 1802 to the secure system 1804, the USR 10 develops an audit trail by monitoring the communication path to capture information concerning the use of the secure system. For example, the USR 10 may collect and store information concerning the length of time during which the access device remains connected to the secure system, the type of resources accessed by the user, the type of data transmitted (including the identification of specific documents) during a login period and the volume of data transmitted.

According to one embodiment, the USR continuously monitors the communication between a plurality of access devices 1802 and a secure computer network and collects information to generate an audit trail for each device. According to another embodiment, the USR does not continuously monitor communications. Instead, the secure computer network intermittently (e.g., periodically) transmits audit information to the USR 10 where the audit information may concern one or a plurality of users connected to the network during a specific time period.

In each of the embodiments, described with reference to FIGS. 18A and 18B, the USR 10 may be located in an ultra-secure facility that employs heightened security relative to the security provided by the organizations that it serves. The physical facility where the USR is located may meet requirements generally associated with critical military installations. For example, the USR 10 may be housed in a facility that is hardened against radiation, shielded against electromagnetic interference, and/or protected against earthquakes, hurricanes, etc. to allow operation of the USR during times of general emergency. Further, the personnel and hiring policies of the facility operating the USR 10 may also be more secure relative to the security measures taken by the organizations associated with the secure systems 1804. That is, the individuals operating the USR 10 may undergo more rigorous background checks that include a detailed investigation of their personal and employment histories.

The centralized approach described above can provide increased security because the administration of the access control system (e.g., authentication software) is in the hands of a highly trusted third party who has taken heightened security measures regarding the hiring of the administrative personnel, in particular, the personnel who have access to authentication data (e.g., private encryption keys, etc.).

In any of the preceding embodiments, the USR 10 may be geographically remote from the secure systems.

Further, in any of the preceding embodiments, there may be situations where a user employs the access device 1802 to connect to more than one of the plurality of secure systems 1804. In one embodiment, the user is independently authorized to access separate secure systems 1804 associated with independent organizations. In another embodiment, the user is authorized to access separate secure systems 1804 each associated with the same organization. In either situation, the user may employ one or more of the authentication procedures described herein before being allowed access to any one of the secure systems 1804.

Figure 19:
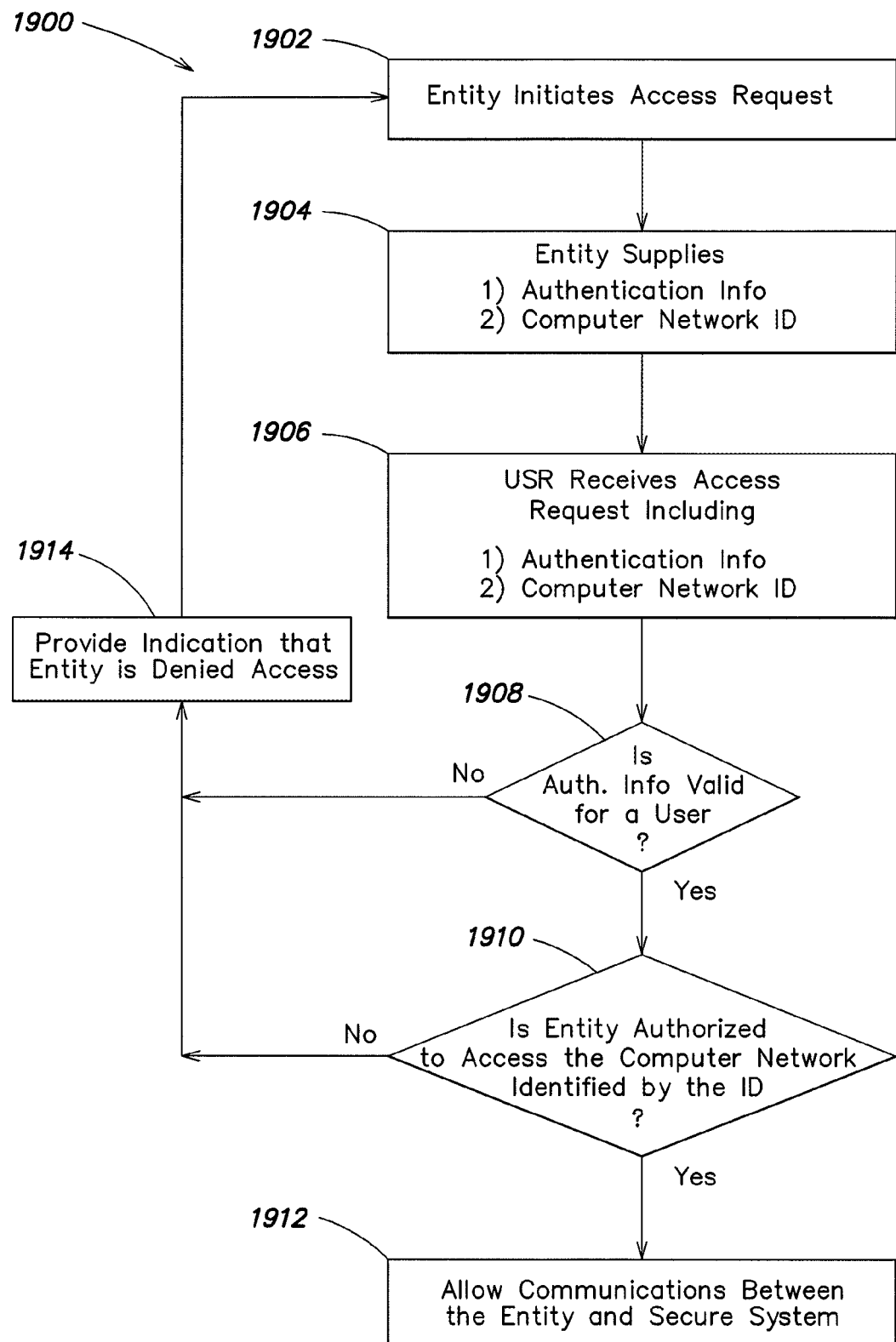
FIG. 19 is a flow diagram of a process for controlling access to a secure computer network with the USR system in accordance with an embodiment of the invention.

Referring now to FIG. 19, a process 1900 that employs a USR to control access to a secure computer network is illustrated. In one embodiment, the process 1900 is employed with the system 1800 illustrated in FIG. 18A. At step 1902 an entity initiates an access request. In general, the access request will be initiated when the user or entity inputs information into an access device such as a computer. At stage 1904, the entity supplies authentication information and a computer network ID to the USR (e.g., the information is electronically transmitted from the access device to the USR). According to one embodiment, the information is transmitted via the Internet from the access device to the USR. At stage 1906, the USR receives the access request which includes the authentication information and the computer network ID. At stage 1908, the USR determines whether the authentication information is valid for a user. According to one embodiment, the USR includes a database containing selected data of a plurality of users authorized to access a secure computer network, and may compare the authentication information supplied by the entity with authentication information included in the database to determine whether the authentication information corresponds or is valid for a user. If the authentication information is valid, the process 1900 moves to stage 1910 where the USR determines whether the entity is authorized to access the computer network identified by the computer network ID. If the entity is authorized to access the computer network then the USR may allow communication between the entity and the secure computer network at stage 1912. As previously indicated, the USR may route communications between the entity and the secure computer network and remain in the communication path employed by the access device to communicate with the secure computer network. Alternatively, the USR may simply provide a connection between the access device and the secure computer network where the communication path provided by the connection does not involve the USR.

Returning to stage 1908 if the authentication information supplied by the entity is not valid for any of the plurality of users then the process 1900 moves to stage 1914 where an indication is provided to the entity that access is denied. Similarly, if at stage 1910 the entity is not authorized to access the computer network identified by the computer network ID, an indication is provided that the entity is denied access at stage 1914. In various embodiments, the entity may be allowed additional opportunities to successfully access the system.

Figure 20:
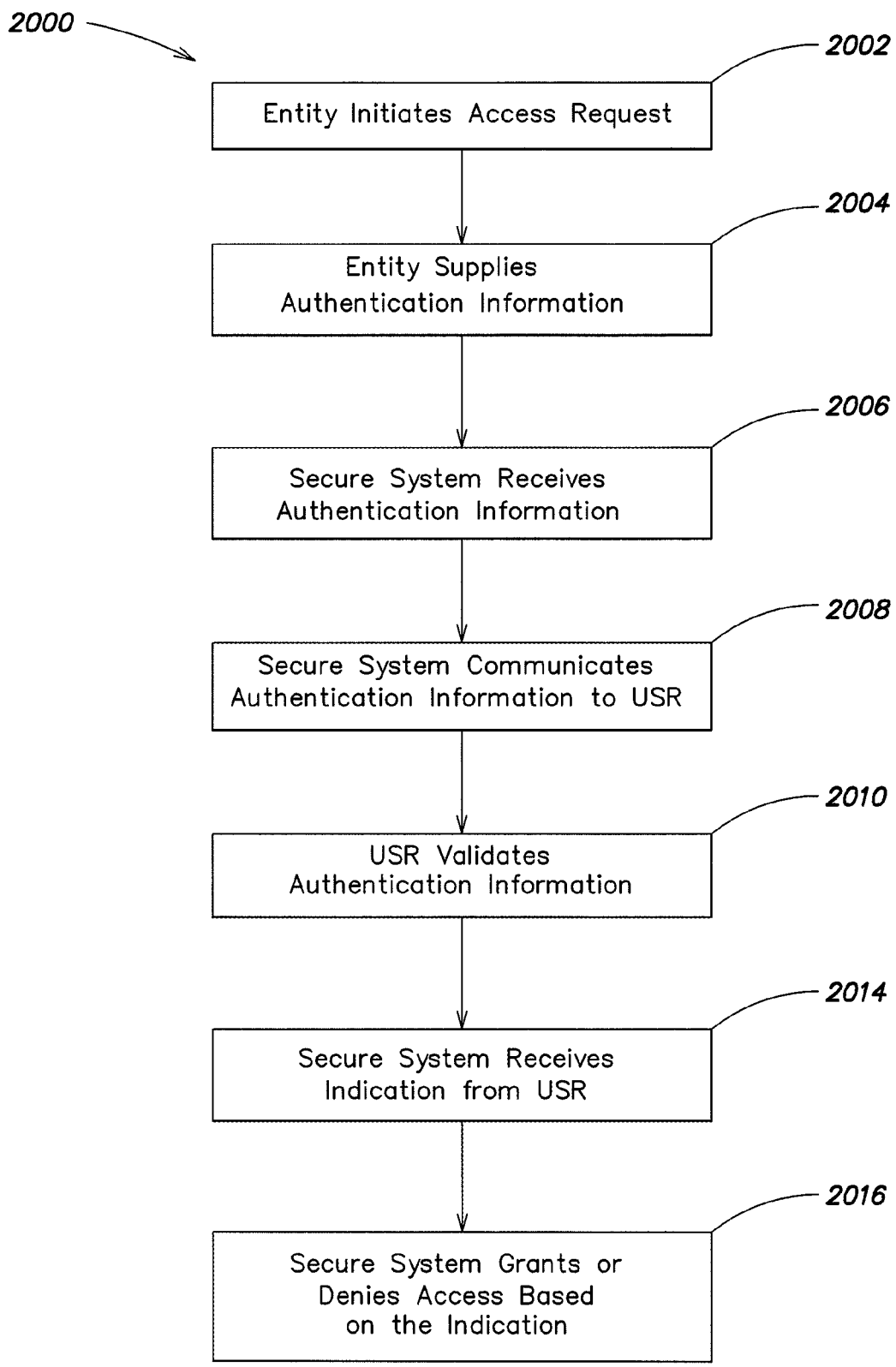
FIG. 20 is a flow diagram of a process for controlling access to a secure computer network with the USR system in accordance with another embodiment of the invention.

Referring now to FIG. 20, a process 2000 for controlling access to a secure computer network is illustrated in accordance with one embodiment. In one embodiment, the process 2000 is employed with the system 1810 illustrated in FIG. 18B.

In one embodiment the entity initiates an access request at stage 2002. As described above, the access request can be initiated using an access device and each secure computer network may communicate with a plurality of access devices. At stage 2004, the entity supplies authentication information to the secure computer network, for example, by entering the information in a web browser and transmitting the authentication information over the Internet to the secure computer network. At stage 2006, the secure computer network receives the authentication information. At stage 2008, the secure computer network communicates authentication information to the USR (or information corresponding to the authentication information) to allow the USR to authenticate the access request. At stage 2010, the USR validates the authentication information to determine whether the entity is authorized to access the secure system, and at stage 2014, the secure system receives an indication from the USR concerning whether the entity is authorized to access the system. In one embodiment, the indication is transmitted from the USR to the secure system via the Internet. At stage 2016, the secure system grants or denies the entity access to the secure system based on the indication received from the USR.

As should be recognized by those of ordinary skill, the processes 1900 and 2000 can be accomplished in a variety of stages that may include any of the stages described above in various combinations and sequences including one or more of the stages described above in combination with one or more additional stages.

Various embodiments can be employed to control access to a physical facility. That is, an electronic device (e.g., a keypad, a card reader, a biometric scanner, etc.) or combination of electronic devices can be located at an access point to a secure area (e.g., a door, a gate, etc.). The entity initiates the request using the electronic device. In one embodiment, the physical facility includes all or a portion of the secure computer network. Thus, in one embodiment, the secure system receives an indication of whether an entity is authorized to access a physical facility. The secure system communicates authentication information to the USR. The USR validates the authentication information and communicates an indication of whether the entity is authorized to access the physical facility. The secure system receives the indication and grants or denies the entity access to the physical facility.

Each of the embodiments described with reference to any FIGS. 18-20, may include a challenge-response protocol, for example, to authenticate the identity of the entity and/or the USR system to the other.

Figure 21:
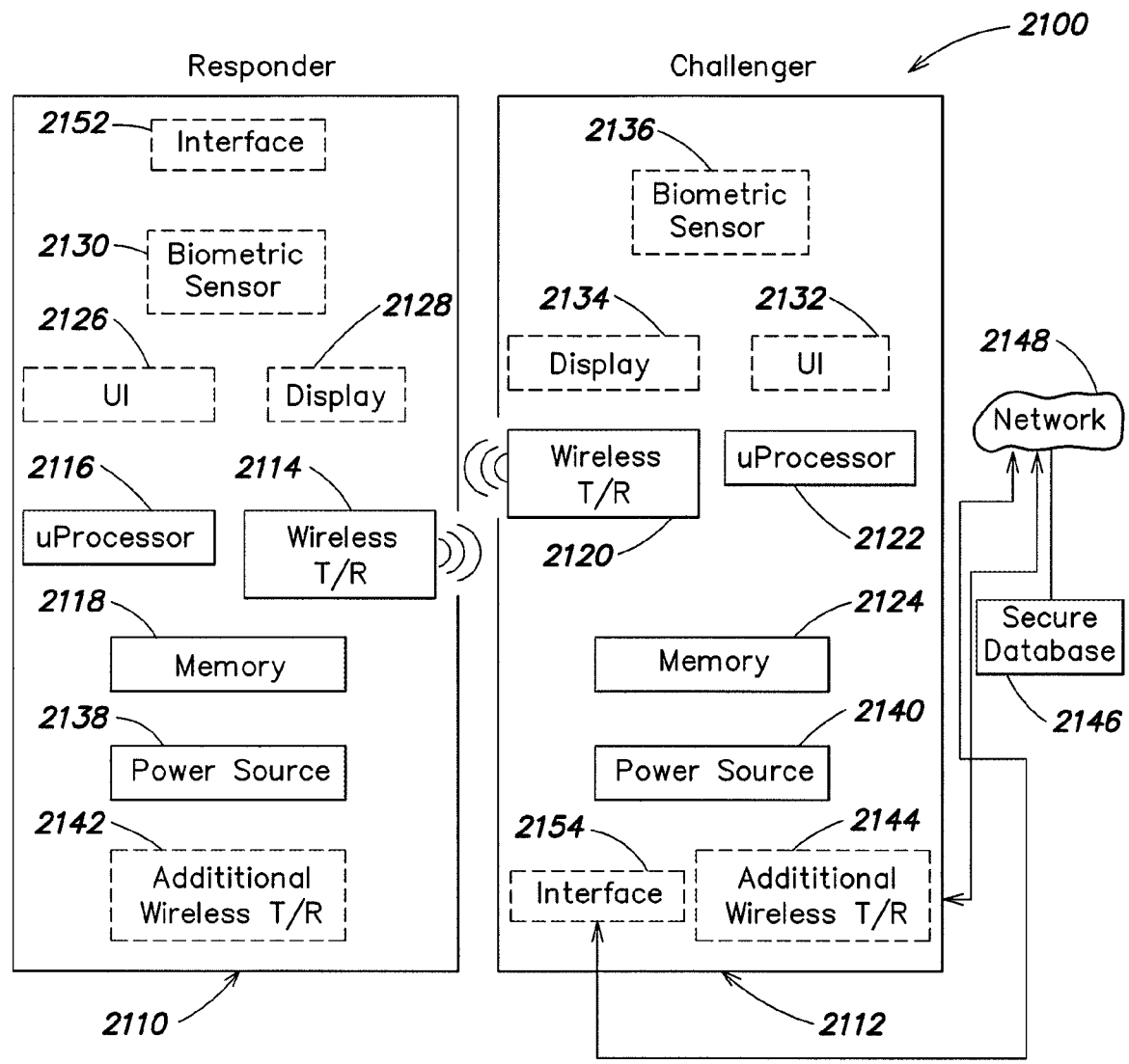
FIG. 21 illustrates an embodiment of a system for validating the identity of an individual.

FIG. 21 illustrates an embodiment of a system 2100 for validating the identity of an individual or an entity. The system includes a first wireless device 2110 and a second wireless device 2112. The first wireless device 2110 comprises a first wireless transmitter and receiver 2114, a first processor 2116 and a first memory 2118. Similarly, the second wireless device 2112 comprises a second wireless transmitter and receiver 2120, a second processor 2122 and a second memory 2124. According to aspects of the invention, the first wireless device and the second wireless device are configured to wirelessly communicate with each other so that the entity associated with the first wireless device can communicate his identity to the entity associated with the second wireless device. It is to be appreciated that the first wireless transmitter and the second wireless transmitter can be configured to communicate by any form of a wireless signal such as low power Bluetooth signal, infrared signals, RF signals and electromagnetic signals in general. In accordance with one embodiment, the first wireless device and the second wireless device communicate via near field signal.

The first wireless device can also comprise user interface 2126 that allows the first entity to interact with the first wireless device and can also comprise a display, such as a LCD display, 2118 that allows the first entity to further interact with the first wireless device. In accordance with some embodiments the invention, the first wireless device can be configured so that the first entity must enter a PIN identification number, for example, via the user interface to gain access to the wireless device. Alternatively, or in addition, the first wireless device may comprise a biometric sensor or detector 2130 that enable the first entity to present biometric data to the first wireless device to gain access to the first wireless device. For example, the biometric sensor can be configured to detect a fingerprint of the first entity. For such embodiment, the memory 2128 also comprises stored biometric data of the first entity, which is compared, for example, by the processor 2116 with the detected biometric data to determine whether the first entity is enabled or should be disabled from using the first wireless device. It is also to be appreciated that the biometric data need not be fingerprint data and can be any biometric data known to those of skill in the art, and that the biometric sensor need not be a fingerprint sensor and can be any biometric sensor known to those of skill in the art.

Similarly, the second wireless device 2112 can also be configured as discussed above with respect to the first wireless device, namely with any or all of a user interface 2132, a display 2134 and a biometric sensor 2136 and can be configured to require any and/or all of a second entity to provide a PIN number, or the second wireless device to match biometric information of the second entity with stored biometric information to enable or disable the second entity to gain access to the second wireless device. Each of the first wireless device 2110 and the second wireless device 2112 comprise a power source or a power source interface 2138, 2140 that can be coupled to a power source that provides power to respective devices. It is to be appreciated that the power source can be any power source, such as, alkaline batteries, rechargeable batteries, proprietary power sources, and interfaces to power sources such as standard 120 VAC, or an AC to DC conversion device, as well as any other type of power source known to those of skilled in the art. In addition, it is to be appreciated that each of the first wireless device 2110 and the second wireless device 2112 can also comprise an additional wireless transmitter and receiver device 2142, 2144, respectively, which enable each of these devices to communicate wirelessly via other wireless communication systems such as, via any cell phone standard, via satellite communications, over wireless area networks, local area networks, wide area networks, as well as any other wireless communication standard know to those of skill in the art.

According to some embodiments of the system 2100 of FIG. 21, either or both of the first wireless device 2110 and the second wireless device 2112 can be configured to communicate with a secure database 2146, as will be discussed in further detail herein. According to some embodiments, either of the first or second wireless devices may communicate with the secure database on a periodic basis to update its corresponding data, or to stay alive as will be discussed herein, or to retrieve information in the secure database that is used in the communication protocol between the first and second wireless devices to verify the identity of at least the first entity. Accordingly, it is to be appreciated that communication with a secure database can be, for example, via the additional respective wireless transmitters and receivers 2142, 2144 of the first and second wireless devices, or can be via a network interface 2152, 2154 of the respective devices, that communicate with a network 2148 and to the secure database 2146.

Figure 22A:
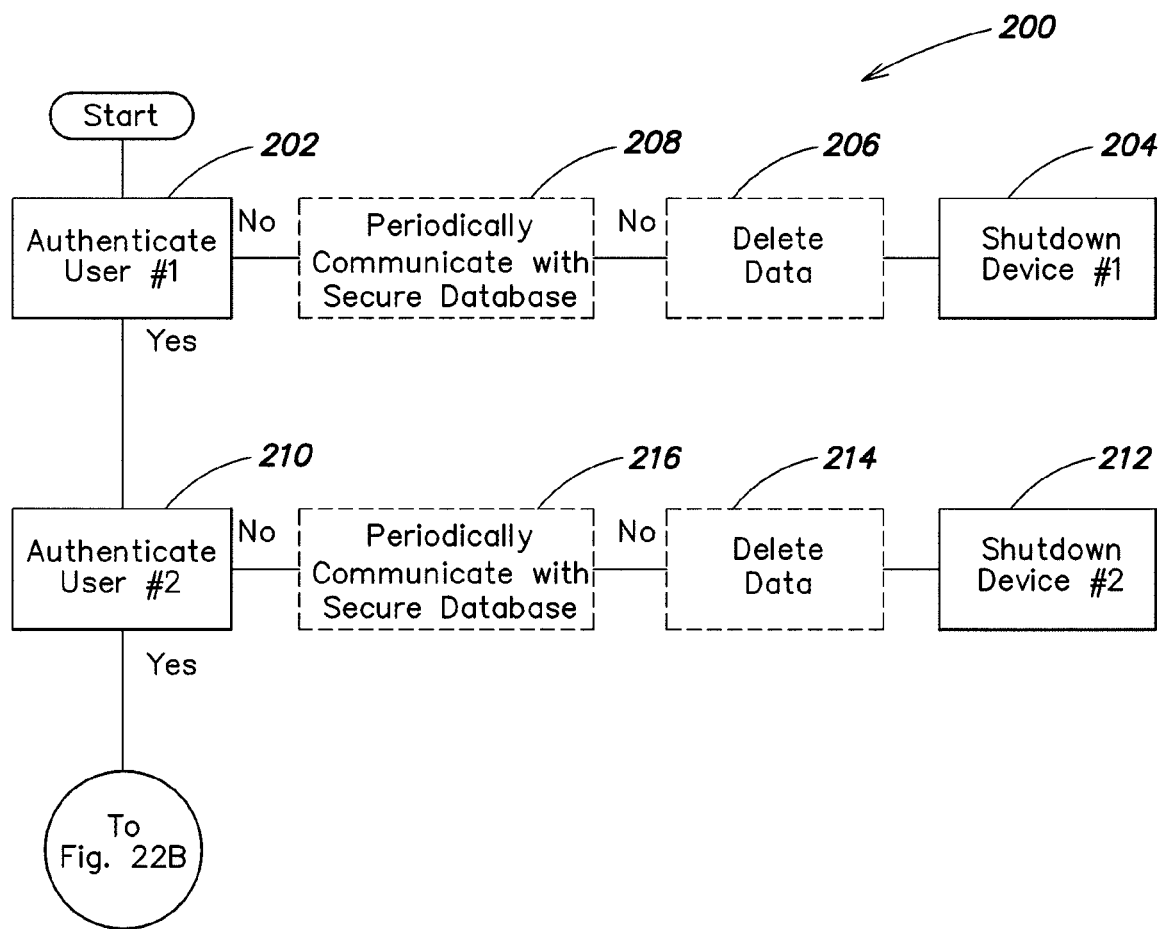
FIGS. 22A and 22B illustrate one embodiment of a process for validating the identity of an individual.
Figure 22B:
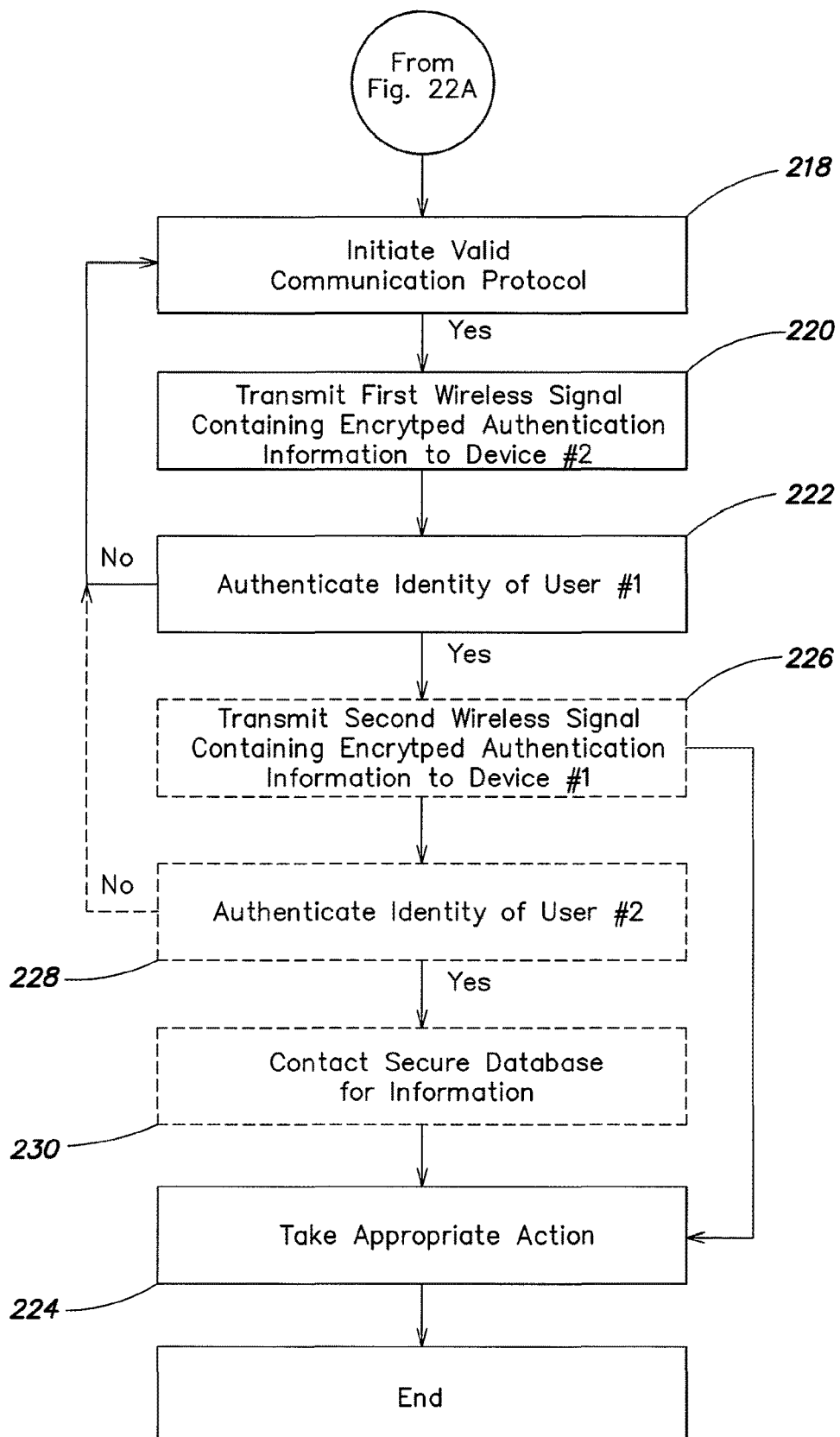

Referring now to FIG. 22, there is illustrated one embodiment of an overall communication process that occurs with the system 2100 of FIG. 21. In particular, the process is effected by the system of FIG. 1 so as to identify and authenticate the identity of the first user associated with the first wireless device 2110 to the second user associated with the second wireless device 2112. For example, consider the situation where an air marshal or an FBI agent is carrying the first wireless device 2110 and airport security or security personnel generally want to ensure the identity of the user of the device 2110. The communication protocol 200 illustrated in FIG. 22 is one embodiment of a protocol that enables secure authentication of the first user of the wireless device 2110.

According to one embodiment of the process, the first user of the first wireless device 2110 first authenticates his or herself to the wireless device 2110, for example as has been discussed above, by either entering a PIN via the user interface 2126 of the first wireless device or by interacting with the biometric sensor of the first wireless device at step 202. In various embodiments, a challenge-response protocol is employed in which the first user supplies information (a biometric, a PIN or other information) to authenticate his or herself to the wireless device 2110. If the user of the device does not enter the correct PIN number or does not match the biometric data stored in memory 2118 of the first authorized user of the device, then the device at a minimum shuts down at step 204. However, according to some embodiments, the device 2110 can also be configured to automatically delete any portion of or all of the data stored in memory 2118 at step 206. In addition, as will be discussed in further detail herein, according to some aspects of the invention, the first wireless device can be configured to periodically communicate with the secure database 2146 to remain alive, for example, after the first user of the first device authenticates itself to the first device. If the first device does not communicate with the secure database at such periodic intervals at step 208, then the first device can be configured to delete any or a portion of the data stored in memory at step 206.

The communication protocol also comprises a second user of the second device to authenticate his or herself to the second device at step 210. It is to be appreciated that the authentication by the second device of the second user by any of the mechanisms discussed herein and above with respect to the first wireless device, including entering a PIN number to the user interface 2132 of the second wireless device or by interacting with the biometric sensor 2136 of the second wireless device. In addition, it is to be appreciated that as discussed above with respect to the first wireless device, if such identification is not successful, the second wireless device will at a minimum shut itself down at step 212. However, it is also to be appreciated that the second wireless device can be configured to automatically delete a portion of or all of the data stored in the memory 2124 of the second wireless device, should such authentication not be successful at step 214. In addition, it is to be appreciated that the second wireless device can also be configured at step 216 to communicate with the secure database 2146 within defined periods of time, or even a periodic interval once the second user authenticates himself to the second wireless device, and to delete a portion of or all of the data in memory 2124 should such periodic communication not occur.

If both the first user and the second user are successful in authenticating themselves to the first and second wireless devices respectively, then a communication protocol is initiated between the first wireless device 2110 and the second wireless device 2112 at step 218. If the communication protocol is not a valid communication protocol between the devices, the devices wait until there is a valid communication protocol. If the communication protocol is a valid protocol (218 yes), then the first wireless device transmits a first wireless signal containing encrypted authentication information of the first user to the second wireless device 2112 at step 220. The details of the communication protocol and the encrypted authentication information will be discussed further herein.

The second wireless device 2112 receives the first wireless signal and processes the wireless signal to determine the identity of the first user. In particular, as will be discussed herein, according to some aspects of the invention, the authentication of the first user includes displaying a picture of the first user to the second user on the display 2134 of the second wireless device as a result of the communication from the first wireless device to the second wireless device. The user of the second wireless device can view the picture on the display and ascertain whether the first user of the first wireless device is who he or she purports to be. However, as will also be discussed herein, it is to be appreciated that the second wireless device need not be a device that requires a user to interact with it and can be, for example, an unmanned detection system that receives the first encrypted authentication information and determines from the first authenticated encrypted information whether the first user is authorized to gain access to a secured place, a secure network, or a secure computer, to do whatever the first person is seeking to do. If the first user is not who they purport to be, the communication process goes back to look for a valid communication protocol. In addition, the process allows the second user or the system associated with the second wireless device to take an appropriate action such as denying access to the secure site at step 224.

If the user of the first wireless device is authenticated (at step 222 yes), then according to some aspects of the invention, the communication process allows for the second wireless device to transmit a second wireless signal comprising encrypted authentication information of the second user to the first wireless device at step 226. In addition, according to such aspects, the communication protocol and the first wireless device are configured to authenticate the identity of the second user to the first user at step 228. It is to be appreciated that the authentication of the second user to the first user can be in any of the manners discussed above with respect to the authentication of the first user of the first device, such as by viewing a picture of the second user as provided on the display 2128 of the first wireless device, by matching one-time information contained in the encrypted authentication information or via a challenge-response protocol.

In addition, according to some embodiments of the protocol, either or both of the first wireless device 2110 and the second wireless device 2112 may communicate with the secure database 2146 to retrieve additional information at step 230. Such information, as will be discussed herein, can include for example, a portion of the biographic data of the first user of the first wireless device or of the second user of the second wireless device, or full biometric information of the first user or the second user, which can be communicated back to the respective device and used by the respective device to authenticate the user. In addition, the information can be periodic updates as provided the secure database to the respective device, such as will be described herein, including periodic updates of public keys of a plurality of first users as stored in memory on the second wireless device, or updates to public keys of a plurality of second users as stored in memory on the first wireless device. In addition, such information may include periodic updates of the biometric information of a plurality of first users as stored on the second wireless device or a plurality of second users as stored on the first wireless device, which can comprise for example a portion of the biometric information or all of the biometric information.

Figure 23:
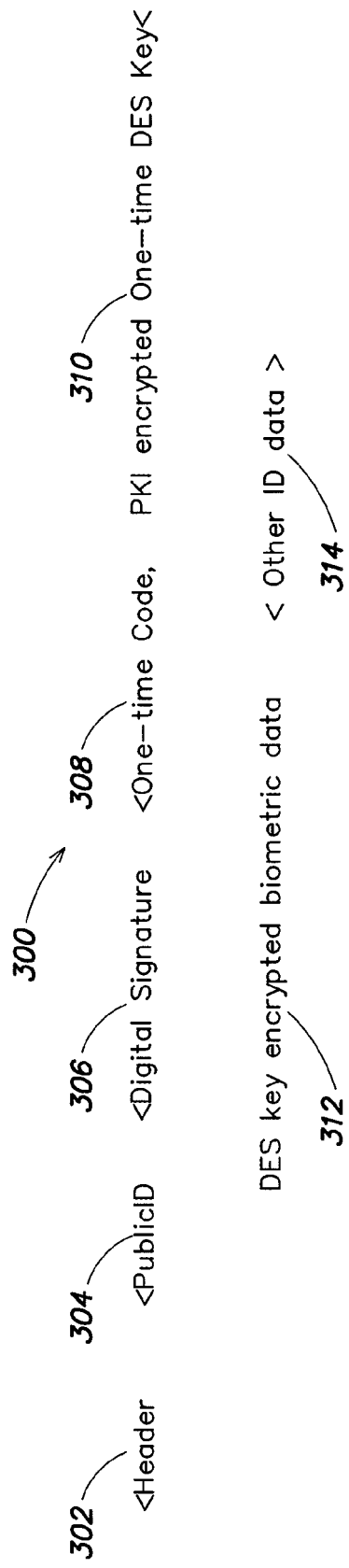
FIG. 23 illustrates one embodiment of various fields included within a first wireless signal and a second wireless signal as transmitted by the system of FIG. 21.

Referring now to FIG. 23, there is illustrated one embodiment of various fields included within the first wireless signal and the second wireless signal as transmitted between the first wireless device and the second wireless device. According to some embodiments, the signal comprises a header field 302. The header field can be any header field known to those of skill in the art. In addition, the signal comprises a public ID field 304, which can comprise, for example, any of name information, a badge number, an employee number, an e-mail address, a social security number, and the like, of the first user. In addition, the first wireless signal may also include a digital signature field 306 containing a digital signature of the first user. For example, the digital signature may be generated with the user's private PKI key. Further, the first wireless signal may comprise a one-time time varying code field 308 that includes a random code as generated by the first wireless device. According to some embodiments, the digital signature field and the one-time code field can be used, for example by the second wireless device, to allow access to a secure place without the need for a user of the second wireless device to interact with the second wireless device to authenticate the first user. As an example, referring to FIG. 24, the digital signature and one time code can be encrypted with the private key of the first user and transmitted to the second wireless device. The second wireless device can decrypt the digital signature and one time code with the public key of the first user at steps 402-404 to authenticate or not the first user at step 406.

In addition, referring back to FIG. 23, the first wireless signal also comprises a PM encrypted one-time DES key field 310 comprising a PM encrypted one-time DES key. Further, the first wireless signal comprises a DES key encrypted biometric data field 312, which includes at least a portion of biometric data of the first user encrypted with the DES key. As will be discussed in further detail herein, according to some aspects of the invention, the public key of a first user, for example, stored in memory 24 of the second wireless device can be used to decrypt the DES key, and the DES key can be used to decrypt at least a portion of the biometric data of the first user to use in the authentication of the identity of the first user. According to some embodiments, the first wireless signal can also comprise another ID data field 314, which can contain other information such as name, height, weight, eye color or anything else.

It is to be appreciated that although the embodiment of the wireless signal discussed in FIG. 23 has been discussed with reference to the first wireless signal transmitted from the first wireless device 2110 of FIG. 21 to the second wireless 2112, that the same protocol can be used when transmitting a second wireless signal from the second wireless device 2112 to the first wireless device 2110 to authenticate the identity of the user of the second wireless device to the user of the first wireless device. It is to be further appreciated that various fields of the signal can be used and not all of the fields of the wireless signal are needed to authenticate identity of the user.

Figure 24:
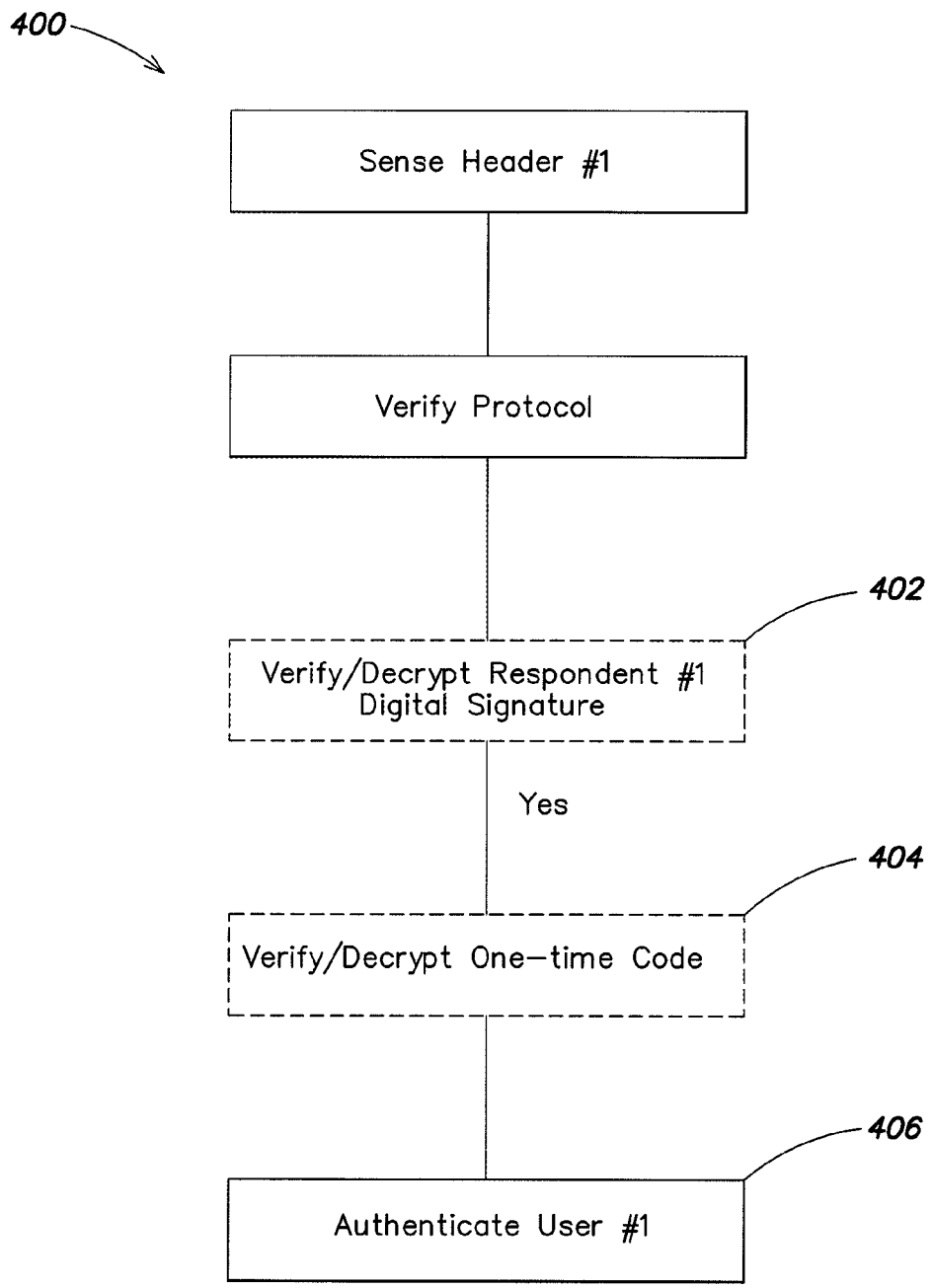
FIG. 24 illustrates one embodiment of a process for verifying or authenticating the identity of a first user of a first wireless transmission device.

Referring now to FIG. 24, there is illustrated one embodiment of a process 400 as identified by act 222 in FIG. 22 for verifying or authenticating the identity of the first user of the first device. According to this embodiment, which has been briefly discussed herein with respect to FIG. 23, the second wireless device can verify the identity of the respondent without necessarily interacting with a second user by decrypting the first user's digital signature from the digital signature field 306 at step 402 and verifying that it is the digital signature of the first user, decrypting the one-time code from the one-time code field 308 at step 404, and using this information at step 406 to authenticate the first user. If the first user is authenticated at 406, an appropriate action such as allowing access to the secure site, or computer, or network can be granted.

Figure 25:
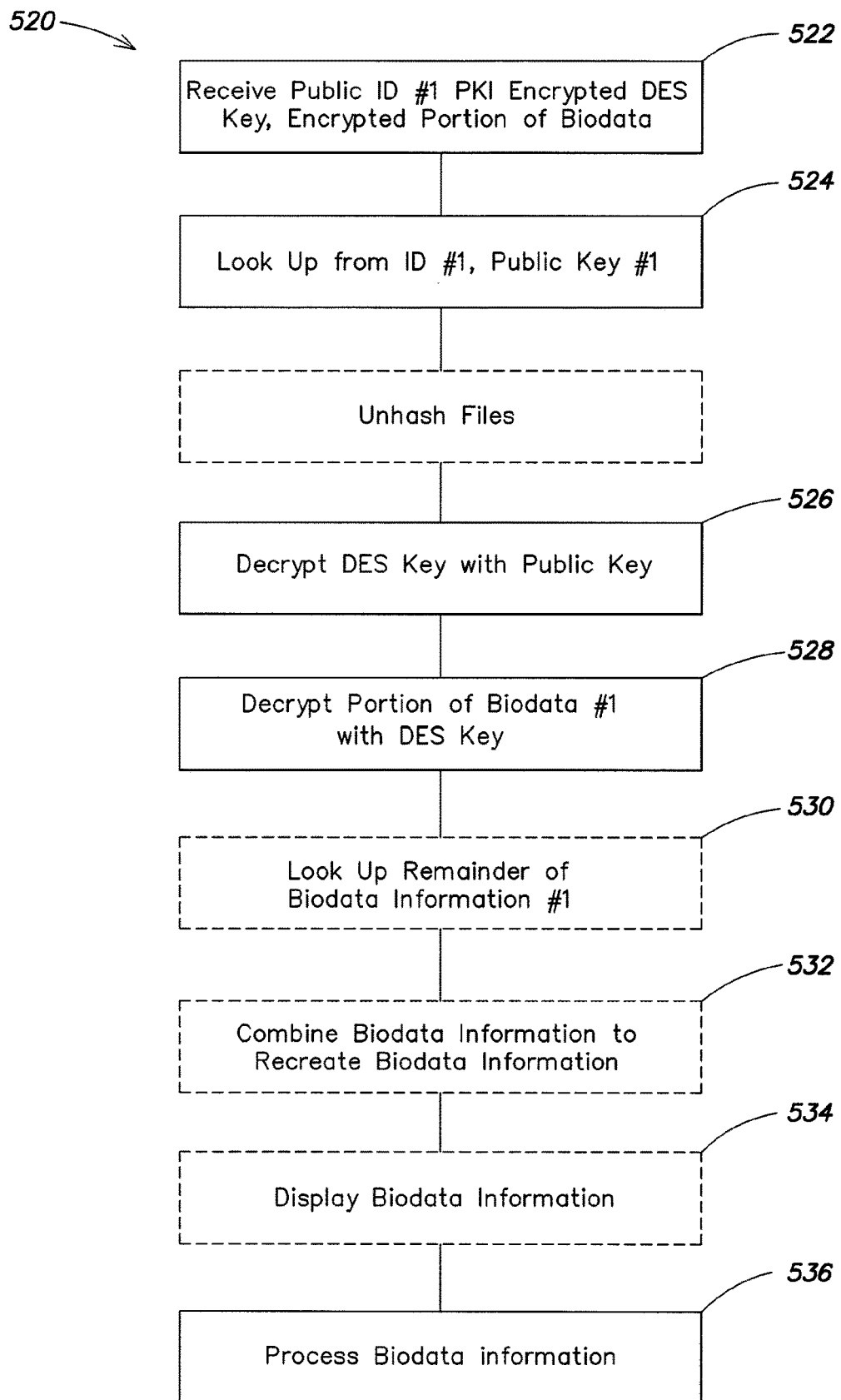
FIG. 25 illustrates another embodiment of a process for authenticating the identity of a first user of a wireless transmission device.

Referring now to FIG. 25 there is illustrated another embodiment of a process 520 for authenticating the identity of the first user at step 222 of the communication process of FIG. 22. According to aspects of the invention, the second wireless device at step 522 receives the first wireless signal and extracts the PKI encrypted DES key from field 310. The wireless device looks up the public key of the first user from memory 2124 [See FIG. 21] or from a secure server based on the information provided in the public ID field 304 at step 524. The second wireless device uses the first public key to decrypt the PM encrypted DES key at step 526. The second wireless device acts on the DES key encrypted biometric information from the field 312 and uses the decrypted DES key to decrypt the at least a portion of the biometric information of the first user as included in the first wireless signal at step 528.

According to some embodiments, the biometric information included in the first wireless signal is a portion of the biometric information of the first user and the second wireless device is configured to store a remainder of the biometric information of the first user in memory. According to such embodiments, the process 520 also comprises looking up the remainder of the biometric information stored in the memory at step 530 and combining the remainder of the biometric information with the decrypted and extracted biometric information to provide complete biometric information of the first user at step 532. According to some aspects of the invention, the biometric information can comprise a digital image of the first user and for such aspects, the digital image can be displayed on display 2134 of the second wireless device so that the second user can ascertain whether the first user associated with the first device is who he or she purports to be. However, it is to also be appreciated that the biometric information can be fingerprint information, a voiceprint, DNA codes of the first user, or any other biometric information known and used by those of skill in the art. Accordingly, the processor 2122 of device 2112 can also be configured to process the combined biometric information to authenticate the first user at step 536.

Figure 26:
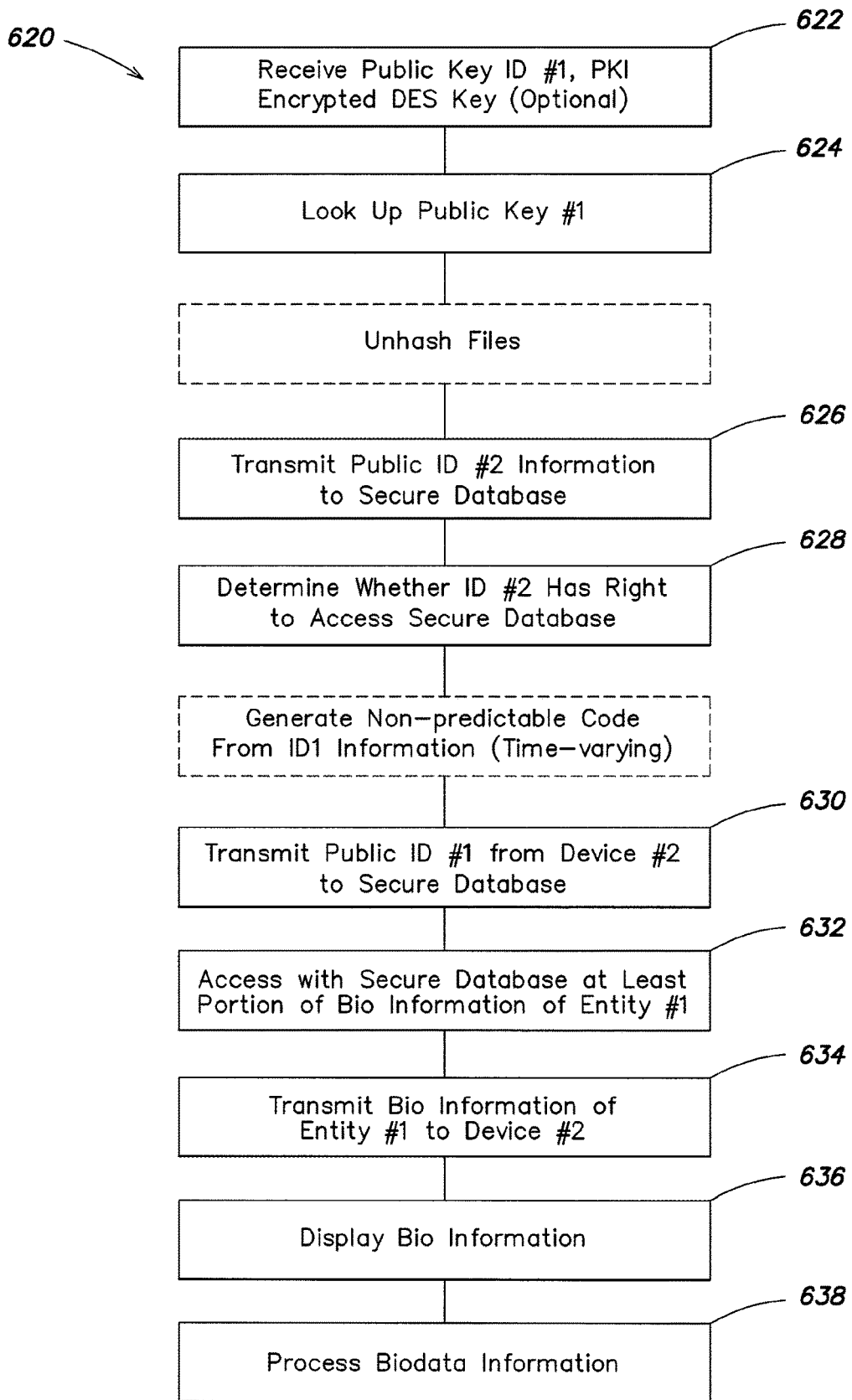
FIG. 26 illustrates still another embodiment of a process for authenticating the identity of a first user of a wireless transmission device.

Referring now to FIG. 26, there is illustrated another embodiment of a process 620 that can be used to authenticate the identity of the first user at step 222 of the process 200 of FIG. 22. According to this embodiment, some of the steps are similar to the steps of the process 520 illustrated in FIG. 25 and accordingly a full description of these steps will not be herein duplicated. It is to be appreciated that this embodiment can be used for example, where the biometric information of the plurality of first users is not stored on the second wireless device 2112 but is instead stored at the secure database 2146 as illustrated in FIG. 21. In particular, for highly secure applications, where there is a worry that the second wireless device can be compromised (even with the necessity to authenticate the second user to the second wireless device), the second wireless device can be configured to interact with the secure database to obtain at least a portion of the biometric information of the first user, rather than storing at least a portion of the biometric information of the first user in memory on the second wireless device.

According to such embodiments, the second wireless device can receive the first wireless signal including the fields discussed above in respect to FIG. 23, in particular, the public ID field 304 and optionally the PKI encrypted DES key. According to some embodiments, the PM encrypted DES key may be used by this process. At step 624, the second wireless device accesses public key information of the first user from the public keys stored in memory on the second wireless device. However, it is to be appreciated that in some embodiments, the public keys may not be stored on the second wireless device. For such embodiments, the second wireless device will communicate with the secure database to obtain the public key of the first user also at step 624. According to some embodiments, at step 626 the second wireless device transmits a signal to the secure database comprising public identification number to identify the second device to the secure database, presumably after the second user of the second device has authenticated his or herself to the second device. For such embodiments, at step 628, the secure database determines whether the second device is authorized to access the secure database at step 628. It is to be appreciated that according to some embodiments, this communication between the second wireless device and the secure database can be accomplished with encrypted signals and in some embodiments the encrypted signals can include using time varying one time codes to further secure the communication. If the second device is authorized to interact with the secure database, the process also comprises transmitting the first public ID from the second wireless device 2112 to the secure database at step 630, and with this information, the secure database accesses the biometric or identification information of the first user at step 632. The biometric or the at least a portion of the biometric information can then be transmitted by the secure database to the second wireless device at step 634. Again, this transmission can be encrypted and further include time varying or one time codes to further secure the communication. The second wireless device can use the received portion of the first biometric information and combine it with portion of the first biometric information provided in the first wireless signal, or can receive all of the first biometric information as provided by the secure database and, for example, display it on the display 2134 of the second wireless device 2112 at step 636, or can process the biometric or identification information at step 638 to determine whether the first user is authenticated.

Figure 27:
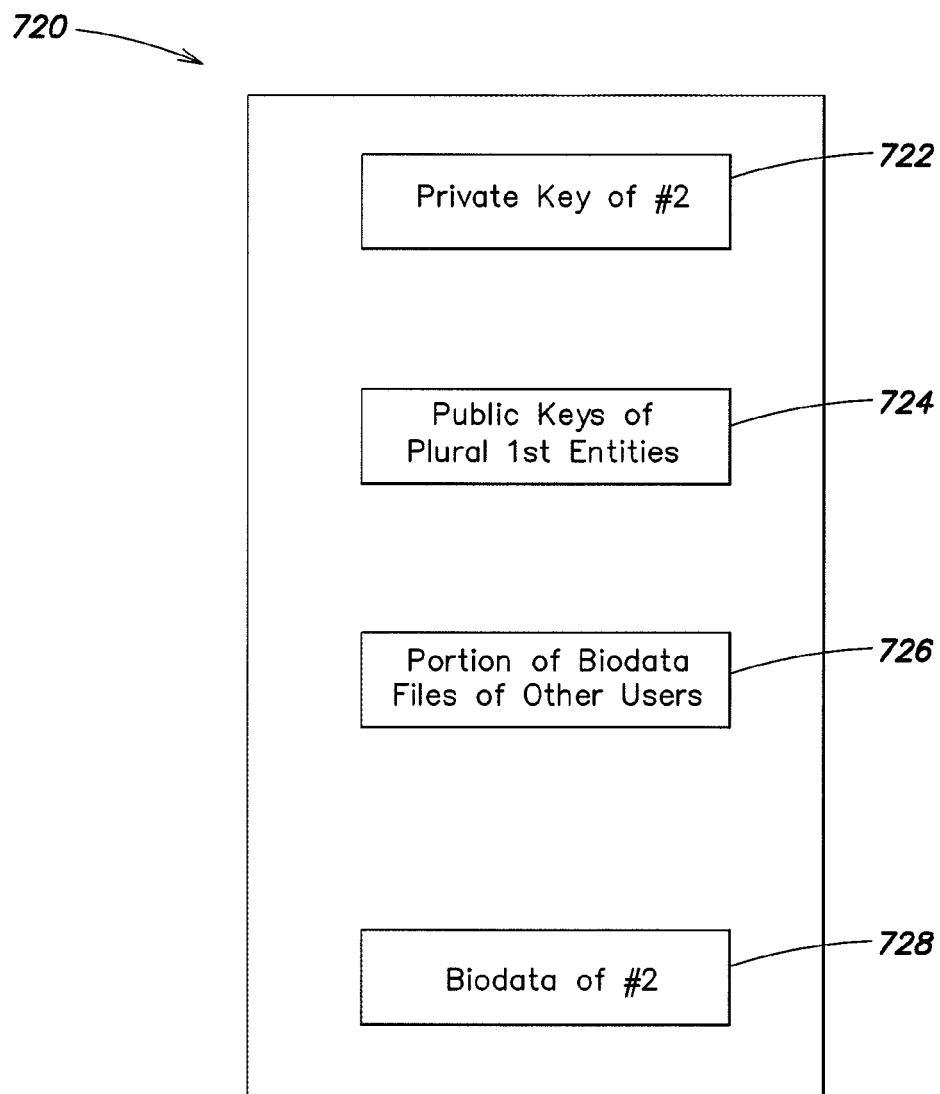
FIG. 27 illustrates one embodiment of a data structure that can be used by any wireless device of the system of FIG. 21.

Referring now to FIG. 27 there is illustrated one embodiment of a data structure 720 that can comprise memory 2124 of the second wireless device 2112. It is to be appreciated that any or all of the various portions of this data structure can be present in the memory 2124. According to some aspects of the invention, the memory will include the private key of the second user at field 722. The private key can be used, for example, when communicating by the second wireless device to the first wireless device to provide a digital signature of the second entity encrypted with the second user's private PM key to the first user. In addition, the memory can also comprise a plurality of public keys of a plurality of first users at area 724. Such public keys of a plurality of first users can be used as has been discussed herein in combination with the private key of the first user to decrypt information of the first user. For example, the public and private key can be used to decrypt the DES key of the first user. In addition, the memory can also comprise at least a portion of biometric data of a plurality of first users, at area 726. As been discussed herein, the at least a portion of the biometric data of the plurality of first users can be combined with the portion of the biometric data provided in the first wireless signal or from the secure database, to create the complete biometric data of the first user for ascertaining or authenticating the identity of the first user as has been described herein. In addition, the memory can also comprise biometric data of the second user at field 728. The biometric information of the second user can be used, for example, as has been discussed herein to compare the biometric data detected by the biometric sensor 2136 of the second wireless device to determine whether the second user is authorized to have access to the second wireless device. It is to be appreciated that the data structure 720 of FIG. 27 can also comprise the memory 2118 of the first wireless device 2110, and that any or all of the fields of the data structure 720 can exist in the memory 2118 in the first wireless device. It is also to be appreciated that the first wireless device can access the data structure 720 and the various fields for the same purposes as discussed above with respect to the second wireless device, namely, to provide the first digital signature of the first entity encrypted with the first private key in the first wireless signal, to access the public keys of a plurality of second users for the purpose of decrypting information provided in the second wireless signal, to access at least a portion of biometric information of the second user stored in the field 726, as well as to compare biometric information of the first user with sensed biometric data provided by the biometric sensor 2130 of the first wireless device.

In one embodiment, the method comprises acts of receiving first authentication information about the first entity with the first device, transmitting the authentication information about the first entity to a secure database, determining whether or not the first entity is allowed to access the first device based on the first authentication information, and transmitting an enablement signal to the first device indicating to enable nor not enable the first entity to access the first device. According to a further embodiment, the method also includes an act of allowing or not allowing operation of the first device based on the enablement signal. In another embodiment, the act of receiving the first authentication information of the first entity comprises receiving biometric information of the first entity by detecting the biometric information with the first device.

In yet another embodiment, the act of transmitting the first authentication information about the first entity to a secure database comprises generating a non-predictable signal from the biometric information. In a further embodiment, the act of generating the non-predictable signal from the biometric information comprises generating a time varying non-predictable signal from the biometric information. In a still further embodiment, the act of receiving biometric information of the first entity comprises receiving a voice signature of the first entity with the first device and the act of generating the non-predictable signal from the biometric information comprises mixing the voice signature of the first entity with a random code to generate the non-predictable signal. In yet a further embodiment, the act of transmitting the enablement signal to the first device comprises sending the random code to the first device. In a still further embodiment, the act of receiving biometric information of the first entity comprises receiving fingerprint data of the first entity with the first device and the act of generating the non-predictable signal from the biometric information comprises mixing the fingerprint data of the first entity with a random code to generate the non-predictable signal. In another embodiment, the act of transmitting the enablement signal to the first device comprises sending the random code to the first device.

In a further embodiment, the act of authenticating the biometric of the first entity comprises authenticating a voice signature of the first entity. In another embodiment, the act of authenticating the biometric information of the first entity comprises authenticating a finger print of the first entity.

In one embodiment, a first wireless device includes a biometric detector comprising a fingerprint detector that detects a fingerprint of the first entity. In an alternate embodiment, the biometric detector comprises a voice signature that detects a voice signature of the first entity.

According to one embodiment, the system comprises a first wireless device including a processor configured to enable operation of the first wireless device if it receives an enablement signal validating first biometric information of a first entity and configured to generate a non-predictable signal from the biometric information, a first wireless transmitter and receiver configured to transmit a first wireless signal including first encrypted biometric information of the first entity and to receive the enablement signal, a first biometric detector for detecting the first biometric information of the first entity and a secure database configured receive the first wireless signal, to authenticate or not authenticate the first biometric information of the first entity, and to provide the enablement signal validating or not validating the first biometric data of the first entity.

In a further embodiment, the secure database further comprises biometric data of a plurality of first entities. In another embodiment, the processor is configured to generate the non-predictable signal from the biometric information by generating a time varying non-predictable signal from the biometric information. In a still further embodiment, the processor is configured to generate the non-predictable signal from the biometric information by mixing the biometric information of the first entity with a random code to generate the non-predictable signal. In yet another embodiment, the secure database is configured to transmit the enablement signal to the first device including the random code so as to authenticate the secure database to the first device. In still another embodiment, the system includes a memory for storing a private key of the first entity authorized to use the first device.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

Figure 28:
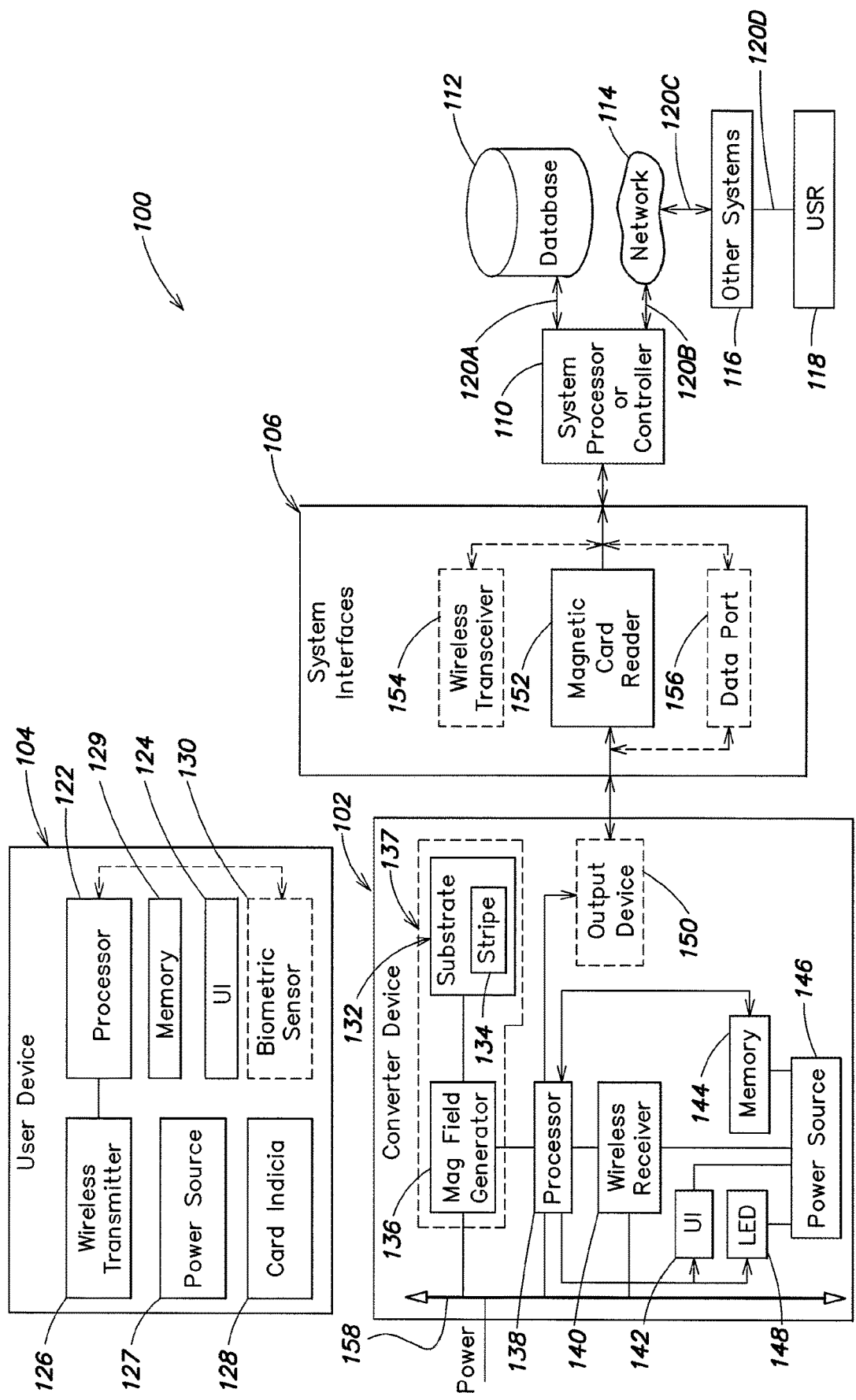
FIG. 28 illustrates a system in accordance with one embodiment of the invention.

FIG. 28 illustrates an embodiment of a system 100 that employs a converter device 102 to provide an interface between a user device 104 (e.g., a transaction card, a cell phone, etc.) and a system interface 106 where, for example, the system interface 106 employs a magnetic card reader and the user device 104 is not equipped with a magnetic stripe. That is, in one embodiment, the converter device 102 provides a mode of information transmission between the user device 102 and the system interface 106 which would otherwise be unavailable to the user device 102. The converter device 102 provides a modified system 100 that provides compatibility with a greater variety of user devices, for example, user devices such as transaction cards, cell phones or PDAs that are not equipped with a magnetic stripe. For example, in one embodiment, the converter device 102 includes a magnetic stripe emulator 137 communicatively coupled to a wireless signal receiver 140 and adapted to provide a time-varying signal emulating data provided by a magnetic stripe card to a magnetic card reader 152.

The user device need not be a "card" and may, for example, take the form of a fob used as a key ring, a cell phone, a watch, a personal digital assistant or any device that can include a wireless transmitter, or a magnetic stripe emulator.

In various embodiments, the user device 104 employs near field signal to communicate with the converter device 102. In one embodiment, the near field communication is bi-directional such that the user device 104 may both send and receive wireless communication. That is, the user device includes a transceiver.

In general, the system interface 106 provides an interface to a larger information system (e.g., a financial system, an access control system, a medical records system, and the like) that in one embodiment includes a system processor or controller 110, a database 112, a network 114, other systems 116, such as a universal secure registry 118 as will be described further herein. Each of the preceding system elements may be placed in communication with any one or any combination of the system elements, for example, over communication links 120A, 120B, 120C, 120D. It should be recognized that the communication links 120 need not provide the communication paths shown in FIG. 28 and that other communication paths may be employed. For example, the database 112 may be connected to the network 114 via the communication link 120A and to the system processor 110 via the communication link 120B instead of being connected as shown in FIG. 28.

The communication link may be a wireless communication link, a hardwired communication link, a fiber optic communication link, any communication link used in the art, as well as a combination of any of the preceding or any other any communication link capable of transmitting signals between the elements of the system 100. The system processor 110 allows information transfer of both data and instructions, for example, between the interface 106 and one or more databases which may be connected to the system or other network elements.

In general, the operation of the converter device 102 allows a user in possession of the user device 104 to wirelessly communicate information to the device so that the device can be employed to interface with a network system. For example, in one embodiment, the network system may provide a magnetic card reader interface and the converter device 102 provides a magnetic stripe emulator that can interface with the system. In general, the overall operation of the system 100 includes the communication of information between the user device 104 and the converter device 102, for example, RF communication. In one embodiment, the communication is bi-directional such that information can be communicated both to and from the user device 104. The converter device 102 provides an interface by which information derived from the information being transmitted to or from the user device 104 is transmitted between the converter device and the system interface 106. The system interface 106 provides the communication interface between it and the remainder of the system 100 (e.g., processor 110, database 112, network 114, etc.).

According to one embodiment, the user device 104 includes a processor 122, a user interface 124, a wireless transmitter 126 and device indicia 128. In another embodiment, the user device 104 includes a biometric sensor 130. In various embodiments, the processor 122 is communicatively coupled to each of the wireless transmitter 126, the user interface 124 and the biometric sensor 130.

The processor 122 may include a chip such as a general purpose processor, an application specific integrated circuit ("ASIC"), or a field programmable gate array ("FPGA") and the like that may execute various programs and/or provide logic inputs and outputs. For example, the processor 122 may process biometric information received from the biometric sensor 130 to verify the identity of the user before the user can employ the user device 104. Exemplary details of a processor and biometric sensor which are configured to authenticate a fingerprint of a user are disclosed in U.S. published application 2004/0133787, published on Jul. 8, 2004, which is herein incorporated by reference in its entirety. The processor 122 may also include or be coupled to driver circuitry to drive a display included in the user interface 124 and can be configured to process user input data entered via the user interface 124. In one embodiment, the user interface 124 includes one or more control inputs (for example, control buttons).

The wireless transmitter 126 can process information provided by the processor and convert the information to an RF signal and can also include an RF antenna that transmits the RF information wirelessly. In another embodiment, the user device may also include an RF receiver that receives a wireless RF signal from the RF antenna and converts the RF signal to an information signal provided to the processor. It is to be appreciated that the wireless transmitter and/or receiver need not be an RF device; it can also be any of an IR device, an optical device, a Bluetooth signal or any other wireless signal transmitter or receiver used in the art.

The user device may also include a power source such as a battery that fits within the device. In one alternative embodiment, the user device remains in a sleep mode until it is placed in the vicinity of an RF transmitter at which time the user device 104 converts received RF energy into electrical energy used to provide power to the processor 122 and the other components included in the user device 104.

According to one embodiment, the user device 104 can be a smart card configured for wireless signal transmission using RF signals. For example, the wireless transmitter 126 may be an RF transmitter device or any other wireless transmitter device configured to transmit the smart card information of the card. Alternatively, it is to be appreciated that the card can be many cards such as a debit card, a plurality of credit cards such as VISA, MasterCard, American Express, or any other card with the card indicia and relevant information being stored in card memory 129 and read out by processor 122 and provided to the wireless transmitter 126. However, the user device 104 need not be in the form of a card and may instead include a cell phone or PDA.

In the embodiment illustrated in FIG. 28, the converter device 102 includes a substrate 132 which may include a stripe 134 and a magnetic field generator 136 which together comprise the magnetic stripe emulator 137, a processor 138, a wireless receiver 140, a user interface 142, a memory 144, and a power source 146. In a further embodiment, the converter device 102 includes an indicating light 148 (e.g., an LED) and an output device 150.

According to one embodiment, the system interface 106 with which the converter device 132 is employed includes any of or all of a magnetic card reader 152, a wireless transceiver 154 and a data port 156.

In general, according to one embodiment, the converter device 102 receives a wireless signal from the user device 104, processes the information that is received and provides an output in the form of a time-varying signal provided to the stripe 134 (e.g., a magnetic stripe). The signal provided to the stripe 134 can then be provided to the system processor 110 by inserting the stripe and the associated substrate 132 or portion thereof in the magnetic card reader of the system interface 106. That is, in one embodiment, the stripe 134 and at least a portion of the substrate 132 can be either slid by the magnetic card reader 152 or inserted to sit statically in front of the read head of the card reader.

The processor 138 may be a general purpose processor, an application specific integrated circuit ("ASIC"), or a field programmable gate array ("FPGA") and may be implemented in hardware, software, firmware or any combination of the preceding. The processor 138 may be communicatively coupled with any of the magnetic field generator 136 the wireless receiver 140, the memory 144, the user interface 142, the light source 148, the power source 146 and the output device 150. In general, the processor can be configured to receive inputs from one or more of the preceding elements and may provide outputs to each of the elements included in converter device 138.

For example, according to one embodiment, the magnetic stripe 134 is a programmable magnetic stripe and the magnetic field generator 136 generates a magnetic signal that controls the information provided by the magnetic stripe 134. The U.S. patent application Ser. No. 10/680,050, filed Oct. 7, 2003, entitled "System Method and Apparatus for Enabling Transactions Using a Biometrically Enabled Programmable Magnetic Stripe which was published on Jul. 8, 2004 as US2004/0133787 (the '050 application), provides further details concerning embodiments of the user device that emulates a magnetic stripe and may also include, for example, a biometric sensor. The '050 application is incorporated herein by reference in its entirety. In this embodiment, the processor 138 may control the operation of the magnetic field generator 136 to provide the desired information to the stripe 134. For example, the processor 138 may provide an output to the stripe 134 in response to receiving information from the wireless receiver 140, where the information from the wireless receiver is information transmitted from the user device 104.

Further, the processor 138 may be configured to provide signals to drive a display included in the user interface 142 and process user input data entered with the user interface 142. In one embodiment, the user interface 142 includes a display screen that can be used to display an image of the user to whom the user device 104 belongs, for security purposes. The image to be displayed by the UI can either be part of the information transmitted by the user device 104, for example, where the user device 104 also requires some authentication by the user before transmitting the device information and image, or can be provided, for example, by the USR system 118 through the system interface 106 as part of the user authentication process, as will be described in more detail herein. In further embodiments, the user interface 142 may include a plurality of control elements that allow the user and/or the transaction processor (e.g., store clerk, security guard, medical service provider, etc.) to enter information into the converter device 102. According to one embodiment, the user interface 142 includes an LCD display.

The processor 138 may also be configured to provide signals to operate the indicating light 148. The indicating light 148 may provide an indication of the operational status of the converter device 102, for example, the indicating light 148 may indicate any of the following: that the converter device 102 is receiving a transmission from a user device 104; that the converter device 102 has generated output data to the stripe 134; the status of the power source 146 is normal or conversely that the power source has a low power level; that the converter device 102 is transmitting information via the output device 150; that the converter device 102 is properly aligned with the magnetic card reader 152; that the converter device 102 has received authorization for a transaction; and the like. It should be apparent to one of skill in the art that the indicating light may be a single lamp or a plurality of lamps and that the lamp or lamps may be a single color including white or may include a plurality of colors. Further, it should also be apparent that the lights may provide a plurality of status indications based on their color, intensity, rate of change of the preceding characteristics or any combination of these and other features.

The power source 146 may include a battery power source or other energy sources suitable for the form factor of the converter device 102. For example, in a form factor where the converter device 102 is a hand-held device the power source 146 may be any one of a standard size battery (e.g., a AA battery). In a further embodiment, the power source is a lithium battery. Alternatively, the power source can be any of an AC power source, an AC to DC converter device, or any other DC power source known to those skilled in the art.

According to one embodiment, the converter device 102 includes a power bus 158 that provides a path for the transmission of power to the various components included in the converter device 102.

In accordance with one embodiment, the converter device 102 includes the output device 150. It is to be appreciated that the output device can be any standard interface device to be coupled to a data bus such as a USB device, or the output device can be configured for contactless communication with the system interface 106. For example, in one embodiment, the output device is an optical transmitter device. In general, the communication between the converter device 102 and the system interface 106 is bi-directional such that information (e.g., information associated with the user's identity) may be transmitted to the system interface 106, the system processor 110 may generate a response (e.g., a transaction approval), and the response may transmitted to the converter device 102 via the system interface 106.

In one embodiment, the processor 138 is configured in combination with the output device 150 to provide an encrypted output signal. In a further embodiment, the processor 138 is configured in combination with the output device 150 to provide a time-varying encrypted output signal. In yet another embodiment, the processor 138 is configured in combination with the output device 150 to provide a time-varying encrypted (or not) public and private key output signal. In addition, the processor can also be configured in combination with the wireless receiver to receive and decrypt any and all of an encrypted signal, a time-varying encrypted signal and a signal encrypted with a private key as provided by the user device 104. A challenge-response protocol may also be employed alternatively or in addition to any of the preceding.

For example, embodiments of the invention may employ a protocol that does not require synchronized clocks in each of the user device 104 and the converter device and/or elsewhere in the system 100 to complete a validation and/or authentication process. That is, according to one embodiment, an information exchange between the user device 104 and the converter device 102 includes a first piece of information transmitted from the user device 104 to the converter device 102 and a subsequent challenge (e.g., an encrypted challenge) generated by the converter device and transmitted from the converter device to the user device 104. According to one embodiment, the user employs the user device to respond to the challenge. In one embodiment, the user's response is at least in part based on information included in the challenge. An identity of a user who responds accurately to the challenge can be successfully validated. In various embodiments, a challenge-response protocol includes an information exchange whereby the identity of the converter 102 is also authenticated by the user with the user device 104.

In various embodiments, the above-described challenge-response protocol may not require any further action by the user than is required under current approaches that require synchronized clocks in disparate devices.

In some embodiments, the output device 150 need not transmit any personal information associated with the user. For example, commonly owned U.S. patent application Ser. No. 09/810,703, filed Mar. 16, 2001, entitled "Universal Secure Registry" ("the '703 application") describes an approach that can improve security and reduce the need for multiple forms of identification. The '703 application is incorporated herein by reference in its entirety. The universal secure registry 118 included in the system 100 provides one example of the integration of such a registry into a system that employs a converter device 102. With the USR system, for example, the user device 104 can provide some information, e.g., such as a public code of the user, which can be authenticated by the user, for example by providing an ID through the user interface 124 or through biometric sensor 130. The public code can be provided to the USR via the converter 102, system interface 104, and network 114. The USR can then provide back to any of the system interface and the converter device any or all of device information (e.g., transaction card information), authorization for a transaction, e.g., where the network or the USR also communicates with the relevant authority, and indicia about the holder of the user device.

The system 100 may include a variety of system interfaces 106 of different types such as the wireless transceiver 154 and the data port 156 in addition to the magnetic card reader 152. Although not illustrated, other system interfaces such as an optical interface, a smart card reader interface or any other system interface known to those of skill in the art can also be included. Further, the system interfaces may be either commonly located or may be geographically distributed such that some locations include a wireless transceiver 154, some locations include a data port 156, some locations include a magnetic card reader 152, and some locations include a plurality of types of system interfaces.

Thus, in some embodiments the output device 150 of the converter device 102 may include a data port via which the converter device 102 can provide data to a network or a networked device. In one embodiment, the data port is also configured to receive data from the network or a networked device.

Embodiments of the converter device 102 can be configured to provide communication to the system interface 106 via any of the preceding approaches including wireless signal transmission. In a version of this embodiment, the converter device 102 may receive wireless signals from the user device and transmit wireless signals to the system interface 106. Further, the converter device may include a transmitter that allows it to transmit information back to the user device.

Figure 29:
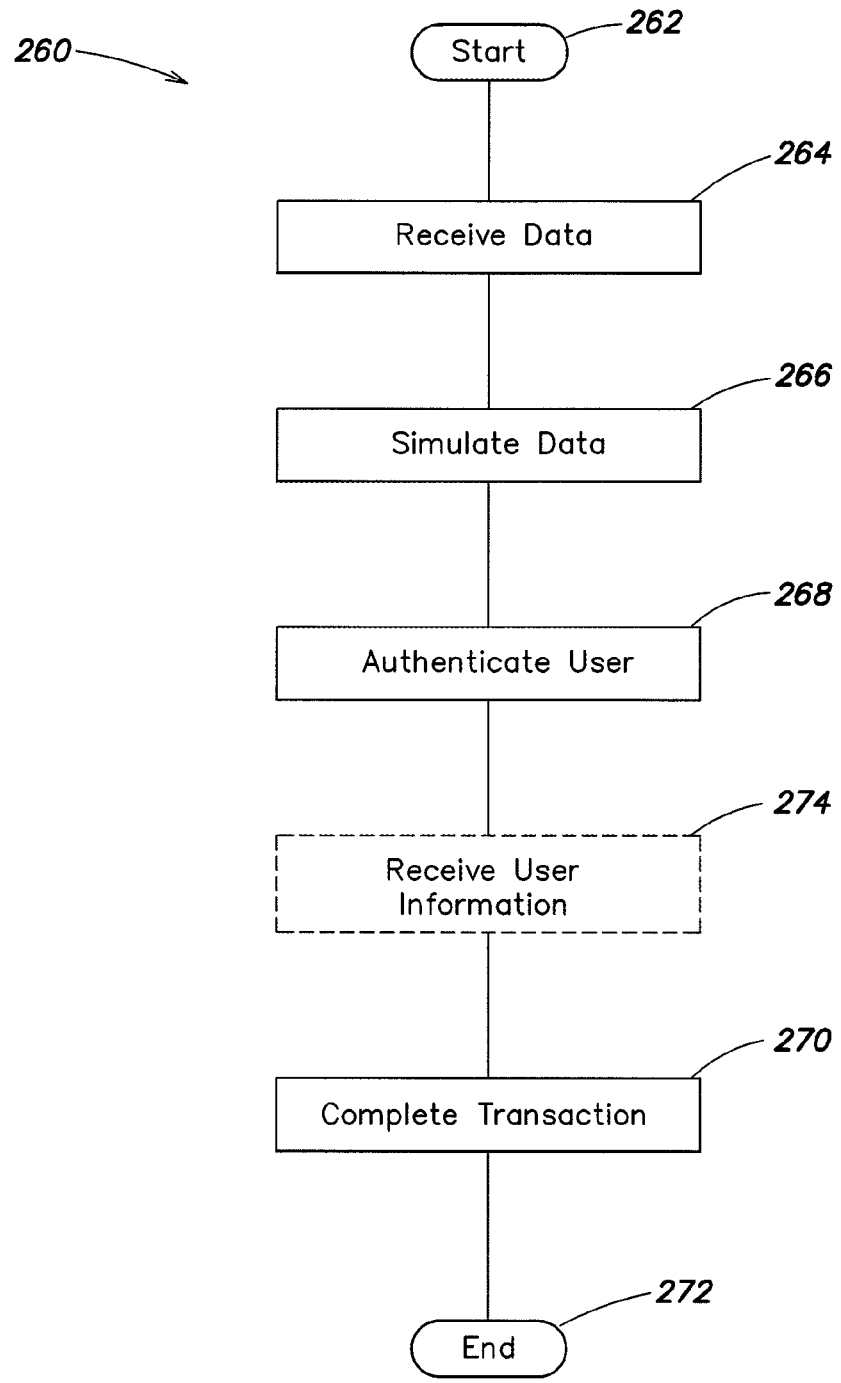
FIG. 29 illustrates a process in accordance with an embodiment of the invention.

Referring now to FIG. 29, a process 260 employing the converter device 102 is illustrated in accordance with one embodiment. The process begins at Stage 262—START. Here, the converter device 102 is in a steady state in which it awaits receipt of a signal from a user device 104. At Stage 264, the converter device 102 receives data, for example, a wireless signal transmitted from the user device 104. At Stage 266, the converter device 266 extracts information from the wireless signal for processing. As one example, the converter device 102 may extract information corresponding to the user's identity and/or the identity of the individual to whom the user device was issued. The extracted information is then provided to the system interface, for example, it is simulated as magnetic striped data to the magnetic card reader. At Stage 268, the system 100 authenticates the user. In one embodiment, if the authentication is successful, the process continues at Stage 270. In this embodiment, if the authentication is unsuccessful, the process returns to Stage 262 where, for example, the user may be prompted to attempt to authenticate again.

Various user authentication approaches may be implemented using the converter device 102. For example, the authentication may be performed locally, that is, without the need for communication between the converter device 102 and the system interface 106 and system processor 110. In one embodiment, the authentication process employs the universal secure registry 118. In further embodiments, the authentication process employs one or more authentication protocols such as public-key cryptography, key exchange protocols, protocols employing one-way functions, and the like that are well known by those of ordinary skill in the art. In other embodiments, however, the authentication may require an exchange of information between the converter device 102 and any of the system interface 106, the network 114, the USR 118 and another database 112. A challenge-response protocol may also be employed alternatively or in combination with any of the preceding authentication approaches.

At Stage 270, the completion of the transaction may be involve any of a wide variety of acts including: authorizing a withdrawal of money from a user's account, permitting the user access to a secure area, permitting a user to view medical information concerning themselves or a third party, or permitting the user to access other confidential information.

In addition, in some embodiments, the process 260 includes Stage 274 where following authentication the converter device 102 receives information associated with the user. The information may, for example, be necessary for the completion of the transaction. For example, where the system 100 is employed in conjunction with a check-authorization process, the converter device 102 may receive an indication that the user has sufficient funds to cover the amount of the check that is presented at a point of sale. Alternatively, or in addition, the information may include indicia related to the authorized holder of the user device 104, such as a picture ID. The process 260 is completed at Stage 272—END. An embodiment, of the converter device 302 is illustrated in FIGS. 30A through 30D.

Figure 30A:
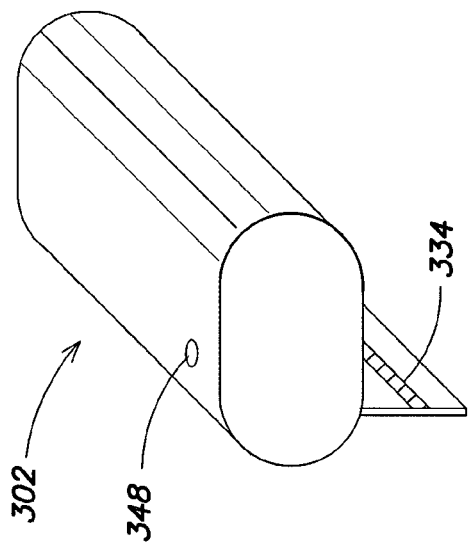
FIGS. 30A-30D illustrate a converter device in accordance with one embodiment of the invention.
Figure 30B:
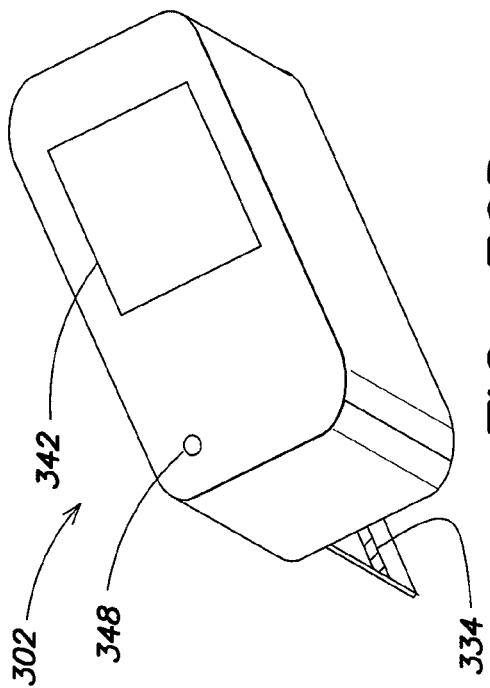
Figure 30C:
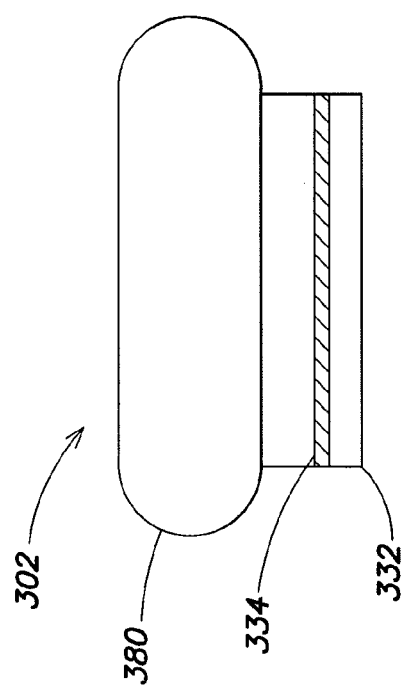

As illustrated in the front view of FIG. 30A, in one embodiment, the converter device 302 includes a housing 380, a substrate 332, and a magnetic stripe 334. In one embodiment, the housing 380 is manufactured from a rigid material, for example, metal or plastic and the converter device 302 is designed to be a hand-held device. FIG. 30B illustrates a side view perspective of an embodiment of the converter device 302, showing an indicating light 348 (e.g., an LED). As described in greater detail above, the indicating light 348 can include a single indicating light or a plurality of indicating lights.

FIGS. 30A-30D illustrate an embodiment where the substrate extends substantially perpendicular from a side of the housing 380, however, the specific angle at which the substrate extends from the housing may vary so long as the housing does not interfere with the insertion of the substrate into, for example, the magnetic card reader 152.

Figure 30D:
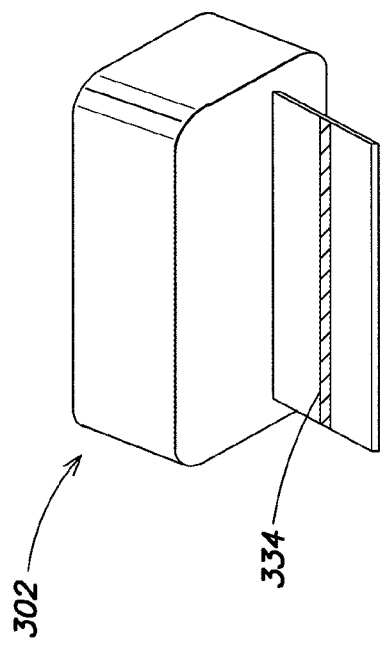

FIG. 30D illustrates a top view of an embodiment of the converter device 302 which includes a display screen (e.g., an LCD display screen) that may provide the user interface 342 or a portion of the user interface of the converter device 302. In one embodiment, the user interface 342 includes a display screen that displays either a black and white or a color image of the individual to whom the user device 104 was issued. It should be recognized that the display screen may provide a wide range of functionality, for example, the display screen may display a variety of data received by the converter device 302 including data represented in alpha numeric format.

The magnetic stripe 334 may be a programmable magnetic stripe such that the converter device 302 provides a magnetic stripe emulator. In one embodiment, as has been described herein, the converter device 302 receives a wireless signal from a user device 104 and provides a time varying signal which emulates data provided by a magnetic-stripe card to a magnetic card reader in response to receiving the information from the wireless signal. In a further embodiment, the information is provided to the magnetic card reader by inserting the magnetic stripe 334 into the magnetic card reader.

The various embodiments of a system and method for converting a wireless transaction device to a magnetic stripe emulator device may include any of the following or any combination of the following: a converter device with a processor communicatively coupled to a wireless signal receiver and to a magnetic stripe emulator. The converter device may optionally include an LED. Further the processor may be configured for any combination of the following: control of the LED to indicate that the device is properly aligned with the magnetic card reader, control of the LED to indicate that the device has received authorization for a transaction, and where the converter device includes a power supply, a processor configured to control the LED to indicate that the device has power.

In one embodiment, the information received from the wireless signal by the converter device may include any of a name, a card number, user identification, a device code, amount of credit available, and an expiration date of the card for a transaction.

Further, in various embodiments, the converter device may include an output device that can provide information to a network or to a networked device. In various embodiments, the output device can be configured as a wireless transmitter device, such as an optical transmitter device.

In various embodiments the wireless transmitter device where the wireless transmitter may generally be configured as an RF transmitter device, and in particular, as a Bluetooth transmitter device.

In addition, in various embodiments, the processor can be configured in combination with the output device to provide any of an encrypted output signal, a time-varying encrypted output signal, and in particular, a time-varying public and private key output signal.

In further embodiments, the converter device may include an output device configured as a data port via which the converter device can provide data to a network or a networked device and to receive data from the network or a networked device.

In one embodiment, the converter device may also include an LCD screen for displaying at least some of the data received by the converter device, and a processor configured in combination with the LCD device to display indicia corresponding to the authorization of a transaction, and in particular, indicia that includes picture information of the cardholder.

In addition to the above described features, the various embodiments of a system and method for converting a wireless transaction device to a magnetic stripe emulator device may include any combination of the following or any combination of the following and the above listed features: the converter device can be configured to communicate with the magnetic card reader via the data port; the wireless receiver and/or processor is configured to decrypt an encrypted wireless signal; the converter device is configured to decrypt a time-varying encrypted wireless signal; the converter device configured to decrypt time-varying public and private key information contained within the wireless signal; the converter device includes a user interface communicatively coupled to the processor; the converter device processor is configured to determine whether the user is authorized to provide the information contained within the wireless signal from data provided through the user interface.

In addition, the following further additional features may be combined alone or in combination with the preceding: the data contained within the wireless signal received by the converter device may include any combination of the following: user I.D. information, biometric information of the user, secret information, (for example, a PIN, a password, or a passcode of the user), or information about an uncounterfeitable token of the user.

In various embodiments, the converter device may include a substrate housing the magnetic stripe emulator, and the substrate may include a programmable magnetic stripe.

In various embodiments, the system employed with the converter device may also include a system interface coupled to a network where the system interface includes a magnetic stripe reading device configured to read a time-varying signal. In a further embodiments, the system interface may be configured to transmit data received from the wireless transaction device to a networked credit card authentication entity also coupled to the network. The system may also include any of a keyboard, a printer, an (LCD) display, and an audio signal transducer.

Although the preceding description is primarily directed to an embodiment of the user device 104 that does not include a magnetic stripe, it should be recognized that some embodiments of the user device 104 may include a magnetic stripe. In these various embodiments, the converter device 102 may be employed to convert information coded on the magnetic stripe for transmission via another mode of information transmission.

As described above, various embodiments allow a user to employ a mobile phone or other device as a token to assist the user in securely accomplishing a variety of operations. Some embodiments also allow the user to employ the token in combination with a USR system to increase the utility of the token and the functionality and security of the various operations. That is, the token may be employed to assist the user in conducting operations that access data concerning commercial transactions (for example, retail purchases), finance and banking operations, medical records and medical information systems, physical security and access control, and identification and authentication of the parties involved in any of the preceding, etc.

Referring now to FIG. 31, a system 350 is illustrated for use in facilitating financial transactions in accordance with some embodiments. As used herein with reference to FIG. 31, the term "financial transaction" can include any of sales transactions including transactions conducted on-line or at a point of sale using credit or debit accounts, banking transactions, purchases or sales of investments and financial instruments or generally the transfer of funds from a first account to a second account. The system includes a user device 352, a point-of-sale ("POS") device 354 and a universal secure registry 356 which can communicate with one another wirelessly, and/or over a network 357.

According to one embodiment, the user device 352 includes a display 362, a user interface 364, a communication link 366 and a biometric sensor 367. In various embodiments, the user device 352 may be any of a mobile phone, a personnel digital assistant or other handheld device.

In various embodiments, the communication link 366 may include any of a receiver and a transmitter suitable for wireless communication such as via RF and/or optical signals. Accordingly, in some embodiments, the communication link 366 includes an antenna and/or an optical signal source such as a LED alone or in combination with an optical receiver. In accordance with one embodiment, the user device 352 can employ an optical signal in the infrared spectrum. In various embodiments, the user device 352 can be configured to communicate by any form of a wireless signal such as a Bluetooth signal, WiFi, near field communication, ultra-wideband communication, RF signals and electromagnetic signals in general.

In some embodiments, the biometric sensor 367 may be employed to receive and process biometric inputs such as any of or any combination of a fingerprint, a speech/voice input, an iris scan, a retina scan, a facial scan, a written input, the user's fingerprint and DNA. In a further embodiment, the biometric sensor can be employed to process a written input that includes a signature.

In addition, various embodiments of the user device 352 may be in the form of a smart card or other type of credit card as described previously. Further, in some embodiments, the user device 352 may include an embodiment of the first wireless device 2110 illustrated in FIG. 21. Accordingly, in various embodiments, the user device 352 can include all or some of the features and functionality found in the first wireless device 2110. That is, the user device 352 can include features that may not be illustrated in FIG. 31, for example, a microprocessor, memory, a power source, etc. In yet another embodiment, the first wireless device 2110 can be employed to conduct transactions in accordance with the embodiment illustrated in FIG. 31 and described below.

In general, the POS device 354 may be any type of POS device as known to those of ordinary skill in the art. In accordance with some embodiments, the POS device 354 includes a display 368, a user interface 370 and a communication link 372. Further, in some embodiments, the user device may include an embodiment of the second wireless device 2112 illustrated in FIG. 21. Accordingly, in various embodiments, the POS device 354 can include all or some of the features and functionality found in the second wireless device 2112. That is, the POS device 354 can include features that may not be illustrated in FIG. 31, for example, a microprocessor, memory, a power source, a biometric sensor, etc. In yet another embodiment, the second wireless device 2112 can be employed to conduct transactions in accordance with the embodiment illustrated in FIG. 31 and described below. Further, it should be apparent to those of skill in the art that the POS device may be a handheld device or a larger "countertop" device. It should be also apparent to those of skill in the art that the POS device may communicate wirelessly with the network or may be coupled to the network 357 via a hardwired connection.

In accordance with one embodiment, the network 357 includes a plurality of networks that may allow communication between any of the user device 352, the POS device 354 and the USR 356 over any communication medium including wired networks (including fiber optic networks) or wireless networks. Further, the network may include one or more of either or both of local area networks and wide area networks including the Internet. In general, the network 357 can be employed for communication between the user device 352 and the USR 356, communication between the user device 352 and the POS device 354, communication between the POS device 354 and the USR 356, and communication between the user device 352 and the USR 356 via the POS device 354. According to the illustrated embodiment, the system 350 may also include a network 374 that allows communication between the user device 352 and the POS device 354 but does not provide communication with the USR. A wireless personal area network such as Bluetooth provides one example, while a local WiFi network, near field communication and ultra-wideband communication provide further examples of various embodiments of the network 374. As should be apparent to those of ordinary skill in the art, however, the network 357 may include any of the preceding in accordance with some embodiments.

Further, in accordance with some embodiments, the user device 352 may wirelessly communicate with a converter device, for example, the converter device 102 described with reference to FIG. 28. According to this embodiment, the converter device is used to communicate with the POS device 354, for example, where the POS includes a magstripe reader.

According to one embodiment, the USR 356 includes a secure database that stores account information for a plurality of users 358. In a further embodiment, the USR 356 retains records concerning one or more accounts 360 for each of the plurality users so that in effect the USR 356 in the system creates a secure wallet that allows a user of the device 352 to select a particular account from among a plurality of accounts associated with the user for use in a selected transaction. The type of account can vary in accordance with various embodiments. In accordance with one embodiment, the accounts 360 are credit card accounts, for example, any of those serviced by VISA, MasterCard, Discover and American Express. Alternatively or in combination with the preceding, the accounts 360 may be debit accounts associated with the various bank accounts held by the user 358.

In accordance with various embodiments, the user device 352 includes software that allows the user device 352 to operate in combination with the USR 356. In accordance with one embodiment, the user device 352 can initially be provided with the software or it can be retrofitted by downloading software for operation with the USR via the network 357. In one embodiment, the software is loaded via a cellular network. In another embodiment, the software is loaded via any wireless network such as a WiFi network. In a further embodiment, the software is included in a Subscriber Identity Module ("SIM") that can be removably installed in the user device 352. In yet another embodiment, the software is loaded over a hardwired communication link between the user device 352 and an access point to the network 357. Accordingly, various embodiments can allow a user to download the software for operation with the USR (including the initial receipt of the software, later updates, security patches, etc.).

In general and in accordance with one embodiment, the system 350 allows each user to employ their respective user device 352 to purchase goods or services at a wide variety of points-of-sale, and further, to make such purchases from one or more accounts selected from a plurality of accounts 360. Accordingly, the system 350 allows users to employ a mobile phone as an "electronic wallet" to select, at the point-of-sale, a particular account from among a plurality of available accounts, for example, a plurality of credit card accounts. Further, in some embodiments, the system 350 allows users to employ the approach for purchases that are made using the Internet. As mentioned above, the system 350 can also be employed in other forms of financial transactions including banking transactions and investment transactions.

In accordance with some embodiments, the user device 352 is activated for a transaction when the user satisfactorily completes an authentication process with the device. In some embodiments, the entry of a PIN number known to the user is employed to activate the device. In some embodiments, the software included in the user device 352 and employed in conducting transactions using the system 350 remains inoperative until the entry of the correct PIN. In a further embodiment, the data (for example, contact lists and associated information) stored in the user device 352 is unavailable or unintelligible until the entry of the correct PIN. In accordance with one embodiment, the data in the user device 352 is stored following a mathematical operation that acts to modify the data such that it is unintelligible. In this example, the user device 352 employs the PIN supplied by the user to reverse the mathematical operation, for example, by performing an exclusive or operation ("XOR") on the data using the PIN to render the data legible. In other words, this embodiment provides a secure embodiment of the user device that is useless in the hands of a user without knowledge of the PIN information, as without the entry of the PIN, the data stored on the device is useless.

In a further embodiment, the above approach is used to disable the software employed by the user device 352. That is, a mathematical operation is performed on software stored in the user device 352 with the PIN. Once the mathematical operation is performed the modified software is unusable and the software remains inoperative until the PIN is supplied by the user. Here too, an XOR operation may be employed to recover the software, which allows the software to operate.

In accordance with one embodiment, the preceding approaches provide an increased level of security because the theft of the user device 352 (for example, the mobile phone) is not enough for the thief to employ the user device 352. Instead, a third party in possession of the user device 352 cannot employ the device to conduct a transaction without knowledge of the PIN.

Some embodiments can employ a multi-factor authentication process before allowing a user to employ the user device 352 to conduct a transaction. That is, the system 350 can authenticate a user based on something the user knows, something the user is, and something that the user has. According to one embodiment, the user device 352 is included in the last element of the three factors. For example, many electronic devices, including mobile phones, include an electronic serial number. Thus, in one embodiment, the user is authenticated and allowed to conduct a transaction with the USR 356 by providing something the user knows (for example, a PIN), something the user is (for example, a biometric measurement as detected by the biometric sensor 367) and something the user possesses (for example, the mobile phone as evidenced by the correct electronic serial number). In accordance with this embodiment, the PIN, the biometric information and the electronic serial number are communicated to the USR 356 where the user is authenticated. In various embodiments, the multiple pieces of data can be combined (for example, cryptographically combined through known encryption techniques) before being communicated. The transaction and/or access to the user's account info are permitted when an authentication is successful. Conversely, a transaction can be denied/refused where the authentication is unsuccessful, for example, where one or more of the PIN, the biometric information and the electronic serial number are incorrect.

According further embodiments, the multi-factor authentication process can also employ the identification of the account selected by the user for the current transaction. That is, the system 350 can authenticate the user based on a combination of two or more of something the user knows, something the user is, something that the user has and an account selected by the user for the current transaction (i.e., the transaction for which the authentication is being completed). For example, in one embodiment, encrypted authentication information is generated from a non-predictable value generated by the user device 352, identifying information for the selected user account 360, and at least one of the biometric information and secret information the user knows (for example, a PIN). According to one embodiment, the authentication information (for example, encrypted authentication information) is communicated to the secure registry for authentication and approval of the requested account access and/or financial transaction. In a further embodiment, one or more aspects of the authentication and approval are completed at the POS, for example, using the POS device 354, while in another embodiment, the POS provides a conduit or communication path from the user device 352 to the secure registry 356.

According to another embodiment, the user device 352 is secured such that authentication information cannot be generated by the user device 352 prior to an authentication of the user based on the biometric input provided to the user device 352. In one embodiment, the user device 352 performs the authentication. In another embodiment, the POS device 354 authenticates the biometric information provided by the user. In yet another embodiment, the biometric information is authenticated by the secure registry 356.

According to one embodiment, any two of the PIN, the biometric information, the electronic serial number, a discrete code associated with the device and the identifying information concerning the selected account are employed to generate a seed from which further authentication information is generated, for example, to generate a seed from which a non-predictable value can be generated by the user device 352. For example, in one embodiment, the seed is employed in an algorithm that also employs a temporal value to generate the authentication information. In one embodiment, the seed and the further authentication information are generated at the user device 352 and are provided to either or both of the second device 354 and the USR 356. Either or both of the second device and the USR can use the authentication information to authenticate or validate the identity of the user of the device 352, as has been described herein. In accordance with another embodiment, all four of the PIN, the biometric information, the electronic serial number and the identifying information concerning the selected account are employed to generate the seed. In one embodiment, the discrete code that is associated with the device is also used in combination with each of the preceding to generate the seed.

In some embodiments, the discrete code that is associated with the device is provided in lieu of the electronic serial number while in other embodiments the unique code is employed with the electronic serial number to generate the seed. In one embodiment, the discrete code is unique to the user device 352. In accordance with one embodiment, the discrete code is inaccessible to an individual in possession of the device. Further, the discrete code may be maintained by the user device 352 such that any indication that the security of the device is compromised results in the discrete code being set to a default value (for example, zero) which effectively prevents valid authentication information from being generated by the user device 352. As just one example, the preceding security measure can be taken when the device receive an indication that it is being used under duress.

In another embodiment, a challenge/response protocol is employed, for example, where the USR 356 communicates a challenge to the user device 352 and access to the USR is only granted where the user's response is correct. In accordance with one embodiment, a correct response is generated using any of the PIN, the biometric information and the electronic serial number in combination with the information provided as the challenge. As has been discussed herein, the challenge/response protocol can be invisible and seamless to the user of the device 352, since other than the user providing any of PIN and/or biometric information, the communication protocol of the challenge/response protocol can be done in the background without active participation from the user.

According to some embodiments, the validation of the biometric information provided by the user can be performed on a character by character basis. For example, where the biometric information includes a spoken word or phrase, each spoken character (whether alpha or numeric) can be individually evaluated to determine whether it was provided by a user authorized to employ the user device 352. In various embodiments, the authentication of the biometric occurs at the user device 352, at the POS device 354, at the USR 356 or at a combination of the preceding.

In accordance with some embodiments, the security of the system may be further increased where the system 350 allows for one or more approaches to limit the use of the user device 352. For example, according to one embodiment, the system allows a user to establish limitations on the use of the user device 352. For example, a user may establish an active period or periods as the only period(s) that the user device 352 can be used in combination with the USR 356. Accordingly, the active period may include a temporal element. For example, the active period may be so many consecutive hours or days beginning from the start of the activation period, a fixed period of time during every day, certain days of the week, etc. As should be apparent to those of skill in the art, in one embodiment, operation of the user device 352 may be completely disabled outside of the designated active period(s). In the embodiment illustrated in FIG. 31 where the system 350 is employed for financial transactions including credit card purchases, the user may limit the use of the user device 352 to conduct such transactions to a maximum amount of a single transaction, a maximum cumulative amount of all transactions, a maximum quantity of transactions and/or a predetermined monetary amount. According to some embodiments, each of the preceding can be employed alone or in combination with a temporal element such that, for example, the maximums are determined for an active period of time having a known length. Further, the values may be set by the user, or for example, by an issuer of the user device 352. Alternatively, the maximum values may be provided by an issuer of one or more of the plurality of user accounts 360.

As a further security enhancement, the user device 352 can be configured to cease operating when an unauthorized use of the device is detected. The unauthorized use may be detected where the user 352 provides an indication that the device is being used under duress as described above. In one embodiment, a transaction in which a user signals the use under duress proceeds but the user device 352 becomes inoperative for one or more subsequent transactions. In a further embodiment, the system 350 communicates information concerning the situation to local law enforcement, for example, the location of the user device and the identity and/or appearance of the user. According to one embodiment, a constant is added to the value of the PIN when the user device 352 is being used under duress. For example, the user can enter a value which corresponds to the PIN plus one.

In some embodiments, the USR 356 provides consolidated security for the plurality of user accounts associated with a plurality of individual service companies (i.e., VISA MasterCard, etc.) who employ USR. In some embodiments, this avoids the need for the individual service companies to separately monitor the security of transactions for each of their respective accounts even where the service companies are not be affiliated with one another.

In a further embodiment, the user device 352 may destroy data/information present in the user device based on the occurrence of an event or multiple events. In one embodiment, this action is the result of evidence of tampering with the user device 352, for example, the repeated entry of an incorrect PIN. In another embodiment, the user device 352 destroys sensitive information (or a subset of information included in the user device 352) following the passage of a predetermined period of time of, for example, inactivity. It is also to be appreciated that, in an embodiment, the underlying data and/or software need not be destroyed in the above events, but instead there may be a lockout period as a result of the above events for which the device is rendered unusable. This lockout period may be extended and/or increased for repeated events discussed above.

It is to be appreciated, as has been discussed herein, that according to some embodiments, biometric information of a user of the first device or authentication of biometric information of the user of the first device can be provided to the second device 354 for any of the purposes described herein in any of the following ways: at least in part from the first device 352, at least in part from the USR 356, and at least in part from reading the biometric data stored on the second device.

In accordance with one embodiment where wireless communication is employed to communicate information between the user device 352 and the POS device 354 (for example, communication via Bluetooth protocol), the POS device may receive signals from a plurality of user devices 352 in the vicinity of the POS device 354. Accordingly, the POS device 354 may be employed to select from a plurality of users to conduct a transaction. For example, where an image of each of the users in the vicinity is displayed at the POS device 354, the individual operating the POS device 354 may select the user (and associated accounts) by selecting the photo of the user who is employing the user device 352 for the current transaction.

It is to be appreciated, as has been discussed herein, that according to some embodiments the system 350 including the USR 356 is used to provide authorization for an occurrence of an event, such as a credit or debit transaction, without providing secure information such as the credit or debit card number. In particular, for such embodiments, the USR either by itself or in combination with credit or banking authority, authenticates the user of the first device and the selected account information and either provides a one time code for authorizing the transaction or a denial to the second device, which can be displayed on the second device to indicate the approval or denial of the transaction to the POS operator. It also to be appreciated that the system can also be employed, for example, for internet purchase through a web site where the USR can alone or in combination approves or denies the transaction and provides the approval or denial to the operator of the web site, for example, where the user of the first device 352 either manually logs into a web site and provides account information, or where the user of the first device communicates via the first device 352 and the token provided by the first device with the web site. It is also to be appreciated that the code or information displayed at the second device 354 can enable many forms of a transaction not just limited to a credit or debit transaction. It can include approval for enablement of any of the events that have been described herein. In addition, the code or information can, for example, provide authorization or security that funds exist in the account to cover a check written by the user of the first device, in effect providing a code that turns the personal check into a certified check, without the need for the user of the first device having to obtain a bank check.

In various embodiments of the preceding system, the system 350 can be employed as a peer to peer network. For example, the first device and the second device are configured as peer to peer devices, in combination with the USR 356 or in some embodiments without the needs for information in the USR 356, as has been discussed herein, to authenticate and/or validate an identity of a user of the first device to the second device and in addition to authenticate and/or validate an identity of a user of the second device to the first device, to allow an occurrence of an event, such as a credit or debit transaction, access to a secure location, passport identification information and the like.

Although the above-described system 350 employs the USR 356 to facilitate the preceding operations, the above approach may be employed with alternative systems that include a secure database with the user's account information. Further, although the preceding description concerning FIG. 31 primarily discusses sales transactions, the system 350 may be employed in a variety of fields to allow only authorized access by authenticated users to secure data, for example, as illustrated in FIG. 4, and the like as has been described herein.

Further, the user device can in some embodiments be used to authenticate identity in a variety of applications. That is, an authentication code can be generated by the user device 352 as described above where the authentication code is used to determine whether the user is authorized to take one or more actions. According to one embodiment, the authentication code is provided to a security system to determine whether the user is permitted to access a physical facility, for example, to determine whether the user is permitted to access a residence or a place of business. In a further embodiment, the user device 352 wirelessly communicates an authentication code to a home security system as part of an access request. The authentication code generated by the user device 352 can be used in a similar manner to determine whether an individual can access a computer network, for example, log in. According to additional embodiments, such an authentication code can also be used to provide positive identification of an individual in possession of the user device 352 in the manner of a passport, driver's license or other form of identification issued by the government or another third party such as an employer.

In one embodiment, a user device is configured to allow a user to select any one of a plurality of accounts associated with the user to employ in a financial transaction. In one embodiment, the user device includes a biometric sensor configured to receive a biometric input provided by the user, a user interface configured to receive a user input including secret information known to the user and identifying information concerning an account selected by the user from the plurality of accounts. In a further embodiment, the user device includes a communication link configured to communicate with a secure registry, and a processor coupled to the biometric sensor to receive information concerning the biometric input, the user interface, and the communication link. According to one embodiment, the processor is configured to generate a non-predictable value and to generate encrypted authentication information from the non-predictable value, the identifying information, and at least one of the information concerning the biometric input and the secret information, and to communicate the encrypted authentication information via the communication link to the secure registry. According to another embodiment, the secret information includes the identifying information.

In a further embodiment, the communication link wirelessly transmits the encrypted authentication information to a point-of-sale (POS) device, and the POS device is configured to transmit at least a portion of the encrypted authentication information to the secure registry. Further, the POS device can include a magnetic stripe reader.

In yet another embodiment, the communication link wirelessly transmits the encrypted authentication information to a converter device configured to generate an emulated magnetic stripe output for use with the POS device.

In still another embodiment, the user device includes a memory coupled to the processor where the memory stores information employed by the device to authenticate the biometric received by the biometric sensor. In one embodiment, the device does not permit the entry of the user input if the biometric input received by the biometric sensor is determined to not belong to an authorized user of the device.

According to a further embodiment, the secret information known to the user includes a PIN, and the authentication of the secret information and the biometric input activate the device for the financial transaction. In one embodiment, the user device includes a memory coupled to the processor and the data stored in the memory is unavailable to an individual in possession of the device until the device is activated. According to his embodiment, the data can be subject to a mathematical operation that acts to modify the data such that it is unintelligible until the device is activated.

In accordance with some embodiments, a method of generating authentication information includes acts of authenticating an identity of a user to a device based on at least one of biometric data received by the device from the user and secret information known to the user and provided to the device. The method can also include the generation of a non-predictable value with the device. The method can further include acts of receiving identifying information from the user concerning a selected one of a plurality of user accounts and generating encrypted authentication information from the non-predictable value, the identifying information, and at least one of the biometric data and the secret information. In a further embodiment, the device can generate encrypted authentication information from each of the non-predictable value, the biometric data, the secret information, and the identifying information.

In accordance with another embodiment, the method includes an act of de-activating the device without generating the encrypted authentication information if the identity of the user is not successfully authenticated to the device. Embodiments may also include an act of generating encrypted authentication information in a manner that allows the identification of the user and the selected one of the plurality of user accounts by a secure registry.

According to a still further embodiment, a method of controlling access to a plurality of accounts is provided where the method includes acts of generating, with a device, encrypted authentication information from a non-predictable value generated by the device, identifying information concerning an account selected by a user of the device from among a plurality of accounts associated with the user, and at least one of a biometric of the user received by the device and secret information provided to the device by the user, communicating the encrypted authentication information from the device to a secure registry via a point-of-sale (POS) device to authenticate or not authenticate the device with the secure registry, authorizing the POS device to initiate a financial transaction involving a transfer of funds to or from the account selected by the user when the encrypted authentication information is successfully authenticated, and denying the POS device from initiation of the financial transaction involving a transfer of funds to or from the account selected by the user when the encrypted authentication information is not successfully authenticated.

According to a further embodiment, the method includes an act of authenticating an identity of the user by validating the biometric with one of the device and the secure registry. In some embodiments, the biometric can be validated on a character-by-character basis.

According to yet another embodiment, the method includes an act of transmitting image data from the secure registry to the POS device along with an authorization authorizing the POS device to initiate the financial transaction provided that the image data when processed at the POS device authenticates an identity of the user. In a further embodiment, the method also includes an act of authenticating the identity of the user at the POS device by any of displaying an image of the user at the POS device for visual confirmation by an operator of the POS device and processing biometric data provided by the image data. The operator may be a store clerk, bank clerk, security personnel or an individual in any other capacity in which they are tasked with a responsibility to verify an identity of an individual in possession of the user device.

In accordance with one embodiment, the secure registry includes a database containing information concerning a plurality of accounts associated with a different one of a plurality of users, respectively. Further, the plurality of accounts can include accounts associated with a plurality of different financial service providers. According to some embodiments, the method can include an act of transmitting information including at least a portion of the encrypted authentication information to the secure registry from the POS device.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An electronic ID device configured to allow a user to select an account associated with the user to employ in a transaction, the electronic ID device comprising:
   a biometric sensor configured to receive a biometric input provided by the user;
   a user interface configured to receive a user input, the user input including:
      secret information known to the user; and
      selection information concerning an account selected by the user from one or more accounts associated with the user;
   a communication interface configured to communicate with a secure registry; and
   a processor coupled to the biometric sensor to receive information concerning the biometric input, wherein the processor is programmed to:
      activate transaction software of the electronic ID device in response to a successful authentication of a user's identity, wherein authentication of the user's identity is based on at least one of the biometric input and the secret information;
      generate a one-time non-predictable value;
      obtain a public identifier that corresponds to private account information of the selected user account, wherein the public identifier does not contain any private account information of the selected user account;
      generate authentication information from the one-time non-predictable value and the public identifier;
      encrypt the authentication information; and
      wirelessly communicate the encrypted authentication information to a requesting or receiving device via an authentication signal generated by the communication interface, such that the secure registry:
         receives a transaction request and at least a portion of the encrypted authentication information from the requesting or receiving device, wherein the transaction request involves the selected user account;
         decrypts the encrypted authentication information;
         verifies the decrypted authentication information without using the private account information;
         uses the public identifier from the encrypted authentication information to acquire the private account information of the selected user account; and
         generates an enablement signal to enable the transaction request without transmitting the private account information.

2. The electronic ID device of claim 1, wherein the communication interface is configured to communicate with the secure registry either directly or via an intermediate device.

3. The electronic ID device of claim 1, wherein the processor is further programmed to wirelessly communicate the encrypted authentication information to the requesting or receiving device via an induced signal generated by the communication interface.

4. The electronic ID device of claim 1, wherein the communication interface includes a magnetic stripe emulator.

5. The electronic ID device of claim 4, wherein:
the processor is further programmed to wirelessly communicate the encrypted authentication information to the requesting or receiving device via a time-varying signal which emulates data provided by a magnetic-stripe card to a magnetic card reader; and
the time-varying signal is generated by the magnetic stripe emulator of the communication interface.

6. The electronic ID device of claim 1, wherein the processor is further programmed to wirelessly communicate the encrypted authentication information to the requesting or receiving device via a near field signal generated by the communication interface.

7. The electronic ID device of claim 1, wherein:
the communication interface includes a near field communication (NFC) transceiver; and
the authentication signal generated by the communication interface is an NFC signal.

8. The electronic ID device of claim 7, wherein:
the NFC signal is generated by the NFC transceiver of the communication interface; and
the processor is further programmed to wirelessly communicate the encrypted authentication information to the requesting or receiving device via the NFC signal, the requesting or receiving device located within the same local area as the NFC transceiver such that the NFC signal is transmitted directly between the NFC transceiver and the requesting or receiving device.

9. The electronic ID device of claim 1, wherein the processor is further programmed to wirelessly communicate the encrypted authentication information to the requesting or receiving device via a Wi-Fi™ radio technology signal generated by the communication interface.

10. The electronic ID device of claim 1, wherein the processor is further programmed to wirelessly communicate the encrypted authentication information to the requesting or receiving device via a Bluetooth™ wireless technology standard signal.

11. The electronic ID device of claim 1, wherein the processor is further programmed to wirelessly communicate the encrypted authentication information to the requesting or receiving device via a Bluetooth™ Low Energy wireless technology standard signal.

12. The electronic ID device of claim 1, wherein in activating the transaction software of electronic ID device, the processor is further programmed to render stored data legible.

13. The electronic ID device of claim 1, wherein the encrypted authentication information is one-time encrypted authentication information.

14. The electronic ID device of claim 1, wherein the communication interface is configured to communicate the encrypted authentication information to the secure registry, where the secure registry comprises a secure token database storing one or more tokens associated with the authentication information.

15. The electronic ID device of claim 1, wherein the processor is further programmed to deactivate features of the electronic ID device without generating the authentication information where authentication based on at least one of the biometric input and the secret information is unsuccessful.

16. The electronic ID device of claim 15, wherein deactivating the features of the electronic ID device initiates a lock-out period.

17. The electronic ID device of claim 15, wherein deactivating the features of the electronic ID device includes deleting information present in the electronic ID device that is used to generate the authentication information.

* * * * *

UNITED STATES PATENT AND TRADEMARK OFFICE
CERTIFICATE OF CORRECTION

PATENT NO. : 10,832,245 B2  
APPLICATION NO. : 16/833006  
DATED : November 10, 2020  
INVENTOR(S) : Kenneth P. Weiss Page 1 of 1

It is certified that error appears in the above-identified patent and that said Letters Patent is hereby corrected as shown below:

In the Specification

Column 28, Line 13, insert -- -- i.e., -- before "whether".

Column 36, Line 32, delete "PM" and insert -- PKI --.

Column 36, Line 33, delete "PM" and insert -- PKI --.

Column 37, Line 17, delete "PM" and insert -- PKI --.

Column 38, Line 2, delete "PM" and insert -- PKI --.

Column 38, Line 54, delete "PM" and insert -- PKI --.

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*